US 9,080,204 B2

(12) United States Patent
Fischer et al.

(10) Patent No.: US 9,080,204 B2
(45) Date of Patent: *Jul. 14, 2015

(54) COMPOSITIONS AND METHODS FOR RAPID, REAL-TIME DETECTION OF INFLUENZA A VIRUS (H1N1) SWINE 2009

(75) Inventors: Gerald W. Fischer, Bethesda, MD (US); Luke T. Daum, San Antonio, TX (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 201 days.

This patent is subject to a terminal disclaimer.

(21) Appl. No.: 13/341,314

(22) Filed: Dec. 30, 2011

(65) Prior Publication Data

US 2012/0115126 A1    May 10, 2012

Related U.S. Application Data

(63) Continuation of application No. 12/510,968, filed on Jul. 28, 2009, now Pat. No. 8,097,419, and a continuation-in-part of application No. 13/328,992, filed on Dec. 16, 2011, which is a continuation of application No. 12/426,890, filed on Apr. 20, 2009, now Pat. No. 8,080,645, application No. 13/341,314, which is a continuation-in-part of application No. 13/094,809, filed on Apr. 26, 2011, now Pat. No. 8,652,782, and a continuation-in-part of application No. 12/916,263, filed on Oct. 29, 2010, and a continuation-in-part of application No. 13/332,204, filed on Dec. 20, 2011, now Pat. No. 8,293,467, which is a continuation of application No. 12/243,949, filed on Oct. 1, 2008, now Pat. No. 8,084,443, and a continuation-in-part of application No. 11/844,933, filed on Aug. 24, 2007, now abandoned.

(60) Provisional application No. 60/976,728, filed on Oct. 1, 2007, provisional application No. 60/843,711, filed on Sep. 12, 2006.

(51) Int. Cl.
| C12Q 1/68 | (2006.01) |
| C12Q 1/70 | (2006.01) |
| C12P 19/34 | (2006.01) |

(52) U.S. Cl.
CPC .............. *C12Q 1/6851* (2013.01); *C12Q 1/701* (2013.01)

(58) Field of Classification Search
None
See application file for complete search history.

(56) References Cited

U.S. PATENT DOCUMENTS

| 4,116,777 A | 9/1978 | Takátsy et al. |
| 4,196,265 A | 4/1980 | Koprowski et al. |
| 4,235,244 A | 11/1980 | Abele et al. |
| 4,315,073 A | 2/1982 | Brown et al. |
| 4,355,102 A | 10/1982 | Quash |
| 4,356,170 A | 10/1982 | Jennings et al. |
| 4,372,945 A | 2/1983 | Likhite |
| 4,474,757 A | 10/1984 | Arnon et al. |
| 4,529,702 A | 7/1985 | Bryan |
| 4,554,101 A | 11/1985 | Hopp |
| 4,578,770 A | 3/1986 | Mitani |
| 4,588,680 A | 5/1986 | Bucher et al. |
| 4,596,792 A | 6/1986 | Vyas |
| 4,599,230 A | 7/1986 | Milich et al. |
| 4,601,903 A | 7/1986 | Frasch |
| 4,608,251 A | 8/1986 | Mia |
| 4,634,664 A | 1/1987 | Oestberg |
| 4,634,666 A | 1/1987 | Engleman et al. |
| 4,668,476 A | 5/1987 | Bridgham et al. |
| 4,683,195 A | 7/1987 | Mullis et al. |
| 4,683,202 A | 7/1987 | Mullis |
| 4,707,450 A | 11/1987 | Nason |
| 4,744,982 A | 5/1988 | Hunter et al. |
| 4,746,490 A | 5/1988 | Saneii |
| 4,749,490 A | 6/1988 | Smyth et al. |
| 4,800,159 A | 1/1989 | Mullis et al. |
| 4,803,998 A | 2/1989 | Kezes et al. |
| 4,816,513 A | 3/1989 | Bridgham et al. |
| 4,883,750 A | 11/1989 | Whiteley et al. |
| 4,954,449 A | 9/1990 | Hunter et al. |
| 4,981,782 A | 1/1991 | Judd et al. |
| 4,996,143 A | 2/1991 | Heller et al. |
| 5,091,316 A | 2/1992 | Monthony et al. |
| 5,108,927 A | 4/1992 | Dorn |
| 5,136,019 A | 8/1992 | Judd et al. |

(Continued)

FOREIGN PATENT DOCUMENTS

| EP | 0 313 224 A1 | 4/1989 |
| EP | 320308 | 6/1989 |

(Continued)

OTHER PUBLICATIONS

PCT Patentability Report for PCT/US2012/35253, dated Sep. 21, 2012.

(Continued)

*Primary Examiner* — Kenneth R. Horlick
*Assistant Examiner* — David Thomas
(74) *Attorney, Agent, or Firm* — Remenick PLLC

(57) ABSTRACT

Disclosed are oligonucleotide amplification primers and detection probes specific for the amplification and detection of pathogenic organisms, including for example, specific Influenza A H1N1 viral isolates. Also disclosed is a biological organism identification kit including the disclosed nucleic acid probes and primers, as well as thermal cycling reagents that is both portable and durable, and may also be self-contained for remote, or in-field analysis and identification of particular influenza isolates from a variety of biological specimen types.

17 Claims, 12 Drawing Sheets

(56) References Cited

U.S. PATENT DOCUMENTS

| | | |
|---|---|---|
| 5,145,684 A | 9/1992 | Liversidge et al. |
| 5,149,653 A | 9/1992 | Roser |
| 5,163,441 A | 11/1992 | Monthony et al. |
| 5,168,039 A | 12/1992 | Crawford et al. |
| 5,182,109 A | 1/1993 | Tamura et al. |
| 5,186,898 A | 2/1993 | Bridgham et al. |
| 5,187,060 A | 2/1993 | Cerutti et al. |
| 5,234,809 A | 8/1993 | Boom |
| 5,243,030 A | 9/1993 | Judd et al. |
| 5,252,458 A | 10/1993 | Liav et al. |
| 5,290,686 A | 3/1994 | Kendal et al. |
| 5,316,910 A | 5/1994 | Rota et al. |
| 5,399,363 A | 3/1995 | Liversidge et al. |
| 5,482,856 A | 1/1996 | Fell, Jr. et al. |
| 5,503,841 A | 4/1996 | Doyle et al. |
| 5,543,158 A | 8/1996 | Gref et al. |
| 5,545,555 A | 8/1996 | Racioppi et al. |
| 5,552,157 A | 9/1996 | Yagi et al. |
| 5,565,213 A | 10/1996 | Nakamori et al. |
| 5,565,322 A | 10/1996 | Heller |
| 5,567,434 A | 10/1996 | Szoka, Jr. |
| 5,571,511 A | 11/1996 | Fischer |
| 5,589,174 A | 12/1996 | Okuno et al. |
| 5,627,071 A | 5/1997 | Triva |
| 5,631,350 A | 5/1997 | Okuno et al. |
| 5,641,515 A | 6/1997 | Ramtoola |
| 5,656,016 A | 8/1997 | Ogden |
| 5,663,055 A | 9/1997 | Turner et al. |
| 5,679,356 A | 10/1997 | Bonnem et al. |
| 5,691,299 A | 11/1997 | Fabry |
| 5,697,899 A | 12/1997 | Hillman et al. |
| 5,702,944 A | 12/1997 | Racioppi et al. |
| 5,719,020 A | 2/1998 | Liav et al. |
| 5,736,333 A | 4/1998 | Livak et al. |
| 5,738,868 A | 4/1998 | Shinkarenko |
| 5,741,516 A | 4/1998 | Webb et al. |
| 5,766,841 A | 6/1998 | Liav et al. |
| 5,770,219 A | 6/1998 | Chiang et al. |
| 5,779,708 A | 7/1998 | Wu |
| 5,783,208 A | 7/1998 | Venkateshwaran et al. |
| 5,785,975 A | 7/1998 | Parikh |
| 5,795,582 A | 8/1998 | Wright |
| 5,795,587 A | 8/1998 | Gao et al. |
| 5,797,898 A | 8/1998 | Santini, Jr. et al. |
| 5,800,810 A | 9/1998 | Doyle et al. |
| 5,849,489 A | 12/1998 | Heller |
| 5,891,624 A | 4/1999 | Huang |
| 5,945,515 A | 8/1999 | Chomczynski |
| 5,955,074 A | 9/1999 | Fischer |
| 5,958,379 A | 9/1999 | Regenold et al. |
| 6,015,664 A | 1/2000 | Henrickson et al. |
| 6,033,673 A | 3/2000 | Clements |
| 6,060,068 A | 5/2000 | Doyle et al. |
| 6,136,585 A | 10/2000 | Ball et al. |
| 6,162,603 A | 12/2000 | Heller |
| 6,168,915 B1 | 1/2001 | Scholl et al. |
| 6,242,582 B1 | 6/2001 | Reece et al. |
| 6,280,928 B1 | 8/2001 | Scholl et al. |
| 6,306,404 B1 | 10/2001 | LaPosta et al. |
| 6,306,582 B1 | 10/2001 | Scholl et al. |
| 6,312,395 B1 | 11/2001 | Tripp et al. |
| 6,376,172 B1 | 4/2002 | Scholl et al. |
| 6,406,842 B2 | 6/2002 | Scholl et al. |
| 6,440,423 B1 | 8/2002 | Clements et al. |
| 6,451,325 B1 | 9/2002 | Van Nest et al. |
| 6,458,577 B1 | 10/2002 | Huang |
| 6,495,316 B1 | 12/2002 | Scholl et al. |
| 6,500,432 B1 | 12/2002 | Dalemans et al. |
| 6,503,745 B1 | 1/2003 | Chand et al. |
| 6,534,065 B1 | 3/2003 | Makin et al. |
| 6,572,866 B1 | 6/2003 | Torcia |
| 6,573,080 B2 | 6/2003 | Scholl et al. |
| 6,602,510 B1 | 8/2003 | Fikes et al. |
| 6,603,908 B2 | 8/2003 | Dallas et al. |
| 6,603,998 B1 | 8/2003 | King et al. |
| 6,610,293 B1 | 8/2003 | Fischer et al. |
| 6,610,474 B1 | 8/2003 | Huang |
| 6,627,396 B1 | 9/2003 | Swanson et al. |
| 6,632,432 B1 | 10/2003 | Fischer |
| 6,680,308 B1 | 1/2004 | Hassan |
| 6,689,363 B1 | 2/2004 | Sette et al. |
| 6,713,068 B1 | 3/2004 | Audonnet et al. |
| 6,720,409 B2 | 4/2004 | Okuno et al. |
| 6,734,292 B1 | 5/2004 | Omura et al. |
| 6,759,241 B1 | 7/2004 | Hone et al. |
| 6,780,421 B1 | 8/2004 | Haensler et al. |
| 6,793,928 B1 | 9/2004 | van Scharrenburg et al. |
| 6,811,971 B2 | 11/2004 | Klepp et al. |
| 6,855,321 B1 | 2/2005 | Rappuoli et al. |
| 6,875,600 B2 | 4/2005 | Scholl et al. |
| 6,881,835 B2 | 4/2005 | Bai et al. |
| 6,893,814 B2 | 5/2005 | Swanson et al. |
| 6,939,543 B2 | 9/2005 | Fischer et al. |
| 6,946,291 B2 | 9/2005 | Scholl et al. |
| 7,090,853 B2 | 8/2006 | Kapp et al. |
| 7,122,640 B2 | 10/2006 | Gjerde et al. |
| 7,223,409 B2 | 5/2007 | Nagata et al. |
| 7,279,162 B1 | 10/2007 | Fischer |
| 7,311,671 B2 | 12/2007 | Jung et al. |
| 7,351,413 B2 | 4/2008 | Page et al. |
| 7,357,936 B1 | 4/2008 | Garcon |
| 7,361,352 B2 | 4/2008 | Birkett et al. |
| 7,371,531 B2 * | 5/2008 | Hellyer et al. ............... 435/6.11 |
| 7,438,919 B2 | 10/2008 | Dowling |
| 7,494,771 B2 | 2/2009 | Picard et al. |
| 7,541,194 B2 | 6/2009 | Mink et al. |
| 7,547,512 B2 | 6/2009 | Peiris |
| 7,648,681 B2 | 1/2010 | Meyer et al. |
| 7,718,402 B2 | 5/2010 | Gayral et al. |
| 7,767,804 B2 | 8/2010 | Bair, Jr. et al. |
| 7,794,001 B2 | 9/2010 | Blackwell et al. |
| 8,080,645 B2 * | 12/2011 | Fischer et al. ............... 536/23.1 |
| 8,084,443 B2 | 12/2011 | Fischer et al. |
| 8,097,419 B2 | 1/2012 | Fischer et al. |
| 8,293,467 B2 | 10/2012 | Fischer et al. |
| 2001/0021501 A1 | 9/2001 | Scholl et al. |
| 2001/0023065 A1 | 9/2001 | Lee |
| 2001/0034022 A1 | 10/2001 | Scholl et al. |
| 2001/0036628 A1 | 11/2001 | Scholl et al. |
| 2002/0054882 A1 | 5/2002 | Okuno et al. |
| 2002/0055094 A1 | 5/2002 | Reece et al. |
| 2002/0081567 A1 | 6/2002 | Henrickson et al. |
| 2002/0082395 A1 | 6/2002 | Fischer et al. |
| 2002/0169140 A1 | 11/2002 | Prendergast |
| 2003/0119209 A1 | 6/2003 | Kaylor et al. |
| 2003/0143566 A1 | 7/2003 | Helftenbein |
| 2003/0203357 A1 | 10/2003 | Huang |
| 2003/0215796 A1 | 11/2003 | Scholl et al. |
| 2003/0219442 A1 | 11/2003 | Mikayama et al. |
| 2004/0009126 A1 | 1/2004 | Pilkiewicz et al. |
| 2004/0013673 A1 | 1/2004 | Fischer et al. |
| 2004/0071757 A1 | 4/2004 | Rolf |
| 2004/0082549 A1 | 4/2004 | Jomaa |
| 2004/0086849 A1 | 5/2004 | Shimasaki et al. |
| 2004/0126789 A1 | 7/2004 | Park et al. |
| 2004/0142319 A1 | 7/2004 | Yu et al. |
| 2004/0170965 A1 | 9/2004 | Scholl et al. |
| 2004/0214272 A1 | 10/2004 | La Rosa et al. |
| 2004/0223976 A1 | 11/2004 | Bianchi et al. |
| 2005/0009008 A1 | 1/2005 | Robinson et al. |
| 2005/0042229 A1 | 2/2005 | Yang et al. |
| 2005/0090009 A1 | 4/2005 | Cormier et al. |
| 2005/0112656 A1 | 5/2005 | Iwaki |
| 2005/0169941 A1 | 8/2005 | Lees |
| 2005/0170334 A1 | 8/2005 | Mikayama et al. |
| 2005/0181357 A1 | 8/2005 | Peiris et al. |
| 2005/0187213 A1 | 8/2005 | Lang et al. |
| 2005/0227269 A1 | 10/2005 | Lloyd, Jr. et al. |
| 2006/0002939 A1 | 1/2006 | Fischer et al. |
| 2006/0014185 A1 | 1/2006 | Ollikka et al. |
| 2006/0105468 A1 | 5/2006 | Winkler et al. |
| 2006/0121468 A1 | 6/2006 | Allnutt et al. |
| 2006/0134648 A1 | 6/2006 | Chou et al. |
| 2006/0286557 A1 | 12/2006 | Basehore et al. |

(56) References Cited

U.S. PATENT DOCUMENTS

| | | |
|---|---|---|
| 2007/0102946 A1 | 5/2007 | Blackwell et al. |
| 2007/0172835 A1 | 7/2007 | McBride et al. |
| 2007/0196388 A1 | 8/2007 | Dowling et al. |
| 2007/0202497 A1 | 8/2007 | Renuart et al. |
| 2007/0202511 A1 | 8/2007 | Chen et al. |
| 2007/0286871 A1 | 12/2007 | Hickle et al. |
| 2008/0003575 A1* | 1/2008 | Michalik et al. .................. 435/6 |
| 2008/0032921 A1 | 2/2008 | Alexander et al. |
| 2008/0050737 A1 | 2/2008 | Arieli et al. |
| 2008/0069821 A1 | 3/2008 | Yang et al. |
| 2008/0075708 A1 | 3/2008 | Yu et al. |
| 2008/0107665 A1 | 5/2008 | Suckow et al. |
| 2008/0107687 A1 | 5/2008 | Poulet |
| 2008/0118531 A1 | 5/2008 | Hoffmann et al. |
| 2008/0139789 A1 | 6/2008 | Fischer |
| 2008/0145373 A1 | 6/2008 | Arumugham et al. |
| 2008/0181914 A1 | 7/2008 | Eichhorn |
| 2008/0260763 A1 | 10/2008 | Felgner et al. |
| 2009/0081202 A1 | 3/2009 | Fischer et al. |
| 2009/0098527 A1 | 4/2009 | Fischer et al. |
| 2009/0233309 A1 | 9/2009 | Fischer et al. |
| 2009/0312285 A1 | 12/2009 | Fischer et al. |
| 2010/0009343 A1 | 1/2010 | Fischer et al. |
| 2010/0055672 A1 | 3/2010 | Saghbini |
| 2010/0151477 A1 | 6/2010 | Cawthon |
| 2010/0221822 A1 | 9/2010 | Fischer et al. |
| 2010/0311739 A1 | 12/2010 | Gunaratnam et al. |
| 2011/0159497 A1 | 6/2011 | Lee et al. |
| 2011/0281754 A1 | 11/2011 | Fischer et al. |
| 2012/0088231 A1 | 4/2012 | Fischer et al. |
| 2012/0100529 A1 | 4/2012 | Fischer et al. |
| 2012/0107799 A1 | 5/2012 | Daum |
| 2012/0115126 A1 | 5/2012 | Fischer et al. |
| 2012/0244527 A1 | 9/2012 | Trinh et al. |

FOREIGN PATENT DOCUMENTS

| | | |
|---|---|---|
| EP | 0 621 339 A2 | 10/1994 |
| EP | 0 675 199 A2 | 10/1995 |
| EP | 0 726 316 A2 | 8/1996 |
| EP | 1 081 496 A1 | 3/2001 |
| RU | 2150281 C1 | 10/2000 |
| WO | WO 91/02740 | 3/1991 |
| WO | WO 92/03454 | 3/1992 |
| WO | WO 92/16619 | 10/1992 |
| WO | WO 94/09035 | 4/1994 |
| WO | WO 94/17106 | 8/1994 |
| WO | WO 95/08348 | 3/1995 |
| WO | WO 97/05248 A2 | 2/1997 |
| WO | WO97/46707 | 12/1997 |
| WO | WO97/46712 | 12/1997 |
| WO | WO97/46714 | 12/1997 |
| WO | WO 98/40099 | 9/1998 |
| WO | WO01/16163 | 3/2001 |
| WO | WO 03/026567 A2 | 4/2003 |
| WO | WO 03/053462 | 7/2003 |
| WO | WO 03/095646 | 11/2003 |
| WO | WO2004/002451 | 1/2004 |
| WO | WO 2004/004658 A2 | 1/2004 |
| WO | WO 2004/043407 | 5/2004 |
| WO | WO 2004/055205 | 7/2004 |
| WO | WO 2004/072270 A1 | 8/2004 |
| WO | WO 2004/084876 A2 | 10/2004 |
| WO | WO 2005010186 | 2/2005 |
| WO | WO 2005/042784 | 5/2005 |
| WO | WO 2005/075642 A1 | 8/2005 |
| WO | WO 2005/085274 A1 | 9/2005 |
| WO | WO2006/041933 | 4/2006 |
| WO | WO 2006/138444 | 12/2006 |
| WO | WO2007051036 | 5/2007 |
| WO | WO2007056266 | 5/2007 |
| WO | WO 2007/091030 | 8/2007 |
| WO | WO 2007/133682 | 11/2007 |
| WO | WO2008079463 | 7/2008 |
| WO | WO2009085355 | 7/2009 |

OTHER PUBLICATIONS

Taiwan Office Action dated Aug. 20, 2012.
PCT Search Report for PCT/US10/31716 dated Jul. 28, 2010.
PCT Written Opinion for PCT/US10/31716 dated Oct. 25, 2011.
http://www.ncbi.nlm.nlh.gov/genomes/FLU/SwineFlu2009.html, NCBI Influenza Virus Resource "CLE I. GenBank Sequences from Pandemic (H1N1) 2009 Viruses". 1237 pages.
Morré, S.A., et al., "RNA Amplification by Nucleic Acid Sequence-Based Amplification with an Internal Standard Enables Reliable Detection of *Chlamydia trachomalis* in Cervical Scrapings and Urine Samples," *J. Clin. Microbiol.* 34(12): 3108-3114 (1996).
Rosenstraus, M., et al., "An Internal Control for Routine Diagnostic PCR: Design, Properties, and Effect on Clinical Performance," *J. Clin. Microbiol.* 36(1): 191-197 (1998).
Buck, G.A., et al., "Design Strategies and Performance of Custom DNA Sequencing Primers," *BioTechniques* 27: 528-536 (1999).
Magari, R.T., "Assessing Shelf Life Using Real-Time and Accelerated Stability Tests," *BioPharm*; International.com (2003).
Hindiyeh, M., et al., "Evaluation of a Multiplex Real-Time Reverse Transcriptase PCR Assay for Detection and Differentiation of nfluenza Viruses A and B during the 2001-2002 Influenza Season in Israel," *J. Clin. Microbiol.* 43(2): 589-595 (2005).
Daum, L.T., el al., Abstract and Poster—"Development of a Real Time Reverse-Transcription PCR (RRT-PCR) Assay for Detection of Influenza A H1N1 2009 from Clinical Respiratory Specimens," *Pediatric Infectious Disease Conference ESPID*, Nice, France, May 5-8, 2010.
Daum, L.T., et al, Abstract—"A Molecular Transport Medium (MTM) for Pathogen Inactivation, Ambient Transport and Preservation of RNA from Clinical Samples," *ICAAC*, Boston, MA, Sep. 12-15, 2010.
Wiecek, A.S., "Pocket PCR: The Whole Chain Reaction in His Hand," Biotechniques.com, Oct. 26, 2010.
Pamphlet—"Primer PCR Syster™"—Longhorn Vaccines & Diagnostics, (2008).
U.S. Appl. No. 12/243,949, filed Oct. 1, 2008, Fischer et al.
U.S. Appl. No. 12/426,890, filed Apr. 20, 2009, Fischer et al.
Chomczynski, P. and Sacchi, N., "Single-Step Method of RNA Isolation by Acid Guanidinium Thiocyanate—Phenol—Chloroform Extraction," *Anal. Biochem.*, 162:156-9 (1987).
Tortora, et al., "Tools of Biochemistry 5A—Ways to Isolate and Purify Proteins and Other Macromolecules," *Microbiology—An Introduction*, pp. 152-155, 4$^{th}$ Ed., The Benjamin/Cummings Publishing Company, Inc., United States (1992).
Ramanujam, R. et al., "Room-Temperature-Stable PCR Reagents," Cold Spring Harbor Laboratory Press, *PCR Methods and Appl.*, 3:75-76 (1993).
Wolff, C. et al, "Single-Tube Nested PCR With Room-Temperature-Stable Reagents," Cold Spring Harbor Laboratory Press, *PCR Methods and Appl.*, 4:376-79 (1995).
Matthews, et al., "Immunofluorescence and Fluorescent Antibody Techniques," *Biochemistry*, pp. 461-463, 2$^{nd}$ Ed., The Benjamin/Cummings Publishing Company, Inc., United States (1996).
Schultz, C.L. et al., "A Lysis, Storage, and Transportation Buffer for Long-Term, Room-Temperature Preservation of Human Clinical Lymphoid Tissue Samples Yielding High Molecular Weight Genomic DNA Suitable for Molecular Diagnosis," *Am. J. Clin. Pathol.*, 111(6):748-52 (1999).
Daum, L.T. et al., "Genetic and Antigenetic Analysis of the First A/New Caledonia/20/99-Like H1N1 Influenza Isolates Reported in the Americas," *Emerg. Infect. Dis.*, 8(4):408-12 (Apr. 2002).
De Moreau de Gerbehaye, A.I. et al., "Stable Hepatitis C Virus RNA Detection by RT-PCR During Four Days Storage," BioMed Central, *BMC Infectious Diseases*, 2:22 (2002).
Daum, L.T. et al., "A Rapid, Single-Step Multiplex Reverse Transcription-PCR Assay for the Detection of Human H1N1, H3N2 and B Influenza Viruses," *J. of Clinic. Virol.*, 25(3): 345-50 (2002).

(56) References Cited

OTHER PUBLICATIONS

Spackman, E. et al., "Development of a Real-Time Reverse Transcriptase PCR Assay for Type A Influenza Virus and the Avian H5 and H7 Hemagglutinin Subtypes," *J. of Clinic. Microbiol.*, 40(9): 3256-60 (2002).

Blacksell, S.D. et al., "The Effect of Sample Degradation and RNA Stabilization on Classical Swine Fever Virus RT-PCR and ELISA methods," *J. Virol. Methods*, 118(1):33-7 (2004).

Fouchier, R.A.M. et al., "Characterization of a Novel Influenza A Virus Hemagglutinin Subtype (H16) Obtained From Black-Headed Gulls," *J. of Virol.*, 79(5):2814-22 (Mar. 2005).

Krafft, A.E. et al., "Evaluation of PCR Testing of Ethanol-Fixed Nasal Swab Specimens as an Augmented Surveillance Strategy for Influenza Virus and Adenovirus Identification," *J. of Clinic. Microbiol.*, 43(4):1768-75 (Apr. 2005).

Pheng, O.C. et al., "Temperature Related Storage Evaluation of an RT-PCR Test Kit for the Detection of Dengue Infection in Mosquitoes," (Research Note), *Tropical Biomedicine*, 22(11):73-6 (2005).

"USB Taq PCR Master Mix in qPCR," USB Corporation, *Tech Tips*, 207 (2005).

Bright, R.A., et al., "Adamantane Resistance Among Influenza A Viruses Isolated Early During the 2005-2006 Influenza Season in the United States," *JAMA*, 295(8):891-4 (Feb. 22, 2006).

Das, A. et al., "Development of an Internal Positive Control for Rapid Diagnosis of Avian Influenza Virus Infections by Real-Time Reverse Transcription-PCR with Lyophilized Reagents," *J. of Clinic. Microbiol.*, 44(9):3065-73 (Sep. 2006).

Daum, L.T., et al., "Molecular Analysis of Isolates From Influenza B Outbreaks in the U.S. and Nepal, 2005," *Arch. of Virol.*, 151:1863-1874 (2006).

Lin, B. et al., "Broad-Spectrum Respiratory Tract Pathogen Identification Using Resequencing DNA Microarrays," *Genome Res.*, 16(4): 527-35 (2006).

Mohany, J. et al., "Multiplex RT-PCR for Detecting Nineteen Respiratory Viruses," *J. of Clinic. Virol.*, 36: S9 (2006).

Daum, L.T. et al., "Real-Time RT-PCR Assays for Type and Subtype Detection of Influenza A and B Viruses," *Influenza & Other Resp. Viruses*, 1(4): 167-75 (2007).

"PCR-Ready Clear Supreme™," Syntezza Bioscience Ltd., available at http://www.syntezza.com/egt/PCR-Ready_Clear_Supreme.pdf (2006).

Wang, Z., et al., "Identifying Influenza Viruses with Resequencing Microarrays," *Emerg. Infect. Dis.* 12(4):638-46 (2006).

"TechNotes Newsletter," *Applied Biosystems*, 14(4):1-37 (2007).

Daum, L.T., et al., "Poster—A Rapid, Simplified Collection-to-Detection System for Typing and Subtyping Influenza Viruses Using Real-Time RT-PCR and Culture," *American Society for Microbiology (ASM) Conference on Emerging Technologies of Medical Importance for the Diagnosis of Infectious Diseases and the Detection of Pathogenic Microbes*, Beijing, China, (2008).

Daum, L.T., et al., "Abstract—Quantitation of Influenza A Virus From Nasal and Lung Tissue of Cotton Rats Using Real-Time RT-PCR and Culture," *26th Annual Meeting of the European Society for Pediatric Infectious Diseases*, Graz, Austria, (2008).

Daum, L.T., et al., "Abstract—Development and Clinical Evaluation of Rapid Real-Time RT-PCR Assays for Detection of Influenza A and B Viruses," *26th Annual Meeting of the European Society for Pediatric Infectious Diseases*, Graz, Austria, (2008).

Daum, L.T., et al., "Poster—A Novel Specimen Collection Solution for Molecular Diagnostic Applications," *The Pediatric Academic Societies (PAS) Annual Meeting*, Honolulu, HI (2008).

Daum, L.T., et al., "Poster—Real-Time RT-PCR Detection of Influenza A Virus in Asymptomatic Culture-Negative Cotton Rats," *The Pediatric Academic Societies (PAS) Annual Meeting*, Honolulu, HI (2008).

Daum, L.T., et al., "Poster—Detection and Molecular Characterization of Clinical Influenza A and B Viruses from Original Nasal Wash Specimens Preserved in PrimeStore™," *The 3rd European Conference on Influenza*, Vilamoura, Portugal (2008).

Daum, L.T., et al., "Real-Time RT-PCR Detection of Influenza Virus Within Symptomatic and Asymptomatic Family Members," *The 48th Annual IDSA/ICAAC*, Washington D.C. (2008).

European Patent Office, "PCT Notification of Transmittal of the International Search Report and the Written Opinion of the International Searching Authority or the Declaration, PCT International Search Report, PCT Written Opinion of the International Searching Authority—Application No. PCT/US2007/078025," Nov. 13, 2008, 10 pages.

"Abstracts—27th Annual Meeting of the European Society for Paediatric Infectious Disease, Brussels, Belgium, Jun. 9-13, 2009," *The Ped. Infect. Dis. J.*, 28(6):e1, e75, e202, e229 (Jun. 2009).

Borns, M. et al, "Most Accurate PCR Enzyme Inproved With Hot Start Feature," Biocompare, available at http ://www.biocompare.com/technicalarticle/212/Most-Accurate-PCR-Enzyme-Improved-With-Hot-Start-Feature-from-Stratagene.html (last visited Aug. 24, 2009).

"KOD Hot Start DNA Polymerase," Novagen, available at http://www.emdbiosciences.com/Products/ProductDisplay.asp?catno=71086 (last visited Aug. 24, 2009).

"R.A.P.I.D® System," Idaho Technology Inc., available at http://www.idahotech.com/RAPID/Rapid-Water.html (last visited Aug. 24, 2009).

"AgPath-ID™ One-Step RT-PCR Kit," Applied Biosystems, available at http://www.abion.com/techlib/prot/bp_1005.pdf (last visited Aug. 24, 2009).

"PCR Optimization: Reaction Conditions and Components," Applied Biosystems, Part No. 4371091, Revision C, pp. 1-6 available at http://www3.appliedbiosystems.com/ems/groups/mcb_marketing/documents/generaldocuments/ems_042520.pdf (last visited Aug. 24, 2009).

"Single Tube PCR Kit Manual," Takara Bio Inc., Cat. #RR021, V.02.09, pp. 1-6 available at http://www.takara-bio.us/files/manuals/TAK_RR021_TM.pdf (last visited Aug. 24, 2009).

"Luminex Confirms Effectiveness of xTAG® Respiratory Viral Panel for Swine Flu Surveillance," *Medical News Today*, available at http://www.medicalnewstoday.com/printerfriendlynews.php?newsid=148498 (May 1, 2009).

"Luminex Receives FDA Clearance for an Update to the xTAG® Respiratory Viral Panel Package Insert Package Insert to Include Data from Two New Publications on 2009 Influenza A/H1N1," available at http://phx.corporate-ir.net/phoenix.zhtml?c=79403&p=irol-newsArticle&ID=1307416&highlight= (Jul. 14, 2009).

IL Exam Report for PCT/US2007/078025, dated Mar. 7, 2013.

EPO Exam Report for EP12180376, dated Feb. 8, 2013.

Canadian Office Action for application No. 2759028, dated Apr. 12, 2013.

Henke et al., "Betaine Improves the PCR Amplification of GC-Rich DNA Sequences," Nucleic Acids Research 25(19): 3957-3958 (1997).

Yue et al., "Detection of rifampin-resistant Mycobacterium tuberculosis strains by using a specialized oligonucleotide microarray," Diagnostic Microbiology and Infectious Disease, 48(1): 47-54 (2004).

CA Office action for PCT/US08/78499, dated Mar. 29, 2012.

Canadian Office Action for application No. 2697373, dated Feb. 19, 2013.

PCT Search Report for PCT/US13/32354, dated May 31, 2013.

Chinese Office Action for Application No. 201080028416.4, (2010).

Chinese Search Report for Application No. 201080028416.4, (2010).

Austalian Exam Report for Application No. 2012239385, dated Oct. 9, 2013.

Austalian Exam Report for Application No. 2012211365, dated Oct. 9, 2013.

Max, et al Reliability of PCR-based detection of occult tumour cells: lessons from real-time RT-PCR, (2001).

EP Search Report for Application No. 13175959, dated Nov. 18, 2013.

PCT Search and Patentability Report for PCT/US2013/077038, dated Mar. 10, 2014.

CA Office Action for CA Application No. 2701168, dated Mar. 4, 2014.

CA Office action for PCT/US2007/078025, dated Jan. 4, 2011.

(56) References Cited

OTHER PUBLICATIONS

EPO Exam Report for PCT/US2007/078025, dated Dec. 30, 2011.
EPO Exam Report for PCT/US2007/078025, dated Aug. 26, 2010.
EPO Exam Report for PCT/US2007/078025, dated Jul. 6, 2009.
EPO Exam Report for PCT/US2007/078025, dated May 18, 2009.
AU Exam Report for PCT/US2007/078025, dated Nov. 19, 2010.
IL Exam Report for PCT/US2007/078025, dated Mar. 16, 2011.
NZ Exam Report for PCT/US2007/078025, dated Jul. 7, 2010.
Israel Office Action of Jul. 19, 2012.
EPO Supplementary Search Report for PCT/US10/31761, dated Jul. 13, 2012.
PCT Written Opinion for PCT/US2008/078499, dated Jul. 4, 2010.
"Monolithic Silica Extraction Tips for Sample Preparation," CP-Analytica, available at http://cp-analytica (last visited Oct. 25, 2010).
Barnard, et al., "Suitability of new chlamydia transport medium for transport of herpes simplex virus," J. of Clin. Microbiol., 24(5): 692-695 (1986).
Eroglu, et al., "Successful cyropreservation of mouse oocytes by using low concentrations of trehalose and dimethylsylfoxide," Biol. of Rep. 80:70-78 (2009).
Gelmi, et al., "Bacertial survival in different transport media," European Congress of Clinical Microbiology and Infectious Diseases (ECCMID), May 28-31, 2000 (poster).
Higashiyama, T., "Novel functions and applications of terhalose," Pure Appl. Chem. 74(7): 1263-1269 (2002).
H1N1 RTPCR Primer/Probe Sets, Intergrated DNA Technologies—H1N1, available at http://www.idtdna.com/catalog/h1n1/page1.aspx, (2010).
Johnson, F.B., "Transport of viral specimens," Clin. Microbiol. Rev. 3(2): 120-131 (1990).
Sponseller, et al., "Influenza A pandemic (H1N1) 2009 virus infection in domestic cat," Emerg. Infect. Dis. (e-publication) (2010).
PCT Patentability Report for PCT/US2010/043546, dated Jan. 31, 2012.
PCT Search Report and Patentability Report for PCT/US2008/074521, dated Mar. 2, 2010.
Buck et al. BioTechniques vol. 27, pp. 528-536, Sep. 1999.
Characterization of Novel Influenza 2005.
Daum, et al., Abstract and Poster—"Development of a Real Time Reverse-Transcription PCR (RRT-PCR) Assay for Detection of Influenza A H1N1 2009 from Clinical Respiratory Specimens," Pediatric Infectious Disease Conference ESPID, Nice, France, May 5-8, 2010.
De Silva at al. Influenza A virus (A/Nonthaburi/102/2009(H1N1)) segment 4 hemagglutinin (HA) gene, partial cds. Genbank Accession No. GQ 132184.1, submitted May 9, 2009.
Hindiyeh et al. Journal of Clinical Microbiology, vol. 43, No. 2, pp. 589-595, Feb. 2005.
"Adamantane Resistance Among Influenza, etc.", JAMA, Feb. 22, 2006, vol. 295, No. 8, pp. 891-894.
Lowe et al. A computer program for selection of oligonucleotide primers for polymerase chain reactions. Nucleic Acids Research (1990) vol. 18, No. 7, pp. 1757-1761.
Luke T. Daum et al., "Detection and Molecular Characterization of Clinical Influenza A and B Viruses from Original Nasal Wash Specimens Preserved in PrimeStore," (2008).
Denhart, M., and Doraiswamy, V., "Master Your PCR Domain!" Promega Notes, 78: 9-12 (2001).
Master Your PCR Domain.
http://www.ncbi.nim.nih.gov/genomes/FLU/SwineF1u2009.html.
NCBI Influenza Virus Resource "CLE I. GenBank Sequence from Pandemic (H1N1) 2009 Viruses". 1237 pages.
Pamphlet—"Prime PCR System"—Longhorn Vaccines & Disagnostics, (2010).
Magari, R.T., Assessing shelf life using real-time and accelerated stability tests, BioPharm Nov. 2003.
"Taq PCR Master Mix (2x)," USB Corp., (2007).
"Immunoflourescence and Fluorescent-Antibody Techniques", Tortora, et al., Microbiology—An Introduction, Fourth Edition, 1992, pp. 461-463.

World Health Organization, "CDC protocol of realtime RTPCR for influenza A (H1N1)," Apr. 28, 2009.
Wiecek, A., "Pocket PCR: The Whole Chain Reaction in His Hand," Biotechniques.com, Oct. 26, 2010.
Danila Valmori et al. "Use of human universally antigenic tetanus toxin T cell epitopes as carriers for human vaccination" Journal of Immunology Jul. 15, 1992.
PCT Search Report for PCT/US2008/074521 dated Feb. 13, 2009.
PCT Written Opinion for PCT/US2008/074521 dated May 3, 2009.
PCT Search Report for PCT/US10/43546 dated Nov. 16, 2010.
De Folette et al. Vaccine 2006, Jun. 12, vol. 24, No. 44-46, pp. 6597-6601.
Galarza et al. Viral Immunity 2005, vol. 18, No. 2, pp. 365-372.
Arend et al. Infection and Immunity, 2000, vol. 68, No. 6, pp. 3314-3321.
Geysen, et al., "Use of Peptide Synthesis to Probe Viral Antigens for Epitopes to a Resolution of a Single Amino Acid," Proc. Natl. Acad. Sci., 81, pp. 3998-4002 (1984).
Tolman, et al., "Cyclic V3-Loop Related HIV-1 Conjugate Vaccines," Int. J. Peptide Protein Res., 41, pp. 455-466 (1993).
Conley, et al., "Immunogenicity of Synthetic HIV-1 Gp120 V3-Loop Peptide-Conjugate Immunogens," Vaccine, 12(5), pp. 445-451 (1994).
Schneider, et al., "Induction of CD8+T Cells Using Heterologous Prime-Boost Immunisation Strategies," Immunol. Rev., 170, pp. 29-38 (1999).
Tanghe, et al., "Improved Immunogenicity and Protective Efficacy of a Tuberculosis DNA Vaccine Encoding Ag85 by Protein Boosting," Infect and Immun., 69(5), pp. 3041-3047 (2001).
Gonzalo, et al., "A Heterologous Prime-Boost Regime Using DNA and Recombinant Vaccinia Virus Expressing the Leishmania infantum P36/LACK Antigen Protects BALB/c Mice from Cutaneous Leishmaniasis," Vaccine, 20, pp. 1226-1231 (2002).
Meyer, et al., "Complement-Mediated Enhancement of Antibody Function for Neutralization of Pseudotype Virus Containing Hepatitis C Virus E2 Chimeric Glycoprotein," J. of Virol., 76(5) pp. 2150-2158 (2002).
Robinson, "New Hope for an AIDS Vaccine," Nat. Rev. Immunol., 2, pp. 239-250 (Apr. 2002).
Lu, et al., "Multiepitope Trojan Antigen Peptide Vaccines for the Induction of Antitumor CTL and Th Immune Responses," J. of Immunol., 172, pp. 4575-4582 (2004).
Westerfield, et al., "Peptides Delivered by Immunostimulating Reconsituted Influenza Virosomes," J. of Peptide Sci., 11(11), pp. 707-712 (2005).
Gerhard, et al., "Prospects for Universal Influenza Virus," Emerging Infectious Diseases, 12(4), pp. 569-574 (Apr. 2006).
Luo, "Structural Biology: Antiviral Drugs Fit for a Purpose," Nature, 443, pp. 37-38 (Sep. 1, 2006).
PepTcell Ltd., "Technology," http://www.peptcell.com/technology.aspx (2007).
Stoloff, et al., "Synthetic Multi-Epitope Peptides Idenitifed in Silico Induce Protective Immunity Against Multiple Influenza Serotypes," Eur. J. of Immunol., 37(9), pp. 2441-2449 (Aug. 2, 2007).
Depla, et al., "Rational Design of a Multiepitope Vaccine Encoding T-Lymphocyte Epitopes for Treatment of Chronic Hepatitis B Virus Infections, " J. of Virol., 82(1), pp. 435-450 (Jan. 2008).
Chien et al. J. Clin. Microbiol. 1999, vol. 37, No. 5, 1393-1397.
Ishioka et al. J. Immunol. vol. 162, pp. 3915-3925 (1999).
Lederman et al. Molecular Immunology 1991, vol. 28, No. 11, pp. 1171-1181.
PCT Search Report for PCT/US2007/078025 dated Oct. 28, 2008.
PCT Written Opinion for PCT/US2007/078025 dated Mar. 17, 2009.
PCT Search Report for PCT/US2008/078499 dated Jul. 23, 2009.
"Collecting, Preserving, Shipping Specimens for the Diagnosis of Avian Influenza (H5N1) Virus Infection: Guide for Field Operations," WHO/CDS/EPR/ARO/2006.1 (2006).
Jamie A. Blow et al., "Viral nucleic acid stabilization by RNA extraction reagent," Journal of Virological Methods, 150 (2008), Feb. 4, 2008, pp. 41-44.
Kutyavin et al. 3'—Minor groove binder—DNA probes increase sequence specificity at PCR extension temperatures. Nucleic Acid Res. (2000) vol. 28, No. 2, pp. 655-661.

(56) References Cited

OTHER PUBLICATIONS

Canas, L.C., "Clinical Laboratory: Selection, Collection and Transport of Specimens for Viral Cultures." Department of the Air Force, Air Force Institute of Operational Health (AFIOH), Epidemiological Surveillance Division, SDE OI 44/5001, Virol. Proc. Man., 1-8 (2005).

Luke T. Daum et al., "Portugal Meeting Poster (Introduction, Materials, and Methods, Results, Discussion)," (2008).

Miyazaki, et al., "Development of a monolithic silica extraction top for the analysis of proteins," J. Chromatogr. A., 1043(1): 19-25 (2004) [abstract only].

Anderson, et al, "DNA and RNA-derived assessments of fungal community composition in soil amended with sewage sludge rich in cadmium, copper and zinc," Soil Biology and Biochemistry, Pegamon, Oxford, GB, vol. 40, No. 9, Sep. 1, 2008.

Liao, J et al, "Telomerase activity in oral and maaxillofacial tumors," Oral Oncology, Elsevier Science, Oxford, GB, vol. 36, No. 4, Jul. 1, 2000.

Daum, L, et al, "A clinical specimen collection and transport medium for molecular diagnostic and genomic applications," Epidemiology and Infection, Cambridge University Press, Cambridge, GB, vol. 139, No. 11, Dec. 16, 2010.

Daum, L. et al, "A rapid, collection-to-detection PCR system of the universal detection of mycobacterium tuberculosis," Jun. 29, 2011, pp. 1-1.

Papagrigorakis, M. et al, "DNA examination of ancient dental pulp incriminates typhoid fever as a probable cause of the plague of Athens," International Journal of Infectious Diseases, Hamilton, CA, vol. 10, No. 3, May 1, 2006.

Buys, et al, "Applying AFLPs in Aizoaceae: the Delosperma herbeum complex as a case study," Biochemical Systematics and Ecology, Pergamon Press, GB, vol. 36, No. 2, Dec. 13, 2007.

* cited by examiner

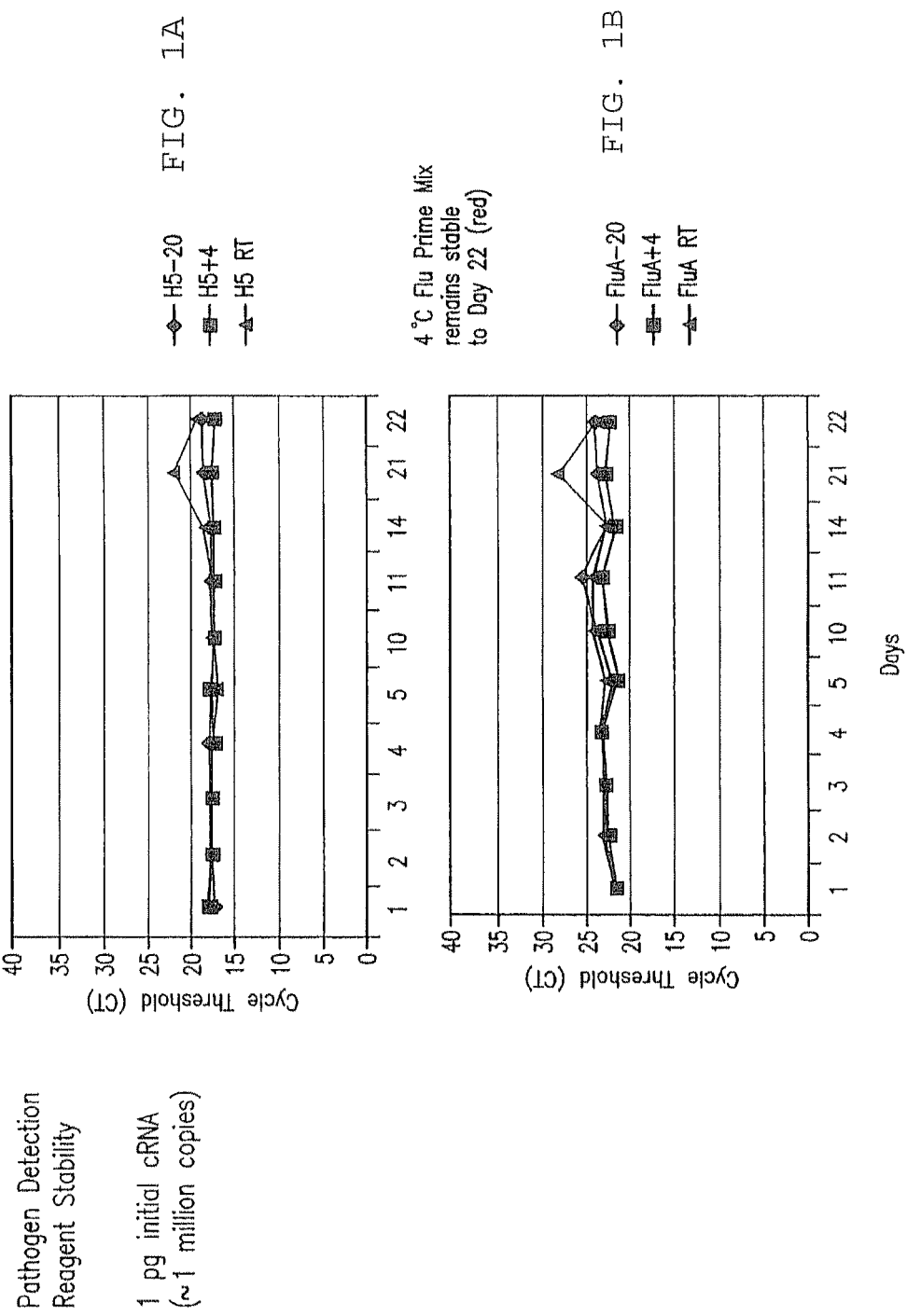

| | | |
|---|---|---|
| A/Anhui/1/2005 | GACTACCCCACTATTCAGAGAA (Table 1)

Primer/probe sequences[1] used for real-time RT-PCR amplification and *in vitro* generation of cRNA target templates

Real-time RT-PCR

| Primer | Sequence | Gene Target-Nucleotide position[1] | Amplicon |
|---|---|---|---|
| Type A | | Matrix (Segment 7) | 195 bp |
| Forward | taaccgaggtcgaaacgta (SEQ.ID. NO. 1) | 36 → 54 | |
| Reverse | gcacggtgagcgtgaa (SEQ.ID. NO. 2) | 215 → 230 | |
| Probe | (FAM)-tcaggcccctcaaagc (SEQ.ID. NO. 3) | 74 → 90 | |
| Type B | | Matrix (Segment 7) | 119 bp |
| Forward | ggaattgcaaaggatgtaatggaa (SEQ.ID. NO. 4) | 673 → 696 | |
| Reverse | agaacaaattgaaagaatctgaaatggt (SEQ.ID. NO. 5) | 764 → 791 | |
| Probe | (FAM)-atgggaaattcagctct (SEQ.ID. NO. 6) | 721 → 731 | |
| Subtype H1 | | H1 Hemagglutinin (Segment 4) | 89 bp |
| Forward | agycttcctttccagaatgtaca (SEQ.ID. NO. 7) | 948 → 970 | |
| Reverse | agtcctgtarccatycttaattttg (SEQ.ID. NO. 8) | 1012 → 1036 | |
| Probe (Table 2)
Detection of influenza virus type (A/B) strains

| Subtype | Strain | Flu A Univ. | Flu B Univ. |
|---|---|---|---|
| H1N1 | DK/NJ/7717-70/95 | + | - |
| H1N1 | CK/NY/21665-73/98 | + | - |
| H2N2 | CK/NY/3749-7/96 | + | - |
| H2N4 | DK/LA/8174/86 | + | - |
| H3N8 | ENV/NY/19019-6/98 | + | - |
| H4N6 | DK/CZECH/56 | + | - |
| H4N8 | DK/ALB/286/78 | + | - |
| H5N1 | TK/ENG/50-92/91 | + | - |
| H5N1 | CK/SCTT/59 | + | - |
| H5N1 | MA/OH/184/86 | + | - |
| H5N1 | A/SE Asia/2003 | + | - |
| H5N2 | CK/MA/11801/86 | + | - |
| H5N2 | CK/PUE/8624-602/94 | + | - |
| H5N2 | PH/NJ/1355/95 | + | - |
| H5N3 | DK/SING/97 | + | - |
| H5N3 | TK/CA/6878/79 | + | - |
| H5N8 | TK/IR/83 | + | - |
| H5N9 | RATITE/NY/12716/84 | + | - |
| H6N2 | CK/NY/14677-13/99 | + | - |
| H7N1 | SB/IL/35445-136/92 | + | - |
| H7N1 | TK/IT/4580/99 | + | - |
| H7N2 | CK/PA/13552-1/98 | + | - |
| H7N2 | EQ/NY/13142-5/94 | + | - |
| H7N2 | TK/PA/7975/97 | + | - |
| H7N3 | CK/PAK/13692/95 | + | - |
| H7N3 | MA/NETHERLANDS/12/00 | + | - |
| H7N3 | Q/AR/16309-2/94 | + | - |
| H7N4 | CK/NSW/1688/97 | + | - |
| H7N7 | CK/VIC/85 | + | - |
| H7N7 | EQ/PRAGUE/E5302/56 | + | - |
| H8N4 | TK/ONT/6188/67 | + | - |
| H8N8 | DK/VIC/8211-18-1400/92 | + | - |
| H9N2 | A/CK/HK/G9/97 | + | - |
| H9N2 | CK/KOREA/96006/96 | + | - |
| H9N2 | CK/NJ/12220/97 | + | - |
| H10N7 | TK/VA/31409/91 | + | - |
| H10N7 | CI/GER/N/49 | + | - |
| H11N1 | DK/ENG/56 | + | - |
| H11N1 | CK/NJ/15906-6/96 | + | - |
| H12N5 | DK/LA/18813/87 | + | - |
| H12N5 | DK/ALB/60/76 | + | - |
| H13N6 | GULL/6411/MD/704/77 | + | - |
| H14N5 | MA/GURJEV/263/82 | + | - |
| H15N9 | SW/AUSTR/2576/79 | + | - |
| H16N3 | A/BHG/SWEDEN/2/99 | + | - |
| B/Yam | B/Arizona/135/2005 | - | + |
| B/Vic | B/Arizona/140/2005 | - | + |
| B/Vic | B/Nepal/1120/2005 | - | + |
| B/Yam | B/Florida/2004 | - | + |
| B/Vic | B/Hawaii/22/2004 | - | + |
| B/Vic | B/Brisbane/32/2002 | - | + |

[1] Determined by type A and B specific assays.
B/Yam = Type B Yamagata lineage; B/Vic = Type B Victoria lineage

FIG. 6

(Table 3)

Detection of influenza virus types (A/B) and subtypes (H1, H3, and H5) in cultured clinical isolates by real-time RT-PCR

| Location (samples) | [1]Flu A/B | [2]H1 | [2]H3 | [2]H5 | [3]Flu A/B |
|---|---|---|---|---|---|
| United States | | | | | |
| Alabama (2) | 2/0 | 0 | 2 | 0 | 2/0 |
| Alaska (4) | 3/1 | 0 | 3 | 0 | 3/1 |
| Arizona (9) | 7/2 | 0 | 7 | 0 | 7/2 |
| California (4) | 4/0 | 0 | 4 | 0 | 4/0 |
| Colorado (23) | 22/1 | 0 | 22 | 0 | 22/1 |
| Connecticut (1) | 1/0 | 0 | 1 | 0 | 1/0 |
| District of Columbia (4)[4] | 1/1 | 0 | 1 | 0 | 1/1 |
| Hawaii (11) | 9/2 | 0 | 9 | 0 | 9/2 |
| Illinois (4) | 4/0 | 0 | 4 | 0 | 4/0 |
| Maryland (6) | 6/0 | 0 | 6 | 0 | 6/0 |
| New Jersey (3) | 3/0 | 0 | 3 | 0 | 3/0 |
| New York (1) | 1/0 | 0 | 1 | 0 | 1/0 |
| Oklahoma (5) | 5/0 | 0 | 5 | 0 | 5/0 |
| Texas (24) | 24/0 | 0 | 24 | 0 | 24/0 |
| Virginia (2) | 2/0 | 0 | 2 | 0 | 2/0 |
| Country | | | | | |
| Ecuador (1) | 1/0 | 0 | 1 | 0 | 1/0 |
| England (7) | 4/3 | 1 | 3 | 0 | 4/3 |
| Guam (2) | 2/0 | 1 | 1 | 0 | 2/0 |
| Iraq (1) | 1/0 | 0 | 1 | 0 | 1/0 |
| Italy (1) | 1/0 | 0 | 1 | 0 | 1/0 |
| Japan (21) | 19/2 | 1 | 18 | 0 | 19/2 |
| Ketchikan (1) | 1/0 | 0 | 1 | 0 | 1/0 |
| Kenya (2) | 1/1 | 1 | 0 | 0 | 1/1 |
| Korea (12) | 12/0 | 5 | 7 | 0 | 12/0 |
| Kuwait (3) | 2/1 | 1 | 1 | 0 | 2/1 |
| Peru (21) | 19/2 | 0 | 19 | 0 | 19/2 |
| Qatar (4) | 4/0 | 1 | 3 | 0 | 4/0 |
| Turkey (1) | 1/0 | 0 | 1 | 0 | 1/0 |
| Total Samples = 180 | 162/16 | 11 | 151 | 0 | 162/16 |

[1] Determined by type A and B specific assays.
[2] Determined by subtype (H1, H2, and H3) specific assays.
[3] Determined by traditional 'gold standard' virus isolation/identification.
[4] Two of 4 District of Columbia samples tested negative for influenza virus using type/subtype specific assays reported here and were subsequently confirmed as being influenza negative by traditional 'gold standard' virus isolation/identification.

FIG. 7

(Table 4)

Detection of influenza virus types (A/B) and subtypes (H1, H3, and H5) in uncultured primary clinical specimens by real-time RT-PCR

| Location (samples) | [1]Flu A/B | [2]H1 | [2]H3 | [2]H5 | [3]Flu A/B |
|---|---|---|---|---|---|
| United States | | | | | |
| Alabama (1) | 0/1 | 0 | 0 | 0 | 0/1 |
| Arkansas (4) | 4/0 | 3 | 1 | 0 | 4/0 |
| California (1) | 1/0 | 0 | 1 | 0 | 1/0 |
| Delaware (1) | 1/0 | 0 | 1 | 0 | 1/0 |
| District of Columbia (2) | 0/2 | 0 | 0 | 0 | 0/2 |
| Georgia (2) | 2/0 | 0 | 2 | 0 | 2/0 |
| Hawaii (14)†(4) | 14/0 | 1 | 13 | 0 | 14/0 |
| Mississippi (1)†(1) | 1/0 | 0 | 1 | 0 | 1/0 |
| New Jersey (2) | 2/0 | 1 | 1 | 0 | 2/0 |
| New Mexico (2) | 0/2 | 0 | 0 | 0 | 0/2 |
| Oklahoma (1) | 1/0 | 0 | 1 | 0 | 1/0 |
| South Carolina (1) | 1/0 | 0 | 1 | 0 | 1/0 |
| Texas (3)[4] | 1/1 | 1 | 0 | 0 | 1/1 |
| Virginia (16) | 1/15 | 0 | 1 | 0 | 1/15 |
| Washington (1) | 1/0 | 0 | 1 | 0 | 1/0 |
| Country | | | | | |
| Guam (2)†(2) | 2/0 | 0 | 2 | 0 | 2/0 |
| Iraq (1) | 1/0 | 0 | 1 | 0 | 1/0 |
| Italy (2) | 1/1 | 0 | 1 | 0 | 1/1 |
| Japan (5)†(2) | 3/2 | 2 | 1 | 0 | 3/2 |
| Kenya (2) | 1/1 | 0 | 1 | 0 | 1/1 |
| Korea (5)†(2) | 5/0 | 1 | 4 | 0 | 5/0 |
| Kuwait (1) | 1/0 | 1 | 0 | 0 | 1/0 |
| Nepal (69)[4],†(1) | 1/2 | 0 | 1 | 0 | 1/2 |
| Okinawa (1) | 1/0 | 0 | 1 | 0 | 1/0 |
| Peru (8) | 4/4 | 1 | 3 | 0 | 4/4 |
| Qatar (2) | 2/0 | 1 | 1 | 0 | 2/0 |
| Thailand (13)†(2) | 4/9 | 0 | 4 | 0 | 4/9 |
| Turkey (2)†(2) | 2/0 | 0 | 2 | 0 | 2/0 |
| United Kingdom (2) | 2/0 | 0 | 2 | 0 | 2/0 |
| Total Samples = 167 | 60†(16)/40 | 12 | 48 | 0 | 60/40 |

[1] Determined by type A and B' specific assays.
[2] Determined by subtype (H1, H2, and H3) specific assays.
[3] Determined by traditional 'gold standard' virus isolation/identification.
[4] One of 3 Texas samples and 66 of 69 Nepal samples tested negative for influenza virus using type/subtype specific assays reported here and were all subsequently confirmed as being influenza negative by traditional 'gold standard' virus isolation/identification.
† Primary uncultured samples requiring culturing for identification. The number of samples is indicated in the parenthesis.

FIG. 8

TABLE 5

PRIMER/PROBE SEQUENCES USED FOR REAL-TIME RT-PCR AMPLIFICATION

OF INFLUENZA A H1N1 (SWINE FLU 2009)

| *Primer/ Probe* | *Sequence* | *Gene Target Nucleotide position* | *Amplicon* |
|---|---|---|---|
| | | H1 Hemagglutinin (Segment 4) | 89-bp |
| Forward Primer | 5′-AGCCTYCCATTTCAGAATATACA-3′ (SEQ ID NO:51) | 916 → 938 | |
| Reverse Primer | 5′-AATCCTGTRGCCAGTCTCAATTTTG-3′ (SEQ ID NO:52) | 980 → 1004 | |
| Probe | 5′-6(FAM)-TCCAAAATATGTAAAAAG-3′ (SEQ ID NO:53) | 960 → 977 | |

FIG. 9

COMPOSITIONS AND METHODS FOR RAPID, REAL-TIME DETECTION OF INFLUENZA A VIRUS (H1N1) SWINE 2009

CROSS-REFERENCE TO RELATED APPLICATIONS

The present application is a continuation of U.S. application Ser. No. 12/510,968, filed Jul. 28, 2009, now U.S. Pat. No. 8,097,419, a continuation-in-part of U.S. patent application Ser. No. 13/328,992 filed Dec. 16, 2011, now pending, which is a continuation of U.S. application Ser. No. 12/426,890, filed Apr. 20, 2009, now U.S. Pat. No. 8,060,645, a continuation-in-part of U.S. patent application Ser. No. 13/094,809 filed Apr. 26, 2011, now pending, a continuation-in-part of U.S. patent application Ser. No. 12/916,263 filed Oct. 20, 2010, now pending, a continuation-in-part of U.S. patent application Ser. No. 13/332,204 filed Dec. 20, 2011, which is a continuation of U.S. application Ser. No. 12/243,949 filed Oct. 1, 2008, now U.S. Pat. No. 8,084,443, and a continuation-in-part of U.S. patent application Ser. No. 11/844,933, filed Aug. 24, 2007, now pending, and claims the benefit of U.S. Provisional Application No. 60/976,728, filed Oct. 1, 2007, and U.S. Provisional Application No. 60/843,711, filed Sep. 12, 2006, the entire contents of each of which is specifically incorporated herein in its entirety by express reference thereto.

FIELD OF THE INVENTION

The invention relates to a biological organism detection product and methods of using the same to: 1) rapidly identify and detect; 2) determine virulence; 3) determine drug resistance and other resistance markers from collected organisms; or a combination thereof. In particular embodiments, the invention provides compositions and methods for identifying, quantitating, and detecting influenza virus-specific nucleic acid segments within a population of polynucleotides obtained from a biological sample. In illustrative examples, a method has been developed to quickly and accurately identify the presence of Influenza A H1N1 (Swine flu 2009) viral strains in such a sample.

BACKGROUND

Numerous pathogens (e.g., viruses, bacteria, fungi, and parasites) cause infection and other illness in animal and human populations worldwide. Sometimes one or more mutations in a pathogen can cause a typical illness-causing pathogen to become a full-blown pandemic. Although these pathogens and resultant illnesses are varied, one of the more prominent based on current events is the influenza virus.

The influenza virus and its variations (collectively referred to herein as "the flu virus") are the cause for a contagious respiratory illness (commonly referred to as "influenza," "illness," or the "Flu") in humans and animals (interchangeably referred to herein as a "host," "patient," or "subject") that can cause mild to severe illness, and at times can lead to death. Every year in the United States alone, on average: 5% to 20% of the population gets the Flu; more than 200,000 people are hospitalized from Flu complications—and about 36,000 people die from Flu.

The flu virus spreads in respiratory droplets typically transmitted through coughing and sneezing. In human patients, the virus usually spreads from person to person, though sometimes subjects become infected by touching something with flu viruses on it and then touching their mouth or nose. Most healthy adults may be able to infect others beginning 1 day before symptoms develop and up to 5 days after becoming sick. Uncomplicated influenza illness is often characterized by an abrupt onset of constitutional and respiratory signs and symptoms, including fever, myalgia, headache, malaise, non-productive cough, sore throat, and rhinitis.

There are three main types of influenza viruses: influenza A, influenza B, and influenza C. Within each type of influenza and within influenza A in particular there are many different subtypes. These subtypes differ based upon certain proteins expressed on the surface of the virus, specifically the hemagglutinin (HA) and the neuraminidase (NA) proteins. To date sixteen HA subtypes and nine NA subtypes of influenza A virus have been reported from avian isolates. Many different combinations of HA and NA proteins are possible, however, and each combination represents a unique subtype.

"Human influenza virus" usually refers to those subtypes that spread widely among humans. There are three known influenza A subtypes currently circulating among humans: H1N1, H1N2, and H3N2, each of which include various individual influenza viral strains. Subtype H2N2, for example, (which includes strains often referred as 'Asian Flu' strains), circulated within the human population from 1957-1968. Subtype H1N1, which includes strains commonly referred to as 'Swine Flu' strains, is currently circulating within various human populations worldwide.

Alarmingly, because influenza A viruses can constantly undergo mutations, reassortments, genetic "drift and shift," and the like, host specificities are changing. Influenza viruses can be spread among various animal species, and infection from non-human species (such as avians, porcines, primates, and other animals) to human hosts leads to new influenza subtypes that can adapt over time to infect and spread more rapidly or thoroughly among human populations. Examples that have been widely reported in recent years include, for example, H5, H7, and H9 subtypes.

The H5N1 subtype, for example, has been reported as having mutated sufficiently to spread from avian hosts to humans. While the spread of H5N1 virus from human to human has, at least for now, been limited, unfortunately that has not been the case with the spread of particular strains of the H1N1 subtype, which appear to be highly contagious, and infectious when spread from person to person. Additionally, because H5N1, H1N1, and many other subtypes have been historically less prevalent in human populations, there is little or no immune protection against them in humans at present. Indeed, it has been widely reported in the mainstream media, and commonly considered in the scientific community that, if virulent strains of Influenza A virus were to gain the capacity to spread easily from person to person, a worldwide outbreak of disease (i.e., pandemic) would likely ensue. The midsummer 2009 declaration by the World Health Organization (WHO) that the spread of H1N1 influenza had reached Phase 6 pandemic proportion (nearly 100,000 laboratory-confirmed cases and over 400 deaths) in more than 120 countries, confirms this conventional wisdom.

Pandemic viruses typically emerge as a result of a process called "antigenic shift," which causes an abrupt or sudden, major change in a virus, e.g., influenza A virus. In the process of antigenic shift, two or more different strains of a single virus (or of different viruses), combine to form a distinctly new subtype that expresses a unique combination of surface antigens found in the strains that originally combined. While antigenic shift has been reported in various viral species, it is most widely observed in influenza virus, thus representing the most common form of genetic reassortments that gives rise to a phenotypic change in the resultant strains.

With influenza, these changes are caused by influenza A viruses spread from birds and animals to humans, thereby creating new combinations of the HA and/or NA proteins on the surface of the virus. Such changes result in a new influenza A virus subtype. The appearance of a new influenza A virus subtype is the first step toward a pandemic. To cause a pandemic, however, the new virus subtype also would need the capacity to spread easily from person to person and be a subtype that is sufficiently dissimilar from the two typical strains (A and B) found in the human population. Once a new pandemic influenza virus emerges and spreads, it eventually becomes established and transmissible among human populations, circulating for many years as part of the seasonal epidemics of influenza.

While the extent and severity of a pandemic cannot be accurately predicted, several computer modeling studies suggest that the impact of a pandemic on the United States (and the world as a whole) could be substantial. In the absence of any control measures (e.g., vaccination or drugs), it has been estimated that a "medium-level" pandemic in the U.S. could cause 89,000 to 207,000 deaths, 314,000 to 734,000 hospitalizations, 18 to 42 million outpatient visits, and another 20 to 47 million incidents of illness. According to the Centers for Disease Control and Prevention (CDC), between 15% and 35% of the U.S. population could be affected by an influenza pandemic, with an economic impact estimated between approximately $70 and $170 billion. By summer 2009, CDC had reported more than 43,000 confirmed and probable cases of H1N1 in the U.S., with more than 300 of those resulting in death.

Biological organisms (also interchangeably referred to herein as "organisms" or "microorganisms"), such as bacteria and viruses, like influenza A, B, or a combination of organisms, and particularly pandemic influenza, threaten to quickly spread over large geographic ranges and through large populations, causing high rates of mortality and morbidity. Prior to mobilizing and implementing prevention tactics to ensure public health, it is critical to first and foremost detect and identify these organisms as soon as they appear. Early detection and surveillance to track the spread of such organisms might help mitigate the extensive damage predicted by the CDC in the event of a pandemic outbreak, e.g., influenza. Early detection is also expected to be critical in limiting or helping to treat the damage from any biological terrorism. Thus, a system to rapidly detect and identify organisms is most desirable.

Conventional techniques to detect and identify viruses, however, are not suitable for this task. Generally virus surveillance, detection and identification are time consuming (e.g., days to weeks, and in some cases, months), cumbersome to conduct, and have the potential of posing numerous health risks to health care personnel and even the general public. Most techniques typically require cold chain cultures (with safety level 3 to 4 protocols), which is associated with fairly high levels of risk. The conventional surveillance, detection, and identification process (collectively referred to herein as "the surveillance process") typically includes culturing a live target specimen (interchangeably referred to herein as "targeted specimen," "tissue," or "sample"), such as bird, swine, human, or other living cells; transporting the sample to a suitable laboratory facility or other testing site, such as national, regional, or state testing laboratories; and then testing the target specimen for a range of biological organisms. Based on assays of genomic material (e.g., RNA and/or DNA) in the target sample, the organism(s) can often be identified.

Inherent in this identification and detection process is the need for bringing the target specimen back to a laboratory, thereby adding time and risk to the entire process. If the target specimen is found remotely, then it must be carefully transported to a suitable diagnostic laboratory so as to not harm, contaminate, or risk accidental exposure of the specimen or of the people handling the specimen during transport. During transportation, for example, the specimen is typically kept in a refrigerated or near frozen condition to ensure that the specimen is kept alive and the tissues to be tested remain intact.

Thus, Applicants have discovered a need in the art for a simple to use, stable, rapid diagnostic tool and product that, rather than culturing an organism and/or sending the specimen to a remote laboratory, would allow more rapid detection and identification of biological organisms, such as microorganisms (e.g., viruses and bacteria), at or adjacent a specimen collection site. The diagnostic tool should be portable and capable of being operated remotely from a conventional laboratory, and preferably would provide safety in such an environment compared to conventional diagnostic methods used in regional facilities, such as culturing such organisms.

SUMMARY OF THE INVENTION

The present invention meets unmet needs in the art by providing an inventive diagnostic product (also interchangeably referred to herein as a "biological organism identification product" and a "diagnostic tool"), and methods of using the same, to rapidly detect and identify microorganisms. In particular applications the diagnostic product permits the collection of a target specimen, preparation of the target specimen for assaying, isolation of genomic material, and subsequent processing of the genomic material to identify the organism. Generally, the diagnostic tool can be used in the field to collect one or more organisms and identify the collected organism(s), and provides a relatively immediate form of surveillance against potential epidemics, outbreaks, infections, and other biological organisms of interest.

Embodiments of the present invention encompass a biological organism identification product that includes a collection device to collect one or more sample organisms, a fixing and transporting composition present in an amount sufficient to kill one or more sample organisms associated with the collection device, an extraction member to extract a sufficient amount of genomic nucleic acid from one or more sample organisms to facilitate identification thereof, and a stabilized polymerase chain reaction (PCR) component into which the sufficient amount of genomic nucleic acid can be dissolved.

Preferred embodiments of the present invention include a durable, stand-alone biological organism product (referred to interchangeably herein as a "kit") that can conduct a plurality of field diagnoses. The kit may preferably include a portable enclosure to retain the product components including the collection device, fixing and transporting composition, extraction member, and a stabilized component. The kit may also include machinery to conduct the PCR and/or a power source or power adapted to operate any machinery. In certain embodiments, the diagnostic kit also includes a plurality of active pharmaceutical ingredient doses in an amount sufficient to prevent or treat one or more conditions caused by the identified biological organism.

The present invention, in certain embodiments, relates to methods of identifying a biological organism that includes collecting a biological sample from a subject, fixing the biological sample in a sufficient amount of a fixing agent to minimize or eliminate any contamination by the biological sample, extracting a sufficient amount of genomic nucleic acid from the fixed biological sample, and assaying the sufficient amount of the genomic nucleic acid in a lyophilized polymerase chain reaction component to obtain information about the organism. In preferred embodiments, the polymerase chain reaction component has a sufficient amount of one or more primers, which identify predetermined organisms and each of which is chemically associable to a protein component specific to a biological organism. Preferably, this all occurs in a single location.

In other embodiments, the method is relatively rapid compared to conventional organism detection techniques. In some embodiments of the method, no more than about 24 to 72 hours pass from the collecting of the target specimen to the assaying of the genomic material to obtain identification information. In some embodiments of the invention, the assaying is conducted for about 30 to 180 minutes, preferably 45 minutes to 150 minutes.

The invention also encompasses a reagent mix for detection of a microbial sequence, the reagent mix including one or more microbe-specific primers, probes, or enzymes, or a combination thereof, present in a mixture that is at least substantially stable at room temperature and is adapted and configured for use with a polymerase chain reaction (PCR) device. In one embodiment, the reagent mix is substantially stable at room temperature for at least about 5 days and up to two weeks. In another embodiment, the detection of the microbial sequence occurs within about 90 minutes after the microbial sequence is extracted from a sample. The reagent mix can be used to identify a microbial sequence, such as a pathogen, bacterial or viral sequence, or combination thereof. The reagent mix of the present invention, also referred to herein as a "prime mix," can also be used to identify strains of a viral or bacterial sequence, or even sub-strains of influenza.

In another embodiment, the reagent mix can be used as part of an apparatus to facilitate determination of a microbial amino acid sequence. In preferred embodiments of the invention, the reagent mix is particularly suited to field use, and can be used in conjunction with a collection device that collects one or more biological organism samples. In additional embodiments, identification of the same occurs within about 90 minutes.

A further embodiment of the invention includes a method for detection of a microbial sequence that includes obtaining genomic nucleic acid from a biological sample and assaying the genomic material by adding the nucleic acid to the reagent mix of one or more microbe-specific primers, probes, or enzymes, or a combination thereof, wherein the mix is substantially stable at room temperature and is adapted for use with a PCR device. In another embodiment, the PCR device includes fluorescence detection equipment for real-time PCR detection.

In one embodiment, the invention provides a method for detecting the presence or absence of an Influenza virus-specific nucleic acid segment, and in particular aspects, provides a method for detecting the presence or absence of a particular type, subtype, or strain of Influenza virus. In exemplary embodiments, the invention provides a method of identifying an Influenza A H1N1 subtype virus-specific nucleic acid segment in a population of polynucleotides that is preferably obtained from a biological sample.

In an overall and general sense the method includes performing at least one cycling step, wherein the cycling step includes at least a first amplifying and at least a first hybridizing, wherein the at least a first amplifying includes contacting the sample with a pair of Influenza A H1N1 subtype virus-specific amplification primers to produce an Influenza A H1N1 subtype virus-specific amplification product if an Influenza A H1N1 subtype virus-specific nucleic acid segment is present in the sample; and wherein the at least a first hybridizing is accomplished using a labeled detection probe that is specific for the amplification product, wherein the presence of the amplification product is indicative of the presence of one or more Influenza A H1N1-specific nucleic acid segments in the population of polynucleotides.

In particular aspects, the pair of amplification primers includes a first oligonucleotide primer of less than about 50, preferably less than about 40, and more preferably still, less than about 30 nucleotides in length that comprises, consists essentially of, or alternatively, consists of the nucleic acid sequence 5'-AGCCTYCCATTTCAGAATATACA-3' (SEQ ID NO:51).

Likewise, in certain aspects, the pair of amplification primers includes a second oligonucleotide primer of less than about 50, preferably less than about 40, and more preferably still, less than about 30 nucleotides in length that comprises, consists essentially of, or alternatively, consists of, the nucleic acid sequence 5'-AATCCTGTRGCCAGTCT-CAATTTTG-3' (SEQ ID NO:52).

In certain illustrative aspects, the presence of an amplification product so produced in an amplification of the subject population of polynucleotides (such as for example, by using PCR-based amplification methodologies) may be detected through the use of a labeled oligonucleotide probe that is specific for the amplification product so produced. In illustrative examples presented herein, the detection probe includes a first oligonucleotide probe of less than about 50 nucleotides in length, preferably of less than about 40 nucleotides in length, and more preferably still of less than about 30 nucleotides in length, and further wherein the detection probe includes a nucleic acid sequence that comprises, consists essentially of, or alternatively consists of the nucleic acid sequence of 5'-TCCAAAATATGTAAAAAG-3' (SEQ ID NO:53).

In a related embodiment, the method may be employed using a composition that includes (a) a pair of amplification primers includes: (i) a first oligonucleotide primer of less than about 50 nucleotides in length that includes the nucleic acid sequence of SEQ ID NO:51, and (ii) a second oligonucleotide primer of less than about 50 nucleotides in length that includes the nucleic acid sequence of SEQ ID NO:52; and (b) a first detection probe of less than about 50 nucleotides in length that specifically binds to the amplification product so produced, and that includes a nucleic acid sequence that comprises, consists essentially of, or alternatively consists of the sequence of SEQ ID NO:53.

In the practice of the invention, the population of polynucleotides so analyzed will preferably be obtained from a biological sample, with biological samples obtained from a mammal (including e.g., humans, non-human primates, domesticated livestock, and the like). Exemplary biological samples include, without limitation, one or more samples selected from the group consisting of blood, plasma, cells, tissues, and serum. Samples may be obtained at any time prior to the amplification protocol, and subsequent detection of amplification products, but in particular aspects, the time between sample collection, isolation of a population of polynucleotides from the sample, and the amplification/detection analysis of the target nucleic acids of interest is quite short, such as, on the order of minutes to hours from specimen collection to amplification product detection. In certain embodiments, the composition may further include one or more specimen stabilizing, inactivating, storage, transport solutions, as well as one or more PCR buffers, reagents, polymerases, and such like.

In particular aspects as described herein, in certain situations, particularly when performing the method for the analysis of specimens that are acquired in remote or field sites, the compositions of the present invention are preferably stable for extended periods of time at ambient temperatures, and the collected biological specimens do not require particular refrigeration or freezing in order to prepare them for the amplification/detection steps of the overall identification process.

It is contemplated that in certain embodiments, the compositions disclosed herein may be formulated such that the entire specimen collection and nucleic acid amplification/detection process may be accomplished in remote, field, battlefield, rural, or otherwise non-laboratory conditions without significantly limiting the fidelity, accuracy, or efficiency of the amplification/detection methodology. Such aspects of the invention provide particular advantages over conventional laborious isolation/collection/transport/storage/analysis protocols that require several days to several weeks to achieve, and must often be conducted under conditions that require refrigeration or freezing of the sample and/or assay reagents in order to properly complete the analysis. By providing reagent mixtures that include all of the necessary isolation, storage, and polynucleotide stabilization components, as well as all of the necessary reagents for amplification of selected target nucleotides (including, without limitation, the amplification primers and detection probes described herein, alone or in combination with one or more PCR buffers, diluents, reagents, polymerases, detectable labels, and such like) in a single, shelf-stable, ambient-temperature facile reagent mix, significant cost savings, time-reduction, and other economies of scale may be achieved using the present invention as compared to many of the conventional oligonucleotide probe-based thermal cycling assays currently available in the marketplace. The detailed use of particular isolation/storage/transport solutions that are contemplated to be applicable to the preparation of target populations of polynucleotides is described in copending U.S. patent application Ser. No. 12/243,949, filed Oct. 1, 2008, which is commonly co-owned with the present application, and the contents of which is specifically incorporated herein in its entirety by express reference thereto.

When a real-time PCR methodology is employed for the amplification, the detecting may optionally performed at the end of a given number of cycles, or alternatively, after one or more of each cycling step in the amplification protocol.

In the regular practice of the method, one may also perform the cycling step on one or more "negative" and/or "positive" control sample(s) as is routinely done in the molecular genetic assay arts to ensure integrity, fidelity, and accuracy of the method. The use of such controls is routine to those of ordinary skill in the art and need not be further described herein. Likewise, in the practice of the invention, it may also be desirable to incorporate one or more known "internal positive controls" into the population of polynucleotides to be isolated, to further ensure the integrity, fidelity, and/or accuracy of the disclosed method. The detailed use of such controls is described in copending U.S. patent application Ser. No. 12/426,890, filed Apr. 20, 2009, which is commonly co-owned with the present application, and the contents of which is specifically incorporated herein in its entirety by express reference thereto.

In another embodiments, the invention provides an Influenza A H1N1 Virus-specific oligonucleotide amplification primer set, wherein the first amplification primer is less than about 50 nucleotides in length and includes the nucleotide sequence of SEQ ID NO:51 and the second amplification primer is less than about 50 nucleotides in length and includes the nucleotide sequence of SEQ ID NO:52. This Influenza A H1N1 Virus-specific oligonucleotide amplification set may optionally further include a first detection probe, wherein the first detection probe includes a labeled oligonucleotide probe of less than about 50 nucleotides in length that includes the nucleotide sequence of SEQ ID NO:53.

The invention also provides a diagnostic nucleic acid amplification/detection kit that generally includes, in a suitable container, an Influenza A H1N1 Virus-specific oligonucleotide amplification primer set as described herein, and instructions for using the primer set in a PCR amplification of a population of polynucleotides obtained from a biological sample or specimen. Such kits may further optionally include, in the same, or in distinct containers, an oligonucleotide detection probe that specifically binds to the amplification product produced from PCR amplification of a population of polynucleotides obtained from a biological sample or specimen that contains, or is suspected of containing, an Influenza A H1N1 Virus-specific nucleic acid segment. Such kits may also further optionally include, in the same, or in a distinct container, any one or more of the reagents, diluents, enzymes, detectable labels (including without limitation, one or more radioactive, luminescent, chemiluminescent, fluorescent, enzymatic, magnetic, or spin-resonance labels), dNTPs, and such like that may be required to perform one or more thermal cycling amplifications of a population of polynucleotides as described herein. The kits, may also further optionally include, in the same, or in a distinct container, any one or more buffers, surfactants, chaotropes, DNAses, RNAses, or other such nucleic acid isolation and/or purification reagents as may be required to prepare a sample for analysis. In certain embodiments, the kits of the invention may also optionally further include one or more portable, ruggedized, or field-employable thermal cycling, PCR amplification systems and/or one or more systems, devices, or instruments to facilitate detection, quantitation, and/or distribution of the detectable label(s) employed for visualization of the amplification products produced during the practice of the method.

In another embodiment, the invention provides an article of manufacture that includes a pair of Influenza A H1N1 Virus-specific oligonucleotide amplification primers; and a first Influenza A H1N1 Virus-specific oligonucleotide detection probe; wherein the detection probe includes at least one detectable label. Such article of manufacture may optionally further include, for example, one or more package insert(s) having instructions for using the pair of primers and the detection probe to detect the presence or absence of an Influenza A H1N1 Virus-specific nucleic acid segment within a population of polynucleotides obtained from a biological sample that was collected from a human subject.

In yet another aspect, the invention also provides a composition that includes:

(a) a first pair of Influenza A H1N1 Virus-specific amplification primers, wherein the pair of primers includes:
   - (i) a first oligonucleotide primer of less than about 50 nucleotides in length that includes the nucleic acid sequence of SEQ ID NO:51; and
   - (ii) a second oligonucleotide primer of less than about 50 nucleotides in length that includes the nucleic acid sequence of SEQ ID NO:52; and (b) a first Influenza A H1N1 Virus-specific oligonucleotide detection probe, including:

(i) a first oligonucleotide detection probe of less than about 50 nucleotides in length, wherein the probe includes the nucleic acid sequence of SEQ ID NO:53; and (ii) at least a first detection reagent operably linked to the oligonucleotide detection probe.

In yet another embodiment, the invention provides a method of identifying a subtype of Influenza A virus. This method generally involves detecting the presence of an Influenza A virus-specific nucleic acid segment in a population of polynucleotides, if present, using a labeled oligonucleotide probe that is specific for the Influenza A virus-specific nucleic acid segment; and if an Influenza A virus-specific nucleic acid segment is present in the population, then further identifying the Influenza virus using a labeled oligonucleotide probe that is specific for an H5 or an H1N1 subtype of the virus. Such method may further optionally include the additional step of determining whether the influenza A type-specific nucleic acid segment so detected is specific for a particular subtype, or specific for a particular strain of influenza virus, such as, for example, whether the influenza A type-specific nucleic acid is an H5 or an H1N1 subtype (such as an H1N1 Swine 2009) subtype.

In such methods, the identification and/or characterization of the particular subtype of Influenza A may be performed simultaneously, or sequentially. In other embodiments, it may also be desirable to determine the presence or absence of Influenza B-specific nucleic acid sequences in the population of polynucleotides so analyzed. In such cases, an assay that is specific for Influenza B may also be performed on the sample either simultaneously or sequentially.

In illustrative examples, the labeled oligonucleotide probe useful in detecting particular Influenza sub-type or strain-specific nucleic acid sequences will preferably comprise, consist essentially of, or alternatively consist of, a labeled oligonucleotide probe that comprises the sequence: 5'-TCCAAAATATGTAAAAAG-3' (SEQ ID NO:53), 5'-TCAGGCCCCCTCAAAGC-3' (SEQ ID NO:54); 5'-ATGGGAAATTCAGCTCT-3'(SEQ ID NO:55); 5'-TCTCCAAAGTATGTCAGG-3' (SEQ ID NO:56); 5'-TGAGATCAGATGCACCCAT-3' (SEQ ID NO:57); 5'-AGAGRGGAAATAAGTGG-3' (SEQ ID NO:58), or any combination thereof. As described elsewhere herein, such oligonucleotide probes are preferably labeled with a fluorescently-detectable label, including, without limitation, FAM.

In another embodiment, the invention provides a composition for the detection of nucleic acids that is at least substantially stable at room temperature and is adapted and configured for use with a polymerase chain reaction (PCR) device.

The invention also provides a biological organism identification product that generally includes: (a) a collection device to collect one or more sample organisms; (b) a fixing and transporting composition present in an amount sufficient to kill the one or more sample organisms associated with the collection device; (c) an extraction member to extract a sufficient amount of genomic nucleic acid from the one or more sample organisms to facilitate identification thereof; and (d) a substantially stable polymerase chain reaction (PCR) component into which the sufficient amount of genomic nucleic acid can be added. In exemplary embodiments, the PCR component will preferably include a composition that includes (a) a first pair of Influenza A H1N1 Virus-specific amplification primers, wherein the pair of primers includes: (i) a first oligonucleotide primer of less than about 50 nucleotides in length that includes the nucleic acid sequence of SEQ ID NO:51; and (ii) a second oligonucleotide primer of less than about 50 nucleotides in length that includes the nucleic acid sequence of SEQ ID NO:52; and a first Influenza A H1N1 Virus-specific oligonucleotide detection probe, that includes: (i) a first oligonucleotide detection probe of less than about 50 nucleotides in length, wherein the probe includes the nucleic acid sequence of SEQ ID NO:53; and (ii) at least a first detection reagent operably linked to the oligonucleotide detection probe.

In another embodiment, the reagent mix is configured and adapted used to identify one or more sample biological organisms that have been collected by a collection device. In a preferred embodiment, the reagent mix is used to identify the one or more samples at a field site or a remote location.

In another embodiment, the reagent mix is contained in a liquid form. In a preferred embodiment, the reagent mix is present in a liquid form in a test tube, a 96-well plate, or a capillary vessel. In yet another embodiment, the mixture is lyophilized.

The invention further encompasses methods for detecting a microbial sequence which includes: obtaining genomic nucleic acid from a biological sample, and assaying the genomic nucleic acid by adding the nucleic acid to the reagent mix, wherein the mix is at least substantially stable at room temperature and is configured and adapted for use with a polymerase chain reaction (PCR) device. In another embodiment, the assaying further includes adding the reagent mix to the polymerase chain reaction (PCR) device, running the assay, and completing the assay in less than about 90 minutes. In a preferred embodiment, the assaying further includes detecting the microbial sequence in real-time using fluorescence equipment adapted for use with the PCR device. In yet another embodiment, the genomic material is from a bacteria or virus, or a pathogen. In yet a further embodiment, the genomic material is from an influenza virus.

Commercial Formulations and Kits

The present invention also provides kits and sample collection systems utilizing the disclosed compositions described herein. In particular embodiments, such sample collection systems may include a collection device, such as a swab, curette, or culture loop; and a collection vessel, such as a vial test tube, or specimen cup, that contains one or more of the compositions disclosed herein. The collection vessel is preferably releasably openable, such that it can be opened to insert the one-step compositions and closed and packaged, opened to insert the sample and optionally a portion of the collection device and closed for storage and transport, or both. The collection vessel may use any suitable releasably openable mechanism, including without limitation a screw cap, snap top, press-and-turn top, or the like. Such systems may also further optionally include one or more additional reagents, storage devices, transport devices, and/or instructions for obtaining, collecting, transporting, or assaying one or more samples in such systems.

Kits may also be packaged for commercial distribution, and may further optionally include one or more collection, delivery, transportation, or storage devices for sample or specimen collection, handling, or processing. The container(s) for such kits may typically include at least one vial, test tube, flask, bottle, specimen cup, or other container, into which the composition(s) may be placed, and, preferably, suitably aliquotted for individual specimen collection, transport, and storage. The kit may also include a larger container, such as a case, that includes the containers noted above, along with other equipment, instructions, and the like. The kit may also optionally include one or more additional reagents, buffers, or compounds, and may also further optionally include instructions for use of the kit in the collection of a clinical, diagnostic, environmental, or forensic sample, as well as instructions for the storage and transport of such a sample once placed in one or more of the disclosed compositions.

Any of the embodiments illustrated herein stand independently, and any features or embodiments may be combined in any way, unless expressly excluded, to achieve a preferred embodiment. Additional advantages and embodiments of the invention will also become more apparent to those of ordinary skill in the art upon review of the teachings of the present application.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 1A and FIG. 1B illustrate the stability of reagents over time at varying temperatures in accordance with one embodiment of the invention;

FIG. 4A shows a nucleic acid sequence alignment from the H5 region of 22 Influenza A viral strains, and the particular forward and reverse primer sequences utilized for amplification of the H5 target consensus;

FIG. 5 shows Table 1, which presents exemplary oligonucleotide sequences for various primer/probe sequences used in the real-time RT-PCR amplification assays described herein, as well as the forward and reverse primer sequences used for the in vitro generation of cDNA target templates for H1, H3, and H5-specific isolates;

FIG. 6 summarizes the data from Table 2, which illustrates the detection of various influenza virus type A and B strains using type-specific assays;

FIG. 7 summarizes the data from Table 3, which illustrates the detection of various influenza virus types (A/B) and subtypes (H1, H3, and H5) in cultured clinical isolates using real-time RT-PCR;

FIG. 8 summarizes the data from Table 4, which illustrates the detection of various influenza virus types (A/B) and subtypes (H1, H3, and H5) in uncultured primary clinical specimens using real-time RT-PCR;

FIG. 9 summarizes the data from Table 5, which illustrates the primer/probe sequences used for real-time RT-PCR amplification and in vitro generation of cDNA target templates for the H1N1 (Swine flu 2009) subtype of Influenza A virus;

DETAILED DESCRIPTION OF PREFERRED EMBODIMENTS

Figures 2A, 2B, 2C:
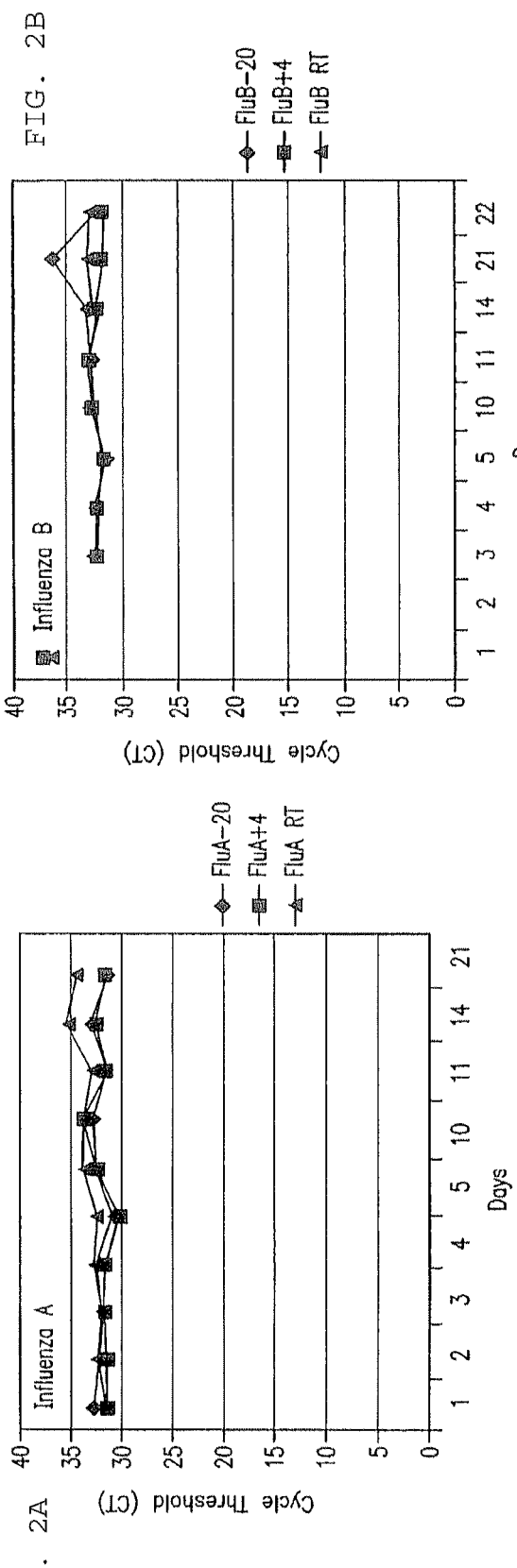
FIG. 2A, FIG. 2B, and FIG. 2C illustrate the stability of the reagents over time at varying temperatures in accordance with one embodiment of the invention.

The present invention provides a diagnostic tool, and methods of using the same, that permit rapid identification of one or more biological organisms of interest. Preferably, the detection and identification is sufficiently rapid so as to permit real-time or substantially real-time surveillance as to the spread of a particular organism in one or more host populations. In particular, the invention can combine recombinant DNA/RNA isolation and detection techniques to rapidly and remotely detect and identify organisms, such as microorganisms, typically pathogens. The pathogens most typically in need of identification according to the invention include microbes that cause malaria, viruses, preferably communicable viruses, and more preferably influenza, and bacteria. Advantageously, the identification can further include subtyping and/or lineage distinction of an influenza strain or a similar species identification of another microorganism. Typically the sample is collected from a host, which provides the sample to be tested in the diagnostic product of the invention. More specifically, the present invention can advantageously allow isolation of the organism from host tissue, isolation of the genomic material of the organism, detection and identification of organisms from a target sample, on-site analysis of the organism, and identification of the organism. In some embodiments, the diagnostic tool includes a therapeutic, preventative, or prophylactic agent for administration to the host(s), which agent is selected based on the organism identified according to the invention. In other embodiments, the diagnostic tool includes detecting resistance to therapeutic agents.

The present invention provides advantages over the prior art by providing more rapid and efficient detection, classification/sub-typing, and isolation of biological organisms from a host or target specimen. In variations of the present invention, the components of the diagnostic tool can be securely enclosed in a portable enclosure to retain them in association for travel to a field site, or for use in emergency rooms and doctor's offices.

Preferred embodiments of the invention allow the identification of a biological organism at a field site. Advantageously, the enclosure contains sufficient equipment to permit multiple identifications of different collection samples in the field without requiring transport or return to a laboratory or central processing center. As used herein, the "field" encompasses any setting outside of the traditional laboratory setting. This includes emergency rooms and doctor's offices, as well as the outdoors, villages, homes, commercial offices, warehouses, streets, field hospitals, etc., and areas in which there are limited or no modern amenities (e.g., potable water and/or electricity).

In some embodiments of the present invention, the diagnostic tool includes equipment and materials to conduct and analyze the PCR for each assay. The machinery to conduct PCR is readily understood by those of ordinary skill in the art, and lower weight and bulk selections can be made according to the invention as desired to increase portability of the kit of the invention. The assays can be used in association with many types of PCR instruments, preferably with virtually every PCR instrument. Preferably, the PCR equipment is sufficiently light-weight, and adapted to draw minimal power, for increased portability and duration of use. Fluorescence-linked PCR equipment for real-time identification of a microbial sample, as is known in the art, can also be used. Although any suitable PCR equipment may be included in the product of the invention, one preferred type of PCR equipment includes the field-hardened R.A.P.I.D.® PCR equipment commercially available from Idaho Technology. Other commercially available instruments that can be used in accordance with the present invention include the LightCycler®, and the ABI 7500 (7000).

In yet other embodiments of the present invention, particularly where PCR equipment is included in association with the portable enclosure, the portable enclosure includes at least one power source. While any suitable power source providing sufficiently consistent electrical output may be used, preferably the power source includes a battery, an electrical generator, a solar panel, or a combination thereof, along with any associated devices such as power cords or plug adapters to facilitate connection of the power source to any field equipment, such as a PCR device, that requires electricity to conduct the methods of the invention. In some variations of the present invention, the diagnostic product further includes replacement or repair components to maintain or enhance operation of the diagnostic tool over extended periods of time in the field without resupply. This feature is essential in some embodiments, as the product of the invention may be used in a quarantine or restricted travel environment where fresh supplies may not be available. In additional embodiments, the diagnostic tool includes any desired processor, e.g., a computer or a PDA with the relevant software, to conduct an analysis of the diagnostic testing. In certain variations, the processor determines which, if any, organisms are identified and detected. The software can be adapted and configured to search for certain likely types of organisms first depending on the field location, e.g., malaria in a tropical setting, as well as providing a knowledge base of biological organisms with information that can permit an optional, associated human operator to make any desired adjustments or to assist with the detection and identification, e.g., an analysis of the assay results.

As used herein, the term "infection," "influenza infection," "viral infection," "bacterial infection," and the like are used consistently with their accepted meanings in the art, but can also encompass the detrimental effect of a biological organism that does not result in an infection as conventionally understood. The term "methods of treating" includes methods of managing, and when used in connection with the biological organism or infection, includes the amelioration, elimination, reduction, prevention, or other relief or management from the detrimental effects of a biological organism. In a preferred embodiment, these detrimental effects include an influenza infection, influenza virus, symptoms characterizing and/or effects associated with influenza in the subject, or a combination.

In some embodiments of the present invention, the portable diagnostic is equipped with suitable amounts of components to conduct a plurality of assays, without leaving the field or compromising sterilization or a quarantine. In some variations, the portable enclosure includes each selected component to detect and/or identify an organism in an amount sufficient to conduct at least 10 field diagnoses, preferably about 20 field diagnoses, more preferably about 50-field diagnoses, and most preferably about 100 field diagnoses. In preferred variations, the portable enclosure includes at least enough components to conduct a plurality of field analyses while maintaining the portability of the diagnostic tool. Another measure of the quantity of components present is enough of each of the types of components necessary to identify an organism over an extended period of time in the field. For example, this time period might be about 6 hours to 2 weeks, preferably 12 hours to 1 week.

In other preferred embodiments, the diagnostic tool is durable and stable, particularly during storage and transport, as well as preferably in the field during use. The components of the diagnostic tool are hardened to resist degradation even at storage temperatures of about 18° C. to 27° C., and preferably from about 20° C. to 25° C.

In addition to temperature resistance, the portable enclosure and the contents are preferably also adapted and configured to resist or prevent physical damage and/or breakage of the components therein according to the invention. The enclosure need not be complete, and may include gaps, holes, or projections to facilitate transport or storage. The product can also be arranged in modular form, such as in blister packs, so that each type of component can be stored separately or together if desired. For example, each module can hold all the components of the product, or each module can hold one type of component. Preferably, one module includes the stabilized component(s) and is stored separately under chilled conditions (i.e. less than room temperature), such as under refrigeration of less than 4° C., or more preferably under frozen conditions, until the product is ready to be transported to a remote field site. The chilled module can be combined or included with the other modular components by any conventional means to form the complete product.

Preferably, it is a complete enclosure sufficient to resist water penetration, and the enclosure is preferably waterproof. In some variations, the portable enclosure optionally includes an apparatus to facilitate portability, such as a handle, a strap, etc. In other variations, the portable enclosure includes a fastenable and resealable opening and closing feature that allows access to the components, safe storage of the portable enclosure, and/or maintenance of sterilized components, e.g., one or more door or hatch handles, zippers, latches, or the like.

The enclosure itself may be made of any sufficiently resilient packaging material available to those of ordinary skill in the art that can protect fragile contents such as glassware or PCR equipment or otherwise help increase the integrity of the components of the product, particularly any lyophilized reagents or samples that are present. Preferably, the enclosure and components are made of a suitable non-breakable material other than glass to facilitate shipment or transport of the enclosure to a field site. Examples of such packaging material that can be included in forming the portable enclosure include: aluminum or plastic foil, blister packs, cardboard or other paperboard, or a polymeric or other plastic component such as a thermoplastic polyolefin, or a temperature-stable polymer. For example, the resilient packaging material may include a temperature-stable polymer such as a propylene homopolymer or a copolymer of at least 50 mole percent of propylene and at least one other $C_2$ to $C_{20}$ alpha-olefin, or mixtures thereof. Exemplary alpha-olefins of such copolymers include ethylene, 1-butene, 1-pentene, 1-hexene, methyl-1-butenes, methyl-1-pentenes, 1-octene and 1-decene, or a combination thereof.

The enclosure may be formed through any available process, which may be selected by one of ordinary skill in the art with reference to the type of material. For example, a polymeric material may be molded or extruded. While any shape may be imparted to the enclosure that is sufficient to enclose the components, preferably the enclosure has a base that is sufficiently stable (e.g., flat) that it will not tip over during storage or use. The enclosure can be arranged to fold open to a table if desired, with the legs folded up inside when closed and an outer surface of the enclosure forming the tabletop surface when opened. The contents may be placed on the opened table to provide a convenient workbench when conducting the methods of the invention. Other convenient arrangements of the enclosure can be envisioned, such as an opening to form a shelf that can be placed on an existing table.

The diagnostic product includes one or more types of collection device to capture, collect, or otherwise take the target specimen from the host, and then contain or hold the specimen for further analysis. The specimen may include tissue, blood, saliva, or another biological product testable for genomic material from microorganisms present in the specimen. Any suitable collection device may be used to accomplish this goal. For example, swabs may be used to collect mucosal samples. Samples are preferably collected from the skin, nasal passages, oral passages, or a combination thereof. If necessary, blood may be drawn to obtain the necessary sample. Preferably, the collection device is sterile. Other preferred collection devices are those compatible for analysis with processing machinery, assay compositions and volumes, and/or size requirements for portability or as provided by the diagnostic kit described herein. Sufficient numbers of collection device, as further discussed herein, should be included to permit use of the diagnostic product in the field for an extended period of time in the event of a crisis.

In a preferred embodiment, the target specimen, or tissues or cells thereof, are immediately preserved upon, or shortly after, collection. Preferably, the target specimen is treated to kill the biological organism(s) contained therein. A preferred embodiment of the invention includes a fixing and transporting composition, which is typically a liquid and preferably a solution, emulsion, or suspension. The fixing and transporting composition helps minimize or eliminate contamination of the sample or the environment, as well as inhibiting or preventing escape of the sample. Preferably, the fixing and transporting composition includes alcohol (e.g., ethanol), guanidinium thiocyanate, or a combination thereof. Any suitable fixing and transporting composition (also referred to herein as a "fixing and transporting agent"), may be used to kill (i.e., fix) the organisms by disrupting a cellular membrane in the organism. The specimen may then be more safely transported to the assay site, which can be across a room from a patient, in a nearby room, or even more remote such as across the street or in a different part of the field site. For example, collection of genomic material from patients may occur in one tent or room, while the assays and PCR equipment are located nearby, such as within a few minutes drive. The collection device may be dried after being exposed to the fixing and transporting composition, but preferably the collector remains in the composition until just prior to the assay.

The collection and fixing of the target specimen may be arranged as follows. A cotton-tipped swab can be contacted with the nasal passages of a host. The organism(s) collected are then fixed. One fixing step that can be carried out in accordance with the present invention is generally described in Krafft, A. E., et al., *Evaluation of PCR Testing of Ethanol-Fixed Nasal Swab Specimens as Augmented Surveillance Strategy for Influenza Virus and Adenovirus Identification*, (*J. Clin. Microbiol.*, 43(4):1768-1775, April 2005) which is specifically incorporated herein in its entirety by express reference thereto. Another method of accomplishing the fixing is reported in Chomczynski and Sacchi (*Anal. Biochem.*, 162: 156-159, 1987), through the use guanidinium thiocyanate.

The swab is either soaked in or placed in alcohol to kill the organism cells while sufficiently preserving the specimen for analysis. As used herein, "preserve" means that the nucleic acid material of the organism is not unduly damaged in the fixing process so that an assay and identification can be conducted. The fixing results in a significantly safer specimen that does not require cold-temperatures for preservation, such that the non-living specimen can be transported and even shipped, via standard postal mail if necessary. Further, because the specimen is killed, there is no risk of further outbreak or infection in the carrier or those associated with shipment of the sample if necessary. For example, even though the entire method can be performed in the field, it may be desired to conduct the assay and identification in a laboratory, either in the first instance or as a second trial to confirm the results of the field identification. In a preferred embodiment, the fixing and transport composition encompasses a non-hazardous, fixed specimen that can be processed using the components of the diagnostic tool.

Moreover, a second collection device can be used and stored differently from the fixing and transporting composition. For example, a second swab could also be included in the collection device and used to collect a sample from a host for a second assay or a different type of assay, such as in a regional laboratory or on different equipment, to help confirm the diagnosis later. For example, one swab can be used to collect genomic material and assay the organism at the field site, while a second swab can collect genomic material and be disposed in a chilled package, such as a refrigeration or freezer unit for up to about 4 days, preferably capable of being transported to a remote laboratory to further analysis. The second swab can be used to help identify organisms and to test for new vaccine candidates. One example of portable, cold storage suitable for use with the invention is the American Thermal Wizard, available through American Thermal Wizard International.

The extraction member is used to extract genomic material, or other relevant biological material, to characterize and identify one or more organisms from the target specimen. As used herein, the "genomic material" includes nucleic acids, such as RNA and/or DNA, that provide information as would be known to one of ordinary skill in the art to facilitate identifying and characterizing an organism of interest. Buffers, centrifuges, syringes, etc., as would be known to one skilled in the art, are exemplary extraction members suitable for the present invention. Suitable extraction techniques include those generally described in Matthews, C. K., et al, *Biochemistry, Second Edition*, The Benjamin Cummings Publishing Co., 1996 and Tortora, G J., et al., *Microbiology: An Introduction*, The Benjamin Cummings Publishing Co., 1992, which are incorporated herein by express reference thereto. Generally, the extracted genomic nucleic acid is present in an amount from about 0.1 microliters to about 10,000 microliters, more preferably from about 1 microliter to about 1000 microliters, and more preferably from about 10 microliters to 100 microliters. An exemplary amount of nucleic acid is 25 microliters.

With respect to the extraction member, and other devices and/or apparatus in the diagnostic tool, it is preferable to maintain the equipment and identification environment in sterile or uncontaminated form. The diagnostic tool may optionally, but preferably, include one or more components to sterilize or maintain sterilization as would be known to one skilled in the art in certain embodiments. The fixing agent may also be selected to provide suitable sterilization, which may be a desirable way to reduce the number of different optional components necessary to function effectively in the field.

In the present invention, the PCR component when preferably included in the product is preferably suitable for portability and field use and analysis. One exemplary PCR assay includes real time reverse transcriptase-PCR (rRT-PCR), as generally described in Das, A., et al., *Development of an Internal Positive Control for Rapid Diagnosis of Avian Influenza Virus Infections by Real-Time Reverse transcriptase-PCR with Lyophilized Reagents, J. Clin. Microbiol.,* 44(9): 3065-3073, September 2006; specifically incorporated herein in its entirety by express reference thereto.

In preferred embodiments, the pre-selected PCR reagents are premixed to include target primers and probes in one or more PCR-adapted vessels. In the most preferred embodiments, the vessels are adapted and configured to be compatible, operable and functional with the selected PCR machinery (i.e., the PCR device). For example, capillary pipettes that are sized and dimensioned to be operatively associated with the included PCR device may be directly inserted in the compatible PCR equipment for rapid use. In accordance with certain embodiments of the invention, these contain stabilized wet reagents adapted and configured for use with the genomic material in a PCR device. In one preferred embodiment, all of the PCR reagents are stabilized. The stabilized reagents can be already disposed in a PCR holding device to which a liquid including the extracted genomic material is later added. Alternatively, PCR-usable vessels may include stabilized materials or spherules that can universally fit various PCR machinery or stabilized PCR materials from the diagnostic product can be put into solution or other liquid containing the extracted genomic material. The solution is then added to the PCR holding device, which can then be placed in the PCR machinery. In one example, the PCR holding device contains the stabilized materials and the extracted genomic material in solution is added to it. Or, by way of another example, stabilized material can be added to a cuvette to which is added extracted genomic material in solution, or vice versa, and then the proper amount of that solution can be added into the PCR holding device (e.g., a pipette), and placed in the PCR machinery.

In another preferred embodiment of the invention, the desired PCR components used to contain and assay selected types of samples are pre-loaded into one or more vessels and are then stabilized to maintain the quality of the vessel and its contents for field use once the extracted genomic material is combined.

The PCR assay is preferably included in the product for field use, and encompasses detecting the genomic material of the organism. Accordingly, in preferred embodiments, at least one reagent of the PCR component includes one or more primers and/or one or more probes specific to the detection of one or more predetermined biological organisms. The diagnostic tool preferably includes primers predetermined and preselected for use in identifying certain specific organisms. As used herein, the primer is the composition used to detect specific genomic material, such as forward and reverse primers, and a probe is a sequence that binds to a microbial sequence for amplification. The PCR provides amplified genomic material, which can chemically associate with certain primers and/or probes. In some embodiments, the primer, probe, or combination can include an anti-sense nucleic acid sequence that is chemically associable with the genetic material of a detected organism. In other embodiments, the primer, probe, or combination is chemically associable to a protein or component specific to the extracted genomic material from the biological organism. This specificity facilitates rapid identification of the organism, and/or sub-typing, e.g., to include influenza A subtypes H1, H3, H5, H7, H9, as may be readily determined by those of ordinary skill in the art particularly with reference to the present disclosure. For example, if a primer and/or probe specific to H5N1 influenza chemically associates in the assay, then there is evidence of the detection and identification of, e.g., H5 influenza in the targeted specimen.

The types of primers, probes, or both included in the diagnostic tool are preferably pre-selected by one of ordinary skill in the art. In some variations, a wide variety of primers, probes, or a combination thereof are included to detect and identify any of a corresponding wide variety of organisms, particularly where there is no advance knowledge of the type of organisms expected when using the diagnostic product. In situations in which a particular organism is suspected (e.g., H1N1 influenza), the range of primers, probes, or a combination thereof that are loaded into the portable enclosure may be focused on H1N1 influenza and influenza with a similar genomic composition, or may be exclusively those used for influenza. Preferably, the primers and probes specifically tailored to a particular strain do not cross react with other strains of the same or similar organism.

The PCR components may include a redundancy of primers and/or probes to ensure detection of a suspected organism and genome thereof. The library of primers and probes is generally increasing as the genomic sequence of new organisms are mapped, which can permit more suitable primer and probe selection for future uses of the diagnostic product. Descriptions of certain maps, primers, and probes that may be useful in connection with the invention includes those described in the Das publication, which is incorporated herein by express reference thereto. Preferably, the influenza primers and probes are designed to detect at least one strain of influenza encompassing the A or B types, and more preferably each of the sixteen H subtypes and each of the two B lineages.

In a particularly preferred embodiment, the PCR component is a reagent that includes one or more of amplification primers, detection probes and enzymes, or any combination thereof, present in a mixture. This mixture may further include standard PCR components such as water, buffer, nucleotides, polymerase, or the like, or any combination thereof. The mixture of standard components is known in the art as a master mix. One or more microbe-specific primers, probes, enzymes, or any combination can be added to the master mix to create the prime mix. The prime mix can have one, two, three or four or more microbial primers, probes and/or enzymes. The microbial primers, probes and/or enzymes can be specific to infective viral or bacterial agents in general, or to specific agents, such as those associated with influenza, dengue fever, malaria, HIV, SARS, MRSA, and tuberculosis. In one preferred embodiment, the primers, probes and/or enzymes in the prime mix are specific to the influenza strains A, B, or both. In another embodiment, the primers, probes, and/or enzymes are specific to sub-strains of influenza, such as H1, H3, H5, H7, and H9. In a further embodiment, the primers, probes, and/or enzymes are inclusive for all substrains of influenza (H1-H16 and N1-N9) and the two primary flu B circulating strains.

By way of example, certain primers and probes specific to influenza strains or types, or sub-strains or sub-types, are presented in FIG. 5 as well-suited to the present invention.

The probes of FIG. 5 are oligonucleotide sequences located internal to the forward and reverse amplification primers. These oligonucleotides are dual labeled, containing one of several types of 5' fluorescent reporters, e.g., 6-Carboxyfluorescein N-succinimidyl ester (FAM) and one of several types of 3' quenchers, e.g., TAMRA, MGB Dark Quencher, etc. The sequences for influenza strains A and B are located on RNA Segment 7, which includes the open reading frames of the two matrix genes, M1 and M2, that are highly conserved among influenza virus strains. The sequences for influenza sub-types are located on RNA Segment 4, which codes from the hemagglutinin (HA) protein. Nucleotides "Y" and "R" are degenerative nucleotides that have been included in sequence positions that exhibit high variability, and represent mixtures of nucleotides "C and T" and "A and G", respectively. Degenerative bases are used when there is genetic variability among strains at a particular nucleotide position within the genome.

In a further example, primers and probe sequences specific to the H1N1 influenza strain are presented in FIG. 9. These sequences were developed from a previously described real-time RT-PCR assay for the detection of contemporary circulating human H1 strains (Daum, et al., 2007). The probe of FIG. 9 is an oligonucleotide sequence located internal to the forward and reverse amplification primers. The probe is dual labeled, and contains a 5' FAM fluorescent reporter and a 3' Molecular-Groove Binding Non-fluorescence Quencher (MGBNFQ), which allows for the use of probes at a lower melting temperature. The primer and probe sequences for the H1N1 strain are localized to RNA Segment 4, a highly conserved area within a highly variable region of the hemagglutinin (HA) gene. The sequences additionally contain the substitution of particular bases with those observed in the 2009 H1N1 strains. Nucleotides "Y" and "R" are degenerative nucleotides. Further, the H1N1 primer and probe sequences do not cross-react with other contemporary circulating strains of H1 influenza.

The PCR component, which can be any component as discussed herein or can be, or can include, the prime mix, is present in an amount to sufficiently dissolve the extracted genomic nucleic acid material. Where the component is lyophilized, it may be necessary to reconstitute the material with added water or other suitable solvent before, with, or after combining the extracted, fixed, genomic material. The PCR vessel loaded with the genomic material is placed in the PCR machine for a prescribed period of time. For example, the assay time may take from about 30 minutes to 180 minutes, preferably about 45 minutes to 150 minutes. In a more preferred embodiment, the assay time is about 60 minutes to 120 minutes. In embodiments where the PCR component is the prime mix, detection preferably can be achieved within approximately 90 minutes from extraction. These times are intended to encompass preferred times for both DNA amplification, as well as RNA amplification that includes about 30-35 minutes for the reverse transcriptase step to convert the RNA to DNA. The exact time may be readily determined by those of ordinary skill in the art depending upon the material to be assayed and the type of PCR device selected.

The PCR reagents used in accordance with the present invention, in preferred embodiments, are designed to be at least substantially stable, and more preferably, stable. Specifically, the reagents in the form a prime mix of the present invention, are preferably substantially stable at room temperature, and this stability is measured and standardized as shown in FIG. 1A, FIG. 1B, FIG. 2A, FIG. 2B, and FIG. 2C. FIG. 1A and FIG. 1B illustrates the stability of the pathogen detection reagents. The standard chosen here is 1 picogram of initial cRNA from Flu A and H5 influenza. The Flu A and H5 samples were stored at −20° C., 4° C., and at room temperature (about 25° C.). Along the Y axis is the number of PCR cycles that have been run to register a reading. Stability as defined by the present invention is functional stability of the prime mix, which is indicated by detection of the sequence through amplification and fluorescence. In FIG. 1A and FIG. 1B, functional stability is indicated by detection of the sequence (with initial sample containing 1 pg of cRNA) up to 35 PCR cycles. The level of baseline fluorescence signifying a positive reading of a sample, and thus detection thereof, is referred to at the $C_T$ value. The Cycle Threshold ($C_T$) is defined as the fractional cycle number at which the fluorescence passes the threshold. The threshold level is the Delta Rn used for $C_T$ determination in real-time assays. The level is set to be above the baseline and sufficiently low so that it is within the exponential growth region of the amplification curve. The Delta Rn is the magnitude of the signal generated by the specified set of PCR conditions (Delta Rn=Rn−baseline). (See ABI Relative Quantification Users Guide for 7300/7500/7500 Fast Systems, Copyright July 2006.)

As shown in FIG. 1A and FIG. 1B, stability is defined as the ability to reach $C_T$ at 35 cycles or less, using 1 pg of cRNA in the starting sample. Thus, "substantially stable" encompasses prime mixes of the invention that are detectable at 1 pg through no more than 35 PCR cycles after the prime mix is stored at the specified temperature over time. For example, "substantially stable" includes prime mixes stored at room temperature for up to about 2 weeks, preferably up to about 4 weeks, and more preferably up to about 2 months or even about 3 months, where the prime mix is still useful and functioning for its intended purpose as measured by detection at 1 pg amounts in no more than 35 PCR cycles. The prime mixes are at least substantially stable for even longer periods of time at the various tested temperatures below room temperature.

FIG. 2A, FIG. 2B, and FIG. 2C show the results of a Pathogen Detection Reagent Stability Study, wherein the initial amount of cRNA is 1 femtogram. Here the cDNA is from Flu A, Flu B, and H5 influenza. FIG. 1A, FIG. 1B, FIG. 2A, FIG. 2B, and FIG. 2C illustrate the superior stability of a selection of prime mix reagents of the present invention at all three temperatures. As can be seen from the graph, the prime mix reagents for all three viruses remains stable at −20° C. and 4° C. to day 22. The stability profile at room temperature is also surprising, lasting about two weeks or more. It is further noted that the deviation around day 21 in FIG. 1A, FIG. 1B, FIG. 2A, FIG. 2B and FIG. 2C is likely due to the fact that the sample size was extremely small. As can be observed from the graph, the results of testing on day 22 showed a return to the detection level consistent with earlier testing days, indicating that stability beyond day 22 can reasonably be expected.

Based upon the data presented in FIG. 1A, FIG. 1B, FIG. 2A, FIG. 2B and FIG. 2C, substantial stability is achieved for extended period of time when the sample is kept frozen at about −20 to about 0° C., when the sample is stored above freezing such as in a refrigerator from above 0° C. to about 4° C., and when the sample is stored above refrigeration temperature to room temperature such as in the range of about 5° C. to about 27° C. In another embodiment, substantial stability can occur even at temperatures from above about 27° C. to 40° C. or about 27° C. to 50° C. Without being bound by theory, it is believed that the colder to temperature, the longer the sample will remain stable. For instance, the sample may be stable when frozen for 3-6 months, when refrigerated for 1-4 months and at room temperature for about one month.

Stability may preferably be achieved by a variety of means as in known in art. such as by lyophilizing the components. In one embodiment, stability may be enhanced by maintaining the lyophilized components of the invention below room temperature until the product is ready to be assembled, transported, or used. Based on the data from the stability studies as discussed above, stability can be achieved and maintained over a period of at least two months, more preferably three months.

This stability can be achieved by the lyophilization of all the PCR reagents before being loaded in the vessels included in the enclosure or before being packaged (e.g., foil or blister packs) in association with vessels. Lyophilization procedures and reagents are described in Das et al. as described above. It is noted, however, that the lyophilization of the reagents in the Das paper includes lyophilization of a master mix (nucleotides, buffer, and polymerase) only.

In accordance with one embodiment the present invention, the lyophilized reagents are disposed in the PCR-adapted vessels. Advantageously, including and using lyophilization for all PCR reagents can achieve one or more of the following: minimize efforts to assay and otherwise detect and identify organisms, particularly in difficult environments or under difficult conditions, increase assay reliability due to minimized or avoided degradation of the components, require less skilled operators of the diagnostic tool of the invention, and ensure greater durability of all components.

Stability may be achieved through any suitable method known by those of ordinary skill in the art. While lyophilization is one preferred embodiment to prepare the prime mix of the invention, the reagents can be encapsulated, e.g., in a liposome or paraffin bead, that dissociates in a PCR at typical operating temperatures, as will be readily determinable by those of ordinary skill in the art. As the PCR process is typically run at about 50° C., the liposome or bead can be designed to melt or dissolve at this temperature. Stability can also be achieved by providing all the components of the prime mix in liquid form in either a test tube, a 96-well plate, or a capillary vessel of plastic or glass. Those of ordinary skill in the art will envision other available methods to achieve the necessary stability of the prime mix of the invention based on the guidance provided herein.

Following the assaying of the genomic nucleic acid with the PCR instrument, primers, and/or probes, the results can be analyzed. Whether one or more primers and/or probes have associated with one or more organisms is generally known to those of ordinary skill in the art, based on chemical indicators, colors, and other observable results based on the reactions. For example, the association between the primers and/or probes with genetic material from the organism may be detected by fluorescence to facilitate detection of the biological organism. In certain embodiments of the present invention, the kit includes an analyzer to provide diagnostic information as to which probes, if any, provide positive results (e.g., a positive result is detection by of an organism by a probe specific for that organism). In some embodiments, the analyzer is incorporated with the PCR assay.

Following assay and identification, the diagnostic product of the invention optionally but preferably also includes the necessary pharmaceutical agent, along with pharmaceutically acceptable carrier, in the field to treat the disease or condition associated with the organism, or one or more symptoms associated therewith. Although such pharmaceutical compositions can be packaged with the product, preferably they are packaged separately from the product, particularly where the conventional pharmaceutical components are less stable than the lyophilized components. This permits pharmaceutical compositions with a longer shelf life to be included in the portable enclosure or with other modular components thereof just prior to use or transport to a field site or nearby storage site. Preferably, the diagnostic product includes a plurality of desired pharmaceutical compositions in doses in a number sufficient to prevent or treat one or more conditions caused by a selection of biological organisms depending on which organism is detected and identified. Preferably, these are formulated conventionally in a desired dosage form and strength, such as a tablet, capsule, patch, solution, lotion, or the like. Varying dosage strengths may be provided for certain types of pathogens, as appropriate. Indeed, the portable enclosure can be loaded with different components of any kind, such as active pharmaceutical ingredients, depending on the expected biological organisms or patient population one of ordinary skill in the art might encounter, based, for example, on field location, first responder reports, prior experience, or the like. If the patients are expected to be pediatric or geriatric, a larger portion of liquid formulations may be selected, by way of example.

The active pharmaceutical ingredient optionally, but preferably associated with the portable enclosure may include one or more vaccines, biologics, therapies, drugs, prophylactics, compositions (e.g., immunogenic), antidotes, treatments, cures, or any other medical item that is directed towards the treating or preventing of selected biological organisms. For example, if certain influenza strains are identified, the diagnostic tool may include Tamiflu® (Roche Pharmaceuticals Inc., New Jersey, USA) to treat the corresponding influenza infection. If certain bacteria are identified, the diagnostic tool may include certain antibiotics, such as azithromycin, effective in treating the corresponding bacterial infection. The dosages will, in any case, be present in a therapeutically or prophylactically effective amount.

Figure 3:
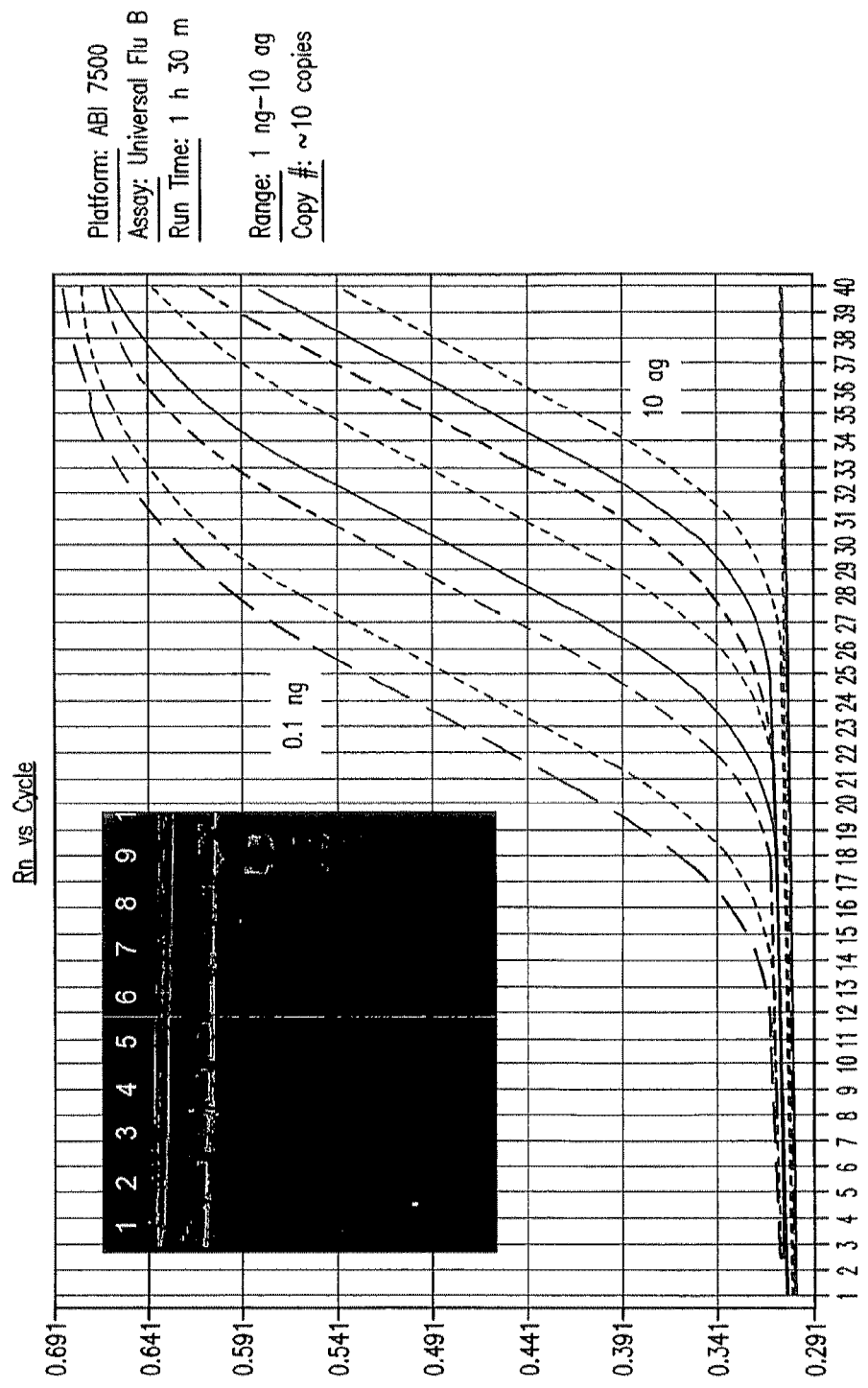
FIG. 3 illustrates the amplification and detection of an Influenza B-specific nucleic acid sequence according to an embodiment of the present invention.

In a prototype assay according to one embodiment of the present invention and where the microbe is a virus, RNA is extracted from a swab or tissue and added to the prime mix. Optionally, a control can be added to the mix. The control can be a positive control such as cRNA of the target microbe to allow a comparison to determine the identity of the sample, and/or a negative control, such as RNase-free water. The control(s) can also be run in a separate assay, either concurrently or sequentially. Next, the prime mix with the added RNA sequence to be identified is run on any suitable PCR instrument based on the guidance herein coupled with that known to those of ordinary skill in the art. Detection occurs within about 90 minutes from the time of extraction of the sample. In an assay using the prime mix, a very small number of copies of the microbial sequence are needed for identification to occur. FIG. 3 is a standard curve of concentrations from about 0.1 ng to 10 ag showing fluorescence readings of a sample having only 10 copies of a sequence in the 10 ag concentration. The gel in the upper left hand corner of FIG. 3 was run to verify the data shown fluorescence curves. In FIG. 3, influenza B is the sample being identified. As shown by the curve, 10 copies is sufficient for identification. It is further noted that, in accordance with the present invention, it is possible to identify a sequence with 5 or fewer copies of the sequence.

Methods of the present invention include detection of a microbial sequence including obtaining genomic material from a biological sample and assaying the genomic material (i.e., nucleic acid) by adding the sample material to the prime mix. In certain embodiments of the invention, the components of the prime mix may be present in liquid form in one or more laboratory vessels, such as a test tube, a 96-well plate, or a capillary of plastic or glass. The assay is preferably adapted for use with any PCR instrument, which may also include any fluorescence instrument commercially available or known in the art, for real time detection of the microbial sequence.

The prime mix of the present invention can also be used for disease surveillance. Disease susceptibility diagnostic assays can be augmentative genetic prime mix assays of the invention that provide additional medical information about one or more bacterial or viral pathogens, such as resistance markers resulting from known genetic polymorphisms/mutations that confer resistance to known drug treatment modalities.

For example, a growing number of influenza A (H3N2) isolates obtained from patients in the U.S. revealed that 92.3% contain a change at amino acid 31 (S31N) in the M2 gene known to be correlated with adamantane resistance (e.g., amantadine and rimantadine) and 2 of 8 influenza A (H1N1) strains contained the same mutation (Bright et al., *JAMA*, 2006). Adamantane resistance among influenza A (H3N2) and some H1N1 strains is highlights the clinical importance of having rapid (point of care) surveillance for antiviral resistance. In accordance with one embodiment of the invention, the prime mix can target resistance markers (e.g., by use of a probe) for neuraminidase inhibitors.

Identification of influenza to a specific strain and sub-strain can be determined by the following. It should be understood that any viral or bacterial agent may be targeted according to the invention, and that most references herein to influenza may be replaced with any other suitable viral or bacterial agent. First, an assay is run by the method outlined above to determine if an influenza pathogen is present in a sample. If an influenza infective is present in the sample, a second test can be run to determine if the virus is influenza strain A or B. If the organism is identified as influenza A, one or more additional tests can be performed to determine the subtypes, such as H1, H3, H5, etc. Preferably, this is all achieved using the same sample so that no additional samples are required from the patient or subject. Alternatively, a single test can be run with the patient sample and the primers, probes, enzymes, or any combination for multiple strains and subtypes.

There are several advantages that can be imparted by use of the prime mix of the present invention. First, when the prime mix is already assembled in a suitable container for insertion into a PCR device, it is unnecessary to store multiple individual reagents and excess laboratory equipment at a site or to carry it in the portable enclosure of the invention. This is particularly beneficial in areas where access to storage, refrigeration, transport, or any combination, is not readily available, and where mobility is desired (as it is no longer necessary to transport and store individual reagents). A further benefit of a pre-assembled prime mix, when used, is that the identification process is streamlined, requiring less time, less mixing and pipetting, less cleaning or recycling of containers, and less margin for error in measuring. The simplified process can reduce the opportunity for user error and contamination, and can advantageously expedite assay results.

Additionally, the prime mix can permit easy and rapid detection of a sample microbial sequence. Current detection methods for pathogens and disease resistance can take up to several days. In contrast, by using the prime mix of the present invention, detection can be achieved within about 90 minutes in one embodiment. As illustrated by FIG. 1A, FIG. 1B, FIG. 2A, FIG. 2B, FIG. 2C, FIG. 3, and FIG. 10, detection can be achieved using any standard PCR instrument and a small amount of the starting sequence. With a starting amount of 1 million copies of a sequence, detection can be achieved in fewer than 35 cycles. Improved detection allows identification of smaller samples. This is particularly advantageous in instances where it is desired to run multiple tests from a single sample, leaving more sample available for additional tests. This feature may also be beneficial in the event that a sample has been compromised, perhaps through transit or exposure, and less sample is intact for testing.

Surprisingly, the prime mix exhibits markedly increased stability, lasting several days or longer at room temperature. In another more preferred embodiment, the prime mix exhibits substantial stability for at least about two weeks, and up to about one month at room temperature. Stability for an extended period of time at room temperature (approximately 23° C.-27° C.) imparts great flexibility in use in both traditional and non-traditional environments. For example, the assay can be used more reliably in hospitals, doctor's offices, as well as in remote locations, such as in areas that have been subject to a bioterrorist attack, natural disaster, or at battlefield. The invention can be used at airports and border crossings to help minimize or prevent infected individuals from spreading disease.

Further, the prime mix can provide great flexibility and compatibility of use. The prime mix is adapted for use with several rRt PCR formats, and is available ready-to-use in reaction vessels for direct and immediate analysis. The prime mix can be used with any extraction or purification kit, and can include any standard master mix components (buffer, nucleotides, polymerase) available in the art as well as components described herein.

It is noted that the present invention encompasses the prime mix alone, existing independently from any apparatus or kit. Separate, additional embodiments of the present invention are directed to the use of the prime mix with other apparatuses, kits, etc.

In one aspect of the invention, there is provided a method for detecting the presence or absence of an influenza A-specific nucleic acid. In particular aspects, the invention provides a method and compositions for detecting the presence or absence of an influenza B-specific nucleic acid. In some embodiments, there is provided a method for detecting the presence or absence of a particular subtype of influenza A, such as, for example, an H1N1 subtype, including, for example, such H1N1 strains that are commonly referred to as "swine flu" isolates.

In particular, the invention provides novel probes and primers that may be used to specifically detect the presence or absence of particular H1N1 subtype viral strains that are causal agents for the influenza viral strains that are the causal agents of the 2009 H1N1 swine flu.

In an overall sense, the invention provides methods and compositions for detecting an H1N1 subtype viral nucleic acid from within a plurality of polynucleotides obtained from a biological sample. There is also a method for quantitating the amount of H1N1 subtype viral nucleic acid within the sample and monitoring the efficacy of the formulations at stabilizing and protecting the molecular fidelity of the isolated polynucleotides.

In another aspect, the present invention provides a method for rapidly detecting in a biological sample, a particular polynucleotide sequence, such as an H1N1 Influenza A subtype-specific nucleic acid. In an overall and general sense, this method includes amplification of a population of nucleotides suspected of containing the particular sequence using conventional methods such as PCR and forward and reverse primers that are specific for the target sequence, hybridization of a specific probe set with the resulting single-stranded PCR product, performing melting curve analysis and analyzing the $T_m$ change of the hybrid of the single-stranded PCR product with the hybridization probes.

In one embodiment, the present invention provides a method for rapidly detecting the presence of a polynucleotide (such as an H1N1 subtype viral nucleic acid sequence), using a PCR-based methodology, which generally includes: (a) isolating polynucleotides from the sample to be analyzed; (b) amplifying the polynucleotides by PCR using a primer set that is specific to the H1N1 subtype viral nucleic acid target sequence; (c) hybridizing one or more labeled probes that are specific for the polynucleotide of interest with the single-stranded PCR product obtained from step (b); and (d) detecting the presence of the labeled probe in the sample, indicative of the presence of the specific H1N1 subtype viral nucleic acid target sequence within the population of isolated polynucleotides.

In another aspect, the present invention provides a method for rapidly detecting in a biological sample, a particular nucleic acid sequence from among a population of polynucleotides isolated from a biological sample. In an overall and general sense, this method includes amplification of a population of nucleotides suspected of containing the particular sequence using conventional methods such as PCR and forward and reverse primers that are specific for the target sequence, hybridization of a specific probe set with the resulting single-stranded PCR product, performing melting curve analysis and analyzing the $T_m$ change of the hybrid of the single-stranded PCR product with the hybridization probes.

One such method for the detection of polynucleotides using a labeled "probe" sequence utilizes the process of fluorescence resonance energy transfer (FRET). Exemplary FRET detection methodologies often involve pairs of fluorophores including a donor fluorophore and acceptor fluorophore, wherein the donor fluorophore is capable of transferring resonance energy to the acceptor fluorophore. In exemplary FRET assays, the absorption spectrum of the donor fluorophore does not substantially overlap the absorption spectrum of the acceptor fluorophore. As used herein, "a donor oligonucleotide probe" refers to an oligonucleotide that is labeled with a donor fluorophore of a fluorescent resonance energy transfer pair. As used herein, "an acceptor oligonucleotide probe" refers to an oligonucleotide that is labeled with an acceptor fluorophore of a fluorescent resonance energy transfer pair. As used herein, a "FRET oligonucleotide pair" will typically include an "anchor" or "donor" oligonucleotide probe and an "acceptor" or "sensor" oligonucleotide probe, and such pair forms a FRET relationship when the donor oligonucleotide probe and the acceptor oligonucleotide probe are both hybridized to their complementary target nucleic acid sequences. Acceptable fluorophore pairs for use as fluorescent resonance energy transfer pairs are well known to those skilled in the art and include, but are not limited to, fluorescein/rhodamine, phycoerythrin/Cy7, fluorescein/Cy5, fluorescein/Cy5.5, fluorescein/LC Red 640, and fluorescein/LC Red 705, and the like.

Primers useful in amplification of a particular sequence of interest may be designed using, for example, a computer program such as OLIGO® (Molecular Biology Insights Inc., Cascade, Colo., USA). Typically, oligonucleotide primers are from about 10 to about 60 or so nucleotides in length (including, without limitation, all intermediate integers, e.g., 10, 11, 12, etc., or even 60 or more nucleotides in length), although primers of any practical length may be useful in the practice of certain embodiments of the invention.

The invention also provides a method for increasing the efficiency of obtaining a purified population of H1N1 subtype viral nucleic acids from a biological sample suspected of containing such H1N1-specific nucleic acids. In an overall and general sense, the method includes contacting the sample with a composition that includes one or more of the formulations described herein, in an amount and for a time sufficient to increase the efficiency of obtaining the purified population of H1N1-specific polynucleotides from the biological sample.

In exemplary embodiments, the integrity of a population of polynucleotides in the biological sample, and/or the fidelity of at least a first sequence of at least one of the polynucleotides obtained from the sample is at least substantially maintained (i.e., at least 75% of the nucleotides within the population are substantially full-length) when the composition including the sample is stored at a temperature of from about −20° C. to about 40° C. for a period of from about 7 to about 14 days or longer; alternatively at a temperature of from about −20° C. to about 40° C. for a period of from about 7 to about 14 days or longer; or alternatively at a temperature of from about 20° C. to about 40° C. for a period of from about 14 to about 30 days or more.

Alternatively, the integrity of a population of polynucleotides in the biological sample is at least substantially maintained such that at least about 80%, at least about 85%, at least about 90%, or at least about 95% or more of the nucleotides within the population are present in the solution when compared to the amount present in the solution when the sample was initially collected. In preferred embodiments, the integrity of the sample will be substantially maintained such that all, or almost all of the viral-specific polynucleotides present in the initial sample will be maintained (i.e., not detectably degraded) over time.

In the practice of the disclosed methods, preferably from the time of collection to the time of isolating, purifying, or characterizing a population of polynucleotides therein, less than about 20% of the population of polynucleotides originally present in the collected sample will be degraded over time during subsequent storage. Preferably, substantially less than about 15% of the population of polynucleotides originally present in the collected sample will be degraded over time during subsequent storage, more preferably, less than about 10% of the population of polynucleotides originally present in the collected sample will be degraded over time during subsequent storage, and more preferably still, less than about 5% of the population of polynucleotides originally present in the collected sample will be degraded over time during subsequent storage. In particularly preferred embodiments, not more than about 5%, about 4%, about 3%, about 2% or about 1% of the population of polynucleotides originally present in the collected sample will be degraded over time during subsequent storage. Such high-integrity preservation of sample quality is preferable, regardless of the conditions under which the sample is stored, and will be substantially maintained for a period of time of at least about 7 days, at least about 14 days, at least about 21 days, at least about 30 days, at least about 45 days, at least about 60 days, or even at least about 90 days or more.

While the presence of, integrity of, or sequence fidelity of, a particular polynucleotide sequence obtained from, or utilized in the practice of the present invention may be determined using any conventional methodology known to those of ordinary skill in the molecular arts, in one embodiment, PCR amplification is utilized. Likewise, determination of the integrity of a polynucleotide of interest may include determination of the PCR cycle threshold ($C_T$) under given conditions, and determination of the sequence fidelity, qualitative integrity of collected nucleic acids may be determined by conventional DNA or RNA sequencing methods, including, without limitation, the chemical-based methods of Maxam-Gilbert, the dideoxy chain termination method of Sanger et al., the dye fluorophore-based method of Mathies et al., or pyrosequencing techniques as described by Nyren and Ronaghi.

Exemplary formulations of the invention include a reagent mixture that includes probe and primer sequences specific for the detection, quantitation, amplification, and/or analysis of influenza A and/or B virus, and in certain embodiments, probe and primer sequences that are specific for the detection, quantitation, amplification, and/or analysis of H1N1 subtypes of influenza A virus, and in particular, those H1N1 subtypes of influenza A virus that are known or suspected to be causal agents of the 2009 "swine flu" pandemic.

In certain embodiments, the target nucleic acids to be assayed for influenza virus, will be obtained using a one-step sample collection/storage/transport medium that includes: a) one or more chaotropes (each preferably present in the composition an amount from about 0.5 M to about 6 M); b) one or more detergents (each preferably present in the composition an amount from about 0.1% to about 1%); c) one or more chelators (each preferably present in the composition in an amount from about 0.01 mM to about 1 mM); d) one or more reducing agents (each preferably present in the composition in an amount from about 0.05 M to about 0.3 M); and e) one or more defoaming agents (each preferably present in the composition in an amount from about 0.0001% to about 0.3%) to release such nucleic acids from a first biological sample suspected of containing one or more such target nucleic acids.

Exemplary chaotropes include, without limitation, guanidine thiocyanate (GuSCN), guanidine hydrochloride (GuHCl), guanidine isothionate, potassium thiocyanate (KSCN), sodium iodide, sodium perchlorate, urea, or any combination thereof. Descriptions of additional exemplary chaotropes and chaotropic salts can be found in U.S. Pat. No. 5,234,809 (specifically incorporated herein in its entirety by express reference thereto).

Exemplary detergents include, without limitation, sodium dodecyl sulfate (SDS), lithium dodecyl sulfate (LDS), sodium taurodeoxycholate (NaTDC), sodium taurocholate (NaTC), sodium glycocholate (NaGC), sodium deoxycholate (NaDC), sodium cholate, sodium alkylbenzene sulfonate (NaABS), N-lauroyl sarcosine (NLS), salts of carboxylic acids (i.e., soaps), salts of sulfonic acids, salts of sulfuric acid, phosphoric and polyphosphoric acid esters, alkylphosphates, monoalkyl phosphate (MAP), and salts of perfluorocarboxylic acids, anionic detergents including those described in U.S. Pat. No. 5,691,299 (specifically incorporated herein in its entirety by express reference thereto), or any combination thereof.

Exemplary reducing agents include, without limitation, 2-mercaptoethanol (β-ME), tris(2-carboxyethyl)phosphine (TCEP), dithiothreitol (DTT), formamide, dimethylsulfoxide (DMSO), or any combination thereof. In a preferred embodiment, the reducing agent includes or is TCEP.

Exemplary chelators include, without limitation, ethylene glycol tetraacetic acid (EGTA), hydroxyethylethylenediaminetriacetic acid (HEDTA), diethylene triamine pentaacetic acid (DTPA), N,N-bis(carboxymethyl)glycine (NTA), ethylenediaminetetraacetic (EDTA), citrate anhydrous, sodium citrate, calcium citrate, ammonium citrate, ammonium bicitrate, citric acid, diammonium citrate, potassium citrate, magnesium citrate, ferric ammonium citrate, lithium citrate, or any combination thereof. In preferred embodiments, the chelator includes EDTA, a citrate, or a combination thereof. In a more preferred embodiment, the chelator includes EDT.

Compositions used in preparing one or more biological samples for liberation of nucleic acids contained therein may further also optionally include one or more defoaming agents to prevent the formation of bubbles that typically result from the presence of detergents in the formulation. Defoaming agents facilitate pipetting and handling of the disclosed compositions. Exemplary surfactants/defoaming agents include, without limitation, cocoamidopropyl hydroxysultaine, alkylaminopropionic acids, imidazoline carboxylates, betaines, sulfobetaines, sultaines, alkylphenol ethoxylates, alcohol ethoxylates, polyoxyethylenated polyoxypropylene glycols, polyoxyethylenated mercaptans, long-chain carboxylic acid esters, alkonolamides, tertiary acetylenic glycols, polyoxyethylenated silicones, N-alkylpyrrolidones, alkylpolyglycosidases, silicone polymers such as Antifoam A®, or polysorbates such as Tween®, or any combination thereof. In a preferred embodiment, a defoaming agent includes a silicone polymer.

Optionally, compositions of the invention may also further include one or more buffers (each preferably present in the final composition in an amount from about 1 mM to about 1 M). Exemplary buffers include, without limitation, tris(hydroxymethyl)aminomethane (Tris), citrate, 2-(N-morpholino)ethanesulfonic acid (MES), N,N-bis(2-hydroxyethyl)-2-aminoethanesulfonic acid (BES), 1,3-bis(tris(hydroxymethyl)methylamino)propane (Bis-Tris), 3-(cyclohexylamino)-1-propanesuhinic acid (CAPS), 3-(cyclohexylamino)-2-hydroxy-1-propanesuhicic acid (CAPSO), 4-(2-hydroxyethyl)-1-piperazineethanesulfonic acid (HEPES), 3-(N-morpholino)propanesulfonic acid (MOPS), 3-(N-morpholino)-2-hydroxypropanesulfonic acid (MOPSO), piperazine-N,N\'-bis(2-hydroxypropanesulfonic acid (POPSO), N-[Tris(hydroxymethyl)methyl]-3-amino propanesulfonic acid (TAPS), N-[Tris(hydroxymethyl)methyl]-3-amino-2-hyidroxypropansulfonic acid (TAPSO), N-[Tris(hydroxymethyl)methyl]-2-aminoethanesulfonic acid (TES), N,N-bis(2-hydroxyethyl)glycine (Bicine), N-[tris(hydroxymethyl)methyl]glycine (Tricine), N-2-acetamido-2-iminodiacetic acid (ADA), N-(2-acetamido)-2-aminoethanesulfonic acid (ACES), piperazine-1,4-bis(2-ethanesulfonic acid) (PIPES), bicarbonate, phosphate, or any combination thereof.

The inclusion of one or more of such optional but preferred buffers is desirable to control the pH of the formulations, since it has been found that the stability of isolated nucleic is optimally maintained in a pH range of about 5 to 7. Preferably, the one or more buffers employed in the disclosed compositions are chosen to provide a significant buffering capacity in the range from a pH of about 6 to a pH of about 8, more preferably within a pH range of about 6 to about 7, and more preferably still, within a pH range of about 6.2 to about 6.8.

Compositions for preparing populations of nucleic acids from a biological sample for the purpose of assaying and/or quantitating the presence of Influenza A H1N1 subtype-specific nucleic acids from within such a population may also further optionally include one or more additional compounds or reagents including, without limitation, cationic functionalized zwitterionic compounds such as betaines (including, without limitation, N,N,N-trimethylglycine, cocamidopropyl betaine, and the like), albuminoids (including, without limitation, ovalbumin, and the serum albumins of bovine, equine, or human origin), and osmolytes (including, without limitation, trimethylamine N-oxide (TMAO), dimethylsulfoniopropionate, sarcosine, and saccharides or sugar alcohols including, without limitation, trehalose, maltose, rhamnose, sucrose, arabinose, fucose, mannitol, sorbitol, adonitol, and the like).

The compositions of the present invention will typically at least substantially inactivate, and preferably entirely inactivate, any endogenous or exogenous RNAses or DNAses present in the sample, such that the nucleic acids of the sample are substantially free of any degradation, and preferably do not degrade, or lose integrity, during collection, lysis, storage, transport, and/or in vitro or in vivo nucleic acid hybridization, detection, quantitation, and/or amplification analyses.

Exemplary formulations of suitable isolation, stabilization, storage, and/or transport solutions for preserving the integrity of the biological samples used in the practice of the present invention include, without limitation, compositions such as those set forth in commonly co-owned U.S. patent application Ser. No. 12/243,949, filed Oct. 1, 2008 (the entire contents of which is specifically incorporated herein in its entirety by express reference thereto).

In certain embodiments, compositions containing sample of polynucleotides suspected of containing nucleic acids specific for the H1N1 subtype of Influenza A and or B viruses will preferably be selected to permit stabilization of the target nucleic acids to the extent that they either remain at least substantially non-degraded (i.e., at least substantially stable) even upon prolonged storage of the composition at ambient, refrigerator, or sub-zero temperatures. It will be desirable that this stability provides that at least about 70%, at least about 85%, more preferably at least about 90%, more preferably at least about 95%, or even more preferably, at least about 98% of the polynucleotides contained within the stored sample will not be degraded upon prolonged storage of the sample. In certain embodiments, substantially all of the polynucleotides contained within the sample will be stabilized such that the original integrity of the polynucleotides is preserved during the collection, lysis, storage, and transport of the processed sample.

In particular embodiments, the method will preferably provide a population of nucleic acids prepared from a biological sample in which less than about 15% of the polynucleotides contained in the sample will be degraded during the collection, lysis, storage, and transport of the sample after it has been stored in the composition at a temperature of from −20° C. to about 40° C. for a period of at least 24, 48, 72, or 96 hrs or longer after the sample was initially introduced into the composition.

The polynucleotide compositions of the present invention, and particularly those useful in the detection of Influenza virus A- and/or B-specific nucleic acid sequences (including, for example, Influenza A H1N1 subtype viral-specific nucleic acids), preferably contain at least a single primer, or alternatively, two or more primers (e.g., "forward" and "reverse" primers) that may be used to facilitate amplification of the particular target nucleic acid sequence to be amplified. Exemplary primers useful in the practice of the invention include, but are in no way limited to, those primer sequences that specifically bind to the target nucleic acid sequence itself or to one or more regions immediately upstream (5') and or downstream (3') of the actual target nucleic sequence. In illustrative embodiments, the target sequence will also contain at least a first region to which a first detection probe (including, without limitation, luminescent, fluorescent, chemiluminescent, or FRET probes as described herein) specifically binds.

The polynucleotides useful in the preparation of H1N1-specific probes and/or primer sequences described herein may also further optionally include one or more native, synthetic, homologous, heterologous, or hybrid promoter(s), enhancer(s), regulatory element(s), linker(s), spacer(s), binding domain(s), or transcription activation site(s), etc.

In some embodiments, it may be desirable to provide reagent mixtures that include more than a single pair of amplification primers and a detection probe that is specific for a given target nucleic acid sequence. For example, when it is desirable to determine the presence of two or more different types of influenza virus, the composition of the invention may be formulated to contain a first pair of amplification primers that specifically bind to at least a first target region of an Influenza A-specific polynucleotide, and a second pair of amplification primers that specifically bind to at least a first target region of an Influenza B-specific polynucleotide.

Alternatively, when it is desirable to determine the presence of two or more different subtypes of Influenza A virus, the composition of the invention may be formulated to contain a first pair of amplification primers that specifically bind to at least a first target region of a particular Influenza A subtype-specific polynucleotide, and a second pair of amplification primers that specifically bind to at least a first target region of a second, distinct, Influenza A subtype-specific polynucleotide.

For detection of the particular amplification product(s) produced from such compositions, the compositions will also further include a first detection probe that specifically binds to the amplification product produced from the first pair of amplification primers, and a second distinct detection probe that specifically binds to the amplification product produced from the second pair of amplification primers. In such compositions, it is preferable that the two detection probes be distinct, such that each of the probes (if specifically bound to a target in the resulting amplification mixture) may be individually detectable using conventional methodologies. Such probe distinctiveness is readily achievable in the conventional arts, using, for example, detection probes that include detection moieties that fluoresce at two distinctly-different wavelengths.

In some aspects of the invention, the amplification and/or detection of target nucleic acids may be done sequentially, while in other aspects, it may be desirable to amplify and/or detection multiple target nucleic acids simultaneously. For example, a given biological sample could first be screened for the presence of Influenza B-specific target sequence(s), and if none are found, the sample then secondarily screened for the presence of Influenza A-specific target sequence(s). Should an Influenza A-specific target sequence be identified in such reactions, a subsequent analysis could be performed to determine whether the Influenza A virus so detected was of a particular subtype, such as, for example, the H1N1 subtype. Should an Influenza A H1N1 subtype-specific target nucleic acid be detected using such methods, additional analyses could also be performed (either simultaneously or sequentially) on the sample to determine if the sample contained an Influenza A H1N1 subtype strain that is known to be (or suspected of being) a causal agent of swine flu.

Polynucleotide and Oligonucleotide Compositions

In one embodiment, the present invention provides oligonucleotide probes and primer sequences specific for Influenza virus, and in particular, Influenza A virus-specific nucleic acid segments. In illustrative embodiments, exemplary oligonucleotide primer sequences are disclosed that are useful in the detection and amplification of nucleic acid segments that are unique to particular types, subtypes and/or strains on Influenza virus, including, without limitation, nucleic acid segments that are unique to (and therefore considered diagnostic of) particular strains of Influenza A H1N1 virus suspected of being causal agents for Swine flu, and the 2009 pandemic swine flu in particular. In additional embodiments, exemplary oligonucleotide detection probe sequences are disclosed that are particularly useful in the detection and quantitation of amplification products arising from such polynucleotides. Detection of these products when indicative of the presence of these Influenza A H1N1 virus-specific polynucleotides in a clinical sample can provide clinical diagnosticians and other medical professionals with a means for predicting and/or confirming the likelihood of particular Influenza A H1N1 virus infection in patients from whom such samples are collected. Such information may also be useful in the management of care for such individuals, and may also serve as molecular markers for determining the extent, significance, and/or rate of disease progression.

The oligonucleotide primers and probes of the present invention are designed for the selective amplification and detection of Influenza A H1N1 virus-encoding nucleic acid segments, and Influenza A virus (H1N1 swine flu 2009)-encoding polynucleotides in particular. The disclosed primer sequences are suitable for use in hybridization methods, and in DNA amplification methods such as PCR-based amplification methods (including, for example, real-time PCR analyses). Likewise, the disclosed oligonucleotide detection probes are suitable for labeling with an appropriate label means for detection and quantitation of the products resulting from the amplification of nucleic acids using one or more pairs of the amplification primers disclosed herein.

In general, the oligonucleotide probes and primers finding particular utility in the practice of the disclosed methods should be of sufficient length to selectively hybridize to a complementary nucleic acid sequence, such as for example, a region of viral DNA obtained from a clinical isolate of a mammalian patient that is suspected of having, or at risk for developing, an influenza virus infection, and an Influenza A H1N1 viral infection in particular.

In particular, oligonucleotide primers and probes are selected such that the selectively hybridize to specific complementary nucleic acid sequences upstream and downstream of a region of DNA that encompasses a nucleic acid sequence from Influenza A H1N1 virus that is diagnostic of Influenza A H1N1 viral genomic sequence, and in particular, a nucleic acid sequence from an Influenza A H1N1 virus that is causal or suspected of being causal of a pandemic flu outbreak, such as for example, the 2009 pandemic swine flu outbreak that has been identified as being caused by particular strains of Influenza virus A H1N1. The selection of oligonucleotide probe and primer lengths is a process well-known in the molecular biological arts, and depends upon a number of parameters.

For most embodiments, the inventor contemplates that the length of the selected probe and primer compositions of the invention will preferably be less than about 50 to 60 or so nucleotides in length, and more preferably, will be less than about 40 to 45 or so nucleotides in length, while other probes and primers of the invention may be on the order of about 30 to 35 or so nucleotides in length. In some embodiments, the length of the selected oligonucleotide primer sequences (e.g., "forward" and "reverse" primers) and/or the length of the selected detection probe sequences (e.g., "anchor" and "sensor" probes), will likely be on the order of about 20 to 30 or so nucleotides in length, although in some cases, the sizes of particular probes and primer sequences may be larger than that, and on the order of about 60 to 70 nucleotides in length. Alternatively, in some embodiments, it may be desirable to employ shorter probe and/or primer sequences, and as such, the oligonucleotides selected for practice of the invention may be on the order of about 15 to 20 or so nucleotides in length or even slightly shorter in some embodiments.

In the context of the present application, it is understood that all intermediate oligonucleotide lengths within the various ranges stated herein are contemplated to expressly fall within the scope of the present invention. To that end, oligonucleotides that are less than about 60, less than about 59, less than about 58, less than about 57, less than about 56, etc. are expressly within the scope of the present disclosure, as are oligonucleotides that are less than about 50, less than about 49, less than about 48, less than about 47, less than about 46, etc., as well as oligonucleotides that are less than about less than about 40, less than about 39, less than about 38, less than about 37, less than about 36, etc. and so forth.

Influenza Virus A H1N1-Specific Amplification Primers

In the practice of the invention, forward and reverse amplification primers for use in the amplification of Influenza A H1N1 virus-specific polynucleotide sequences, and Influenza A (H1N1 Swine flu 2009) virus-encoding polynucleotide sequences in specific, preferably include at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 or more contiguous nucleic acids from any one of the "forward" oligonucleotide primer sequence disclosed in SEQ ID NO:51 or the "reverse" oligonucleotide primer sequence disclosed in SEQ ID NO:52; or from oligonucleotide sequences that are at least about 95% identical to the "forward" oligonucleotide primer sequence disclosed in SEQ ID NO:51, or the "reverse" oligonucleotide primer sequence disclosed in SEQ ID NO:52; or even from oligonucleotide sequences that are at least about 98% identical to the "forward" oligonucleotide primer sequence disclosed in SEQ ID NO:51, or the "reverse" oligonucleotide primer sequence disclosed in SEQ ID NO:52.

In other embodiments, the preferred oligonucleotide forward and reverse amplification primer sequences of the invention may comprise, consist essentially of or alternatively consist of, the "forward" oligonucleotide primer sequence disclosed in SEQ ID NO:51 and the "reverse" oligonucleotide primer sequence disclosed in SEQ ID NO:52

In yet additional embodiments, the forward and reverse amplification primer compositions preferred for the practice of the methods of the present invention may consist of a nucleic acid sequence that represents a contiguous nucleic acid sequence of about 6, about 7, about 8, about 9, about 10, about 11, about 12, about 13, about 14, or about 15, or more nucleotides as disclosed in SEQ ID NO:51 or SEQ ID NO:52.

Influenza A Virus-Specific Detection Probes

In the practice of the invention, detection probes for use in the detection of Influenza A H1N1 virus-specific polynucleotide sequences, and Influenza A (H1N1 Swine flu 2009) virus-encoding polynucleotide sequences in specific, using PCR, Real-time PCR, and/or FRET-based thermal cycling analyses described herein, will preferably include at least about 6, at least about 7, at least about 8, at least about 9, at least about 10, at least about 11, at least about 12, at least about 13, at least about 14, or at least about 15 or more contiguous nucleic acids from the oligonucleotide detection probe sequence disclosed in SEQ ID NO:53; or from oligonucleotide sequences that are at least about 95% identical to the oligonucleotide detection probe sequence disclosed in SEQ ID NO:53; or even from oligonucleotide sequences that are at least about 98% identical to the oligonucleotide probe sequence disclosed in SEQ ID NO:53.

In yet additional embodiments, the detection probes of the present invention will preferably include a pair of probes, the first of which is an "anchor" probe, and the second of which is a "sensor" probe as described herein. Such probe pairs are specifically contemplated for use in FRET-based detection methodologies. In such embodiments, the probe compositions preferred for the practice of the methods of the present invention in a FRET analysis may include a pair of detection probes, the first or second members of which may comprise, consist essentially of, or alternatively consist of, a nucleic acid sequence that represents a contiguous nucleic acid sequence of about 6, about 7, about 8, about 9, about 10, about 11, about 12, about 13, about 14, or about 15, or more contiguous nucleotides from SEQ ID NO:53.

As used herein, "nucleic acid" or "polynucleotide" compositions include, but are not limited to, those that contain either single-stranded or double-stranded polynucleotides, such as for example, deoxyribonucleic acids (DNA), ribonucleic acids (RNA), peptide nucleic acids (PNA), or any combinations or derivatives thereof (including, e.g., genomic, extragenomic, plasmid, cosmid, recombinant, artificial, and/or synthetic). Such sequences may be coding or non-coding sequences, sense, non-sense, or anti-sense sequences, and may, but need not, be present within one or more populations or pluralities of polynucleotides (either of the present invention, and a polynucleotide may, but need not, be linked to other molecules and/or support materials.

Likewise, polynucleotides of the present invention, and particularly those functioning as probes and/or primers specific for one or more particular types, subtypes, or strains of Influenza virus, need not be identical, or even substantially homologous to the particular sequences employed in the various embodiments of the invention illustrated herein. While the inventors have illustrated the use of particular probe and primer sequences as tools for identifying, amplifying, and quantitating a particular Influenza virus subtype or strain, such primers and/or probe sequences need not contain the particular nucleotide sequences employed in the illustrative examples provided herein.

In fact, in certain circumstances, polynucleotides useful as probe and/or primer sequences in the disclosed Influenza virus detection/identification system may include any suitable sequences that may be obtained, prepared, modified, or synthesized for such purpose. Moreover, it is preferable that the probe and primer sequences utilized specifically hybridize to their particular target sequences, and do not share significant homology or substantially bind to other viral, bacterial, or fungal species, or to the genome of the host organism from which the biological sample was originally obtained. Likewise, it is desirable that the various probes and primer compositions used for the detection of particular subtypes and/or strains of a given Influenza virus also not cross-react, or hybridize to other, or non-related nucleic acids that may also be present in the sample under assay.

As noted herein, the invention provides detection probes that contain at least a first sequence domain that specifically hybridizes (i.e., binds) to a suitably-detectable probe, including, without limitation, molecularly-labeled probes and derivatives thereof. Exemplary labeled probes are those that include radioactive, luminescent, chemiluminescent, fluorescent, enzymatic, magnetic, or spin-resonance labels known to those of ordinary skill in the molecular arts. In illustrative embodiments, the labeled probe contains at least a first minor groove binder.

In certain embodiments, to facilitate the binding of conventional detectable-label probes, the detection probes of the invention will contain at least a first sequence domain of from about 10 to about 60 nucleotides in length that specifically binds to at least a first detectable probe. While the first sequence domain may be of any practical length within the entirety of the carrier sequence, preferably, the first sequence domain will be from about 12 to about 50 nucleotides in length; more preferably, from about 14 to about 45 nucleotides in length; still more preferably, from about 16 to about 40 or so nucleotides in length, and more preferably still, from about 18 to about 30 or so nucleotides in length.

As such, all intermediate lengths of probe-hybridizing sequence domains are contemplated to fall within the scope of the present disclosure, including, without limitation, probe-binding domains that are about 13 nucleotides in length, about 14 nucleotides in length, about 15 nucleotides in length, about 16 nucleotides in length, about 17 nucleotides in length, about 18 nucleotides in length, about 19 nucleotides in length, about 20 nucleotides in length, about 21 nucleotides in length, about 22 nucleotides in length, about 23 nucleotides in length, about 24 nucleotides in length, about 25 nucleotides in length, about 26 nucleotides in length, about 27 nucleotides in length, about 28, or even about 29 or 30 or so nucleotides in length.

In exemplary embodiments, the amplification primers and detection probes may be prepared by one or more suitable molecular biology techniques, including, e.g., by the in vitro transcription of a polynucleotide that includes the sequence, or alternatively, includes a nucleic acid sequence that is complementary to the sequence.

The methods for nucleic acid hybridization are considered routine to those of ordinary skill in the molecular biological arts, and as such, a detailed discussion of analytical methods employing them need not be provided herein. However, as a guidance, "moderately stringent" hybridization conditions popularized by Southern et al. are generally considered in the art to include, e.g., pre-washing in a solution containing about 5× standard sodium citrate buffer (SSC), 0.5% sodium dodecyl sulfate (SDS), 1.0 mM ethylenediaminetetraacetic acid (EDTA) (e.g., pH 8.0); hybridizing at a temperature of from about 50° C. to about 60° C. in 5×SSC overnight; followed by washing twice at about 60 to 65° C. for 20 min. with each of 2×, 0.5× and 0.2×SSC containing 0.1% SDS). Likewise, "stringent" hybridization conditions typically include, e.g., pre-washing in a solution containing about 5×SSC, 0.5% SDS, 1.0 mM EDTA (pH 8.0); hybridizing at a temperature of from about 60° C. to about 70° C. in 5×SSC overnight; followed by washing twice at about 65 to 70° C. for 20 min. with each of 2×, 0.5× and 0.2×SSC containing 0.1% SDS). Similarly, representative examples of "highly-stringent" hybridization conditions include, but are not limited to, pre-washing in a solution containing about 5×SSC, 0.5% SDS, 1.0 mM EDTA (pH 8.0); hybridizing at a temperature of from about 70° C. to about 75° C. in 5×SSC overnight; followed by washing twice at about 70° C. to about 75° C. for 20 min. with each of 2×, 0.5× and 0.2×SSC containing 0.1% SDS).

It will also be appreciated by those of ordinary skill in the art that, as a result of the degeneracy of the genetic code, there are many nucleotide sequences that encode a given primary amino acid sequence. Some of these polynucleotides bear minimal homology to the nucleotide sequence of any native gene. Nonetheless, polynucleotides that vary due to differences in codon usage are specifically contemplated by the present invention.

Detection probes and amplification primers may be prepared by conventional molecular biology recombination methodologies, or alternatively synthesized in whole or in part by conventional methods known in the art, including chemical synthesis (e.g., solid phase phosphoramidite chemical synthesis) and the like. Modifications in a polynucleotide sequence may also be introduced using standard mutagenesis techniques, such as oligonucleotide-directed site-specific mutagenesis. RNA molecules for use as detection probes or primers may also be directly synthesized, or alternatively, be prepared by in vitro or in vivo transcription of DNA sequences using suitable systems (such as T3, T7, and SP6 polymerases and the like).

Polynucleotides of the present invention may be modified to increase stability either in vitro and/or in vivo. Such modifications include, without limitation, the addition of flanking sequences at the 5'-end, 3'-end, or both; the use of phosphorothioate or 2'-o-methyl rather than phosphodiesterase linkages in the backbone; and/or the inclusion of nontraditional bases such as inosine, queosine and wybutosine, as well as acetyl-, methyl-, thio-, or otherwise-modified forms of adenine, cytidine, guanine, thymine and uridine, or any combination thereof.

Nucleotide sequences as described herein may be joined or linked to a variety of other nucleotide sequences using established recombinant techniques. For example, a polynucleotide useful as an amplification probe or detection primer may be produced by cloning into any of a variety of cloning vectors, including one or more of plasmids, phagemids, lambda phage derivatives and cosmids. Vectors of particular interest include expression vectors, replication vectors, probe generation vectors, and sequencing vectors. In general, a vector will contain an origin of replication functional in at least one organism, convenient restriction endonuclease sites and one or more selectable markers. Other elements will depend upon the desired use, and will be apparent to those of ordinary skill in the art. Alternatively, probe and primer-specific oligonucleotide sequences may be prepared through one or more template-dependent, or amplicon-directed recombinant production methodologies that are known to those of ordinary skill in the arts.

In particular embodiments, the present invention provides polynucleotide compositions that may be added to the disclosed collection/storage/transport media to provide one or more amplification primer(s) and or detection probe(s) to analyze and/or characterize a population of target polynucleotides isolated, for example, from a biological sample or specimen. Such polynucleotide compositions may contain one or more sequence domains to which specific polymerases may bind, and may serve as suitable amplification primers, and/or detection probes.

Oligonucleotide primers and probes of the present invention may be designed for the selective amplification and detection of one or more specific target nucleic acids, including, for example, those sequences that are specific for a single strain, subtype, or type of Influenza virus. Such primer sequences are suitable for use in hybridization methods, and in amplification methods such as PCR-based amplification methods (including, for example, real-time PCR analyses, RT-PCR and the like). Likewise, the disclosed oligonucleotide detection probes are suitable for labeling with an appropriate label for detection and quantitation of the products resulting from the amplification of nucleic acids using one or more pairs of the amplification primers disclosed herein.

When labeled with appropriate markers, oligonucleotide detection probes are particularly suited for fluorescence-based detection of Influenza virus strain- or subtype-specific nucleotide sequences including, for example, via FRET-based analyses. FRET-labeled detection probes are particularly useful in fluorimetric detection methodologies, including for example, the FRET-based microvolume fluorimetry devices. Use of one or more amplification and detection oligonucleotides is particularly contemplated in the combined real-time PCR/microvolume fluorimetry FRET-based methodologies (real-time PCR-FRET), and particularly in analyses facilitated by the "LightCycler®" instrumentation as developed by Idaho Technology, Inc. (Salt Lake City, Utah, USA), and now manufactured and marketed by Roche Applied Science (Indianapolis, Ind., USA).

Real-Time PCR-Based FRET Detection

As noted above, in certain aspects, it may be desirable to amplify and quantitate target nucleic acid segments from among a population of polynucleotides isolated from a biological sample in near- or real-time based assays. Real-time PCR and FRET methodologies have been well described in the literature (see, for example, U.S. Pat. Nos. 4,996,143, 5,565,322, 5,849,489, 6,162,603, each of which is specifically incorporated herein in its entirety by express reference thereto). The LightCycler® platform represents a significant breakthrough in genetic mutation screening and analysis. This system incorporates a rapid, air-driven thermal cycling instrument that can perform 30 polymerase chain reaction (PCR) cycles in less than 20 minutes. It utilizes an in-line microvolume fluorimeter to detect and quantitate fluorescently-labeled hybridization probes, and provides the data necessary for determination of melting curve analyses. The LightCycler® platform provides innovative instrumentation to facilitate the development of genetic analysis tools, and to provide a rapid, qualitative method for the assay of specific nucleotide sequences, and genetic mutations. Detailed application of the instrumentation in amplification and detection methods may be found on the manufacturer's website, and in product application manuals. This technology has also been described, including for example PCT Intl. Appl. Publ. Nos. WO 97/46707, WO 97/46714 and WO 97/46712 (each of which is specifically incorporated in its entirety by express reference thereto).

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

The phrase "substantially identical," in the context of two nucleic acids refers to two or more sequences or subsequences that have at least about 90%, preferably 91%, most preferably about 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide residue identity, when compared and aligned for maximum correspondence, as measured using a sequence comparison algorithm or by visual inspection. Such "substantially identical" sequences are typically considered "homologous," without reference to actual ancestry.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm can then be used to calculate the percent sequence identity for the test sequence(s) relative to the reference sequence, based on the designated program parameters.

Optimal alignment of sequences for comparison can be conducted, e.g., by the local homology algorithm (see e.g., Smith and Waterman, 1981), by the homology alignment algorithm (see e.g., Needleman and Wunsch, 1970), by the search similarity comparison method (see e.g., Pearson and Lipman, 1988), by computerized implementations of algorithms such as GAP, BESTFIT, FASTA, and TFASTA in the Wisconsin Genetics Software Package, Genetics Computer Group, Madison, Wis., USA, or by visual inspection. One example of an algorithm that is suitable for determining percent sequence identity and sequence similarity is the BLAST algorithm (Altschul et al., 1990) and BLOSUM62 scoring matrix (see, e.g., Henikoff and Henikoff, 1989). Software for performing BLAST analyses is publicly available through the National Center for Biotechnology Information (www.ncbi.nlm.nih.gov/).

In addition to calculating percent sequence identity, the BLAST algorithm also performs a statistical analysis of the similarity between two sequences (see, e.g., Karlin and Altschul, 1993). Another example of a useful sequence alignment algorithm is the PILEUP program, which creates a multiple sequence alignment from a group of related sequences using progressive, pairwise alignments. It can also plot a tree showing the clustering relationships used to create the alignment. PILEUP uses a simplification of the progressive alignment comparison method (see e.g., Feng and Doolittle, 1987), and employs a general alignment matrix similar to that described by Higgins and Sharp (1989).

DEFINITIONS

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof that is pharmaceutically acceptable for administration to the relevant animal or acceptable for a diagnostic purpose, as applicable. The use of one or more delivery vehicles for chemical compounds in general, and peptides and epitopes in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed immunogenic compositions.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

As used herein, the term "DNA segment" refers to a DNA molecule that has been isolated free of total genomic DNA of a particular species. Therefore, a DNA segment obtained from a biological sample using one of the compositions disclosed herein, refers to one or more DNA segments that have been isolated away from, or purified free from, total mammalian or human genomic DNA. Included within the term "DNA segment," are DNA segments and smaller fragments of such segments, as well as recombinant vectors, including, for example, plasmids, cosmids, phage, viruses, and the like.

Similarly, the term "RNA segment" refers to an RNA molecule that has been isolated free of total cellular RNA of a particular species. Therefore, RNA segments obtained from a biological sample using one of the compositions disclosed herein, refers to one or more RNA segments (either of native or synthetic origin) that have been isolated away from, or purified free from, other RNAs. Included within the term "RNA segment," are RNA segments and smaller fragments of such segments.

As used herein, the terms "protein," "polypeptide," and "peptide" are used interchangeably, and include molecules that include at least one amide bond linking two or more amino acid residues together. Although used interchangeably, in general, a peptide is a relatively short (e.g., from 2 to about 100 amino acid residues in length) molecule, while a protein or a polypeptide is a relatively longer polymer (e.g., 100 or more residues in length). However, unless specifically defined by a chain length, the terms peptide, polypeptide, and protein are used interchangeably.

As used herein, "sample" includes anything containing or presumed to contain a substance of interest. It thus may be a composition of matter containing nucleic acid, protein, or another biomolecule of interest. The term "sample" can thus encompass a solution, cell, tissue, or population of one of more of the same that includes a population of nucleic acids (genomic DNA, cDNA, RNA, protein, other cellular molecules, etc.). The terms "nucleic acid source," "sample," and "specimen" are used interchangeably herein in a broad sense, and are intended to encompass a variety of biological sources that contain nucleic acids, protein, one or more other biomolecules of interest, or any combination thereof. Exemplary biological samples include, but are not limited to, whole blood, plasma, serum, sputum, urine, stool, white blood cells, red blood cells, buffy coat, swabs (including, without limitation, buccal swabs, throat swabs, vaginal swabs, urethral swabs, cervical swabs, rectal swabs, lesion swabs, abscess swabs, nasopharyngeal swabs, and the like), urine, stool, sputum, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluid from cysts or abcess contents, synovial fluid, vitreous or aqueous humor, eye washes or aspirates, pulmonary lavage or lung aspirates, and organs and tissues, including but not limited to, liver, spleen, kidney, lung, intestine, brain, heart, muscle, pancreas, and the like, and any combination thereof. In some embodiments, the sample may be, or be from, an organism that acts as a vector, such as a mosquito, or tick, or other insect(s).

Tissue culture cells, including explanted material, primary cells, secondary cell lines, and the like, as well as lysates, homogenates, extracts, or materials obtained from any cells, are also within the meaning of the term "biological sample," as used herein. Microorganisms (including, without limitation, prokaryotes such as the archaebacteria and eubacteria; cyanobacteria; fungi, yeasts, molds, actinomycetes; spirochetes, and mycoplasmas); viruses (including, without limitation the Orthohepadnaviruses [including, e.g., hepatitis A, B, and C viruses], human papillomavirus, Flaviviruses [including, e.g., Dengue virus], Lyssaviruses [including, e.g., rabies virus], Morbilliviruses [including, e.g., measles virus], Simplexviruses [including, e.g., herpes simplex virus], Polyomaviruses, Rubulaviruses [including, e.g., mumps virus], Rubiviruses [including, e.g., rubella virus], Varicellovirus [including, e.g., chickenpox virus], rotavirus, coronavirus, cytomegalovirus, adenovirus, adeno-associated virus, baculovirus, parvovirus, retrovirus, vaccinia, poxvirus, and the like), algae, protozoans, protists, plants, bryophytes, and the like, and any combination of any of the foregoing, that may be present on or in a biological sample are also within the scope of the invention, as are any materials obtained from clinical or forensic settings that contain one or more nucleic acids are also within the scope of the invention. The ordinary-skilled artisan will also appreciate that lysates, extracts, or materials obtained from any of the above exemplary biological samples are also within the scope of the invention.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "biological molecule" refers to any molecule found within a cell or produced by a living organism, including viruses. This may include, but is not limited to, nucleic acids, proteins, carbohydrates, and lipids. As used herein, a "cell" refers to the smallest structural unit of an organism that is capable of independent functioning and is included of cytoplasm and various organelles surrounded by a cell membrane. This may include, but is not limited to, cells that function independently such as bacteria and protists, or cells that live within a larger organism such as leukocytes and erythrocytes. As defined herein, a cell may not have a nucleus, such as a mature human red blood cell.

Samples in the practice of the invention can be used fresh, or can be used after being stored for a period of time, or for an extended period of time, including for example, cryopreserved samples and the like, and may include material of clinical, veterinary, environmental or forensic origin, may be isolated from food, beverages, feedstocks, potable water sources, wastewater streams, industrial waste or effluents, natural water sources, soil, airborne sources, pandemic or epidemic populations, epidemiological samples, research materials, pathology specimens, suspected bioterrorism agents, crime scene evidence, and the like.

As used herein, the term "patient" (also interchangeably referred to as "host" or "subject") refers to any host that can serve as a source of one or more of the biological samples or specimens as discussed herein. In certain aspects, the donor will be a vertebrate animal, which is intended to denote any animal species (and preferably, a mammalian species such as a human being). In certain embodiments, a "patient" refers to any animal host, including but not limited to, human and non-human primates, avians, reptiles, amphibians, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals or birds, exotics or zoological specimens, as well as companion animals, pets, and any animal under the care of a veterinary practitioner. The invention may also be used to monitor disease outbreak, progression, and epidemiological statistics for a variety of global populations, including, without limitation, wasting disease in ungulates, tuberculosis, ebola, SARS, and avian influenzas. In certain embodiments, the samples will preferably be of mammalian origin, and more preferably of human origin.

The term "e.g.," as used herein, is used merely by way of example, without limitation intended, and should not be construed as referring only those items explicitly enumerated in the specification.

The term "substantially free" or "essentially free," as used herein, typically means that a composition contains less than about 10 weight percent, preferably less than about 5 weight percent, and more preferably less than about 1 weight percent of a compound. In a preferred embodiment, these terms refer to less than about 0.5 weight percent, more preferably less than about 0.1 weight percent or even less than about 0.01 weight percent. The terms encompass a composition being entirely free of a compound or other stated property, as well. With respect to degradation or deterioration, the term "substantial" may also refer to the above-noted weight percentages, such that preventing substantial degradation would refer to less than about 15 weight percent, less than about 10 weight percent, preferably less than about 5 weight percent, etc., being lost to degradation. In other embodiments, these terms refer to mere percentages rather than weight percentages, such as with respect to the term "substantially non-pathogenic" where the term "substantially" refers to leaving less than about 10 percent, less than about 5 percent, etc., of the pathogenic activity.

As used herein, the term "heterologous" is defined in relation to a predetermined referenced nucleic acid sequence. For example, with respect to a structural gene sequence, a heterologous promoter is defined as a promoter that does not naturally occur adjacent to the referenced structural gene, but which is positioned by the hand of man in one or more laboratory manipulations that are routinely employed by those of ordinary skill in the molecular biological arts. Likewise, a heterologous gene or nucleic acid segment is defined as a gene or nucleic acid segment that does not naturally occur adjacent to the referenced sequence, promoter and/or enhancer element(s), etc.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

The terms "identical" or percent "identity," in the context of two or more nucleic acid or polynucleotide sequences, refer to two or more sequences or subsequences that are the same or have a specified percentage of nucleotides that are the same, when compared and aligned for maximum correspondence over a comparison window, as measured using a sequence comparison algorithm or by manual alignment and visual inspection.

A "primer" or "primer sequence" may include any nucleic acid sequence or segment that selectively hybridizes to a complementary template nucleic acid strand ("target sequence") and functions as an initiation point for the addition of nucleotides to replicate the template strand. Primer sequences of the present invention may be labeled or contain other modifications which allow the detection and/or analysis of amplification products. In addition to serving as initiators for polymerase-mediated duplication of target DNA sequences, primer sequences may also be used for the reverse transcription of template RNAs into corresponding DNAs.

A "target sequence" or "target nucleotide sequence" as used herein includes any nucleotide sequence to which one of said primer sequences hybridizes under conditions that allow an enzyme having polymerase activity to elongate the primer sequence, and thereby replicate the complementary strand.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; H is), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to all amino acid chain lengths, including those of short peptides of from about 2 to about 20 amino acid residues in length, oligopeptides of from about 10 to about 100 amino acid residues in length, and polypeptides including about 100 amino acid residues or more in length. The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5' to 3' order of nucleotides.

As used herein, the term "substantially homologous" encompasses two or more biomolecular sequences that are significantly similar to each other at the primary nucleotide sequence level. For example, in the context of two or more nucleic acid sequences, "substantially homologous" can refer to at least about 75%, preferably at least about 80%, and more preferably at least about 85% or at least about 90% identity, and even more preferably at least about 95%, more preferably at least about 97% identical, more preferably at least about 98% identical, more preferably at least about 99% identical, and even more preferably still, at least substantially or entirely 100% identical (i.e., "invariant").

Likewise, as used herein, the term "substantially identical" encompasses two or more biomolecular sequences (and in particular polynucleotide sequences) that exhibit a high degree of identity to each other at the nucleotide level. For example, in the context of two or more nucleic acid sequences, "substantially identical" can refer to sequences that at least about 80%, and more preferably at least about 85% or at least about 90% identical to each other, and even more preferably at least about 95%, more preferably at least about 97% identical, more preferably at least about 98% identical, more preferably at least about 99% identical, and even more preferably still, at least substantially or entirely 100% identical (i.e., "non-degenerate").

The term "recombinant" indicates that the material (e.g., a polynucleotide or a polypeptide) has been artificially or synthetically (non-naturally) altered by human intervention. The alteration can be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and in reading frame. Since enhancers generally function when separated from the promoter by several kilobases and intronic sequences may be of variable lengths; however, some polynucleotide elements may be operably linked but not contiguous.

"Transcriptional unit" refers to a polynucleotide sequence that includes at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

As used herein, "an effective amount" would be understood by those of ordinary skill in the art to provide a therapeutic, prophylactic, or otherwise beneficial effect against the organism, its infection, or the symptoms of the organism or its infection, or any combination thereof.

As used herein, the term "rapid" encompasses a period of time that is shorter than the time involved for the conventional method of detection and identification, which typically involve culturing the target specimen, shipping it to the laboratory (usually in a cold chain), assaying the extracted nucleic acid, and then analyzing the results of the assay. In certain embodiments, the time to use the components of the diagnostic tools, i.e., perform the methods from beginning the collecting through the assaying, is less than about 24 hours, more preferably less than about 12 hours, even more preferably less than about 6 hours, and yet more preferably less than about 3 hours. In preferred embodiments, the assaying is fully conducted within about 30 minutes to 3 hours, preferably about 45 minutes to 150 minutes, or more preferably about 60 minutes to 2 hours of the collecting. In one preferred embodiment, the assaying is completed within about 5 to 150 minutes, preferably about 10 to 120 minutes, of the collecting. In another embodiment, the assaying is conducted within about 1 to 120 minutes, preferably about 5 to 90 minutes, of the collecting. The identifying can occur, in certain preferred embodiments, within the same time frame from the collecting as those set forth above for the assaying.

As used herein, the term "efficient" encompasses a comparison between the diagnostic tool and methods of the present invention compared to the tools and methods in the art, which require one or more additional steps including ensuring the viability of the culture sample, shipping the sample to a remote location away from the collection site, or both. The conventional methods typically require transport to a laboratory facility of sufficient security to handle hazardous pathogens, while the invention safely moves the detection assay into the field for rapid detection and surveillance.

As used herein, the "target specimen" is a host of the organism from which the biological sample is collected for detection, identification, or both. As used herein, the term "patient" (interchangeably referred to herein as "host," or "subject") refers to any host that can be infected with an infective organism, such as, e.g., influenza.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

The term "pathogen" is defined herein as any sort of infectious agent, including e.g., viruses, prions, protozoans, parasites, as well as microbes such as bacteria, yeast, molds, fungi, and the like.

As used herein, the term "plasmid" refers to a genetic construct that is composed of genetic material (i.e., nucleic acids). Typically, a plasmid contains an origin of replication that is functional in bacterial host cells, e.g., *Escherichia coli*, and selectable markers for detecting bacterial host cells including the plasmid. Plasmids of the present invention may include genetic elements as described herein arranged such that an inserted coding sequence can be transcribed and translated in eukaryotic cells. In addition, the plasmid may include one or more nucleic acids derived from natural or artificial sources.

As used herein, the term "kit" may be used to describe variations of the portable, self-contained enclosure that includes at least one set of components to conduct the methods of the invention including collecting a sample, fixing the sample, extracting nucleic acid from the sample, assaying the nucleic acid, e.g., to detect the presence of a biological organism, and optionally analyzing the information collected in the assay to identify the biological organism. The "kit" may be extremely portable, such as the size of a briefcase, may be larger. Larger kits can be the size of a steamer trunk, e.g., about 1 to 3 feet wide, about 3 to 8 feet long, and about 1 to 4 feet deep. Even larger kits can be used according to the invention, such as a van or 18 foot truck with the equipment loose, tied down, or releasably attached, or permanently attached, to the movable structure. Preferably, the kits are sufficiently small to readily fit onto an aircraft and a movable ground-based vehicle for ready transport to the site of an epidemic in virtually any location. A mobile medical unit or hospital may contain the kit on board, or may function as the portable enclosure of the kit of the invention.

The term "a sequence essentially as set forth in SEQ ID NO:X" means that the sequence substantially corresponds to a portion of SEQ ID NO:X and has relatively few nucleotides (or amino acids in the case of polypeptide sequences) that are not identical to, or a biologically functional equivalent of, the nucleotides (or amino acids) of SEQ ID NO:X. The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

Suitable standard hybridization conditions for the present invention include, for example, hybridization in 50% formamide, 5×Denhardts' solution, 5×SSC, 25 mM sodium phosphate, 0.1% SDS and 100 µg/ml of denatured salmon sperm DNA at 42° C. for 16 h followed by 1 hr sequential washes with 0.1×SSC, 0.1% SDS solution at 60° C. to remove the desired amount of background signal. Lower stringency hybridization conditions for the present invention include, for example, hybridization in 35% formamide, 5×Denhardts' solution, 5×SSC, 25 mM sodium phosphate, 0.1% SDS and 100 µg/ml denatured salmon sperm DNA or *E. coli* DNA at 42° C. for 16 h followed by sequential washes with 0.8×SSC, 0.1% SDS at 55° C. Those of skill in the art will recognize that conditions can be readily adjusted to obtain the desired level of stringency.

Naturally, the present invention also encompasses DNA segments that are complementary, or essentially complementary, to one or more of the specific sequences set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 25-mer, the probes correspond to bases 1 to 25, 2 to 26, 3 to 27 and so on. For a 45-mer, the probes correspond to bases 1 to 45, 2 to 46, 3 to 47 and so on. For a 60-mer, the probes correspond to bases 1 to 60, 2 to 61, 3 to 62 and so on.

In certain embodiments, it will be advantageous to employ nucleic acid sequences of the present invention in combination with an appropriate detectable marker (i.e., a "label,") for determining hybridization. A wide variety of appropriate indicator compounds and compositions are known in the art, including, without limitation, fluorescent, radioactive, enzymatic or other ligands, such as avidin/biotin, etc., which are capable of being detected. In particular embodiments, one may desire to employ a fluorescent label or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences.

In general, it is envisioned that the hybridization probes described herein will be useful both as reagents in solution hybridization, as in PCR, for detection of particular nucleotides, as well as in embodiments employing a solid phase.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual inspection. Alternatively, the detection may involve indirect identification of the product via chemiluminescence, radioactive scintigraphy of incorporated radiolabel or fluorescent label or even via a system using electrical or thermal impulse signals.

A number of template dependent processes are available to amplify the marker sequences present in a given template sample. One of the best-known amplification methods is the polymerase chain reaction (referred to as PCR) which is described in detail in U.S. Pat. Nos. 4,683,195, 4,683,202 and 4,800,159, and each incorporated herein by reference in entirety.

Another method for amplification is the ligase chain reaction ("LCR"), disclosed, e.g., in EPA No. 320 308, and U.S. Pat. No. 4,883,750, each of which is incorporated herein in its entirety by express reference thereto.

An isothermal amplification method, in which restriction endonucleases and ligases are used to achieve the amplification of target molecules that contain nucleotide 5'-[α-thio]-triphosphates in one strand of a restriction site may also be useful in the amplification of nucleic acids in the present invention.

Strand Displacement Amplification (SDA) is another method of carrying out isothermal amplification of nucleic acids that involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Methods based on ligation of two (or more) oligonucleotides in the presence of nucleic acid having the sequence of the resulting "di-oligonucleotide," thereby amplifying the di-oligonucleotide, may also be used in the amplification of the present invention.

Following any amplification, it may be desirable to separate the amplification product from the template and the excess primer for determining whether specific amplification has occurred. In one embodiment, amplification products are separated by agarose, agarose-acrylamide or polyacrylamide gel electrophoresis using conventional methods that are known to those of ordinary skill in the art.

The term "about," as used herein, should generally be understood to mean "approximately", and typically refers to numbers approximately equal to a given number recited within a range of numerals. Moreover, all numerical ranges herein should be understood to include each whole integer within the range.

In accordance with long standing patent law convention, the words "a" and "an" when used in this application, including the claims, denotes "one or more."

EXAMPLES

The following examples are included to demonstrate illustrative embodiments of the invention. It should be appreciated by those of ordinary skill in the art that the techniques disclosed in the examples that follow represent techniques discovered to function well in the practice of the invention, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

A Protocol for Collection and Extraction of Genomic Material in the Field

Oropharyngeal, cloacal, nasal and tracheal swabs of a subject, such as a chicken, are taken. Swabs are suspended in 1.5 ml of BHI and extracted with an RNeasy Mini® kit, (Qiagen, Valencia, Calif., USA; MagMax Kit, Ambion, Austin, Tex., USA). The RNA is eluted in 60 µl of RNase®-free water.

Example 2

A Protocol for Identification of Genomic Material

Collection of Clinical Samples and Virology—

All original primary specimens (throat swab/nasal washes) and cultured samples used in this study were collected over 7 (99/00, 00/01, 01/02, 02/03, 03/04, 04/05, and 05/06) and 3 (03/04; 04/05, and 05/06) influenza seasons, respectively, under the auspices of the Department of Defense Global Emerging Infectious Surveillance (DoD-GEIS) network. Primary specimens were collected within the first 48-72 hours of symptom onset from patients presenting with a fever ≥100.5° F. oral, and cough or sore throat. Dacron throat swab specimens were submerged in 3.0 ml viral transport media (M4 MicroTest Multi-Microbe Media). Submerged throat swabs and saline nasal wash material (5 ml) were shipped on dry ice to Brooks City Base, San Antonio, Tex. Propagation of influenza viruses from primary specimens was achieved using the centrifugation-enhanced shell-vial culture technique followed by typing using influenza virus A or B specific monoclonal antibodies (Chemicon International, Temecula, Calif., USA) per manufacturer's recommendations and fluorescent microscopy. (Daum L T, Canas L C, Smith C B, et al., Genetic and antigenic analysis of the first A/New Caledonia/20/99-like H1N1 influenza isolates reported in the Americas, *Emerg. Infect. Dis.,* 8:408-412, 2002). Aliquots (0.25 ml) of primary specimens (before and after culturing) served as source of specimen RNA.

Extraction of RNA:

RNA extraction was achieved using the M48 automated bead-based extraction robot with the MagAttract™ Virus Mini M48 kit (Qiagen) per manufacturer's protocols, eluted in 50 µl of Elution Buffer and stored at −80° C. until used.

Genomic Primer/Probe Design:

Primer/probe design was based upon sequence data obtained from the Los Alamos National Laboratory and Department of Defense data bases. Type-specific (Influenza A and B) assays target a highly conserved region of the matrix protein (MP) gene, and were designed based on 100 and 50 alignments common to all 16 influenza A virus subtypes and both influenza B lineages (B/Victoria and B/Yamagata), respectively. H1, H3, and H5 influenza A subtype specific assays target conserved regions of the respective hemagglutinins. H1 primer/probe sequence alignment was achieved using 51 geographically diverse strains obtained during the 2005/06 and 2006/07 influenza seasons including the A/New Caledonia/20/99 vaccine strain. H3 primer/probe sequence alignment was achieved using 140 H3N2 field strains collected between 2004 and 2006. H5 primer/probe sequence design was based upon alignment analysis of 22 H5N1 clinical isolates representing clades 1 and 2 (subclades 1, 2 and 3) viruses. All primers and probes were procured from Applied Biosystems (Foster City, Calif., USA).

Real-Time RT-PCR Platforms:

The laboratory-based LightCycler 2.0 instrument (Roche Molecular Diagnostics, Indianapolis, Ind., USA), and its lightweight portable (50-lb) version, the Ruggedized Advanced Pathogen Identification Device (R.A.P.I.D., Idaho Technologies, Salt Lake City, Utah, USA), are both 32-well capillary, real-time instruments which employ similar components and operational software. The R.A.P.I.D. is configured within a hardened case, and can be employed remotely (e.g., in the field, or at the point-of-care).

Real-Time RT-PCR Amplification:

Primer and probe sequences are shown in FIG. 5. Primer pair melting points are within 2° C. and anneal/extend at 58-60° C. The respective probes anneal/extend 8-10° C. higher than that of the primers. Thermocycling operates in a rapid, 2-temperature format with annealing and extension (30 seconds) facilitated by the short nature of the respective amplicons. Due to genetic variability in the influenza viral genome, degenerate nucleotides were placed at specific loci.

Real-time amplification was performed in a single step, single reaction vessel format. Using the UltraSense Platinum One-Step Quantitative RT-PCR System (Invitrogen, Carlsbad, Calif., USA), 2 µl RNA was added to 18 µl master mix containing the following components at the indicated final concentrations: 1× reaction buffer, 1× enzyme mixture containing 500 nM of each primer and 300 nM probe labeled at the 5'-end with 6-carboxyfluorescein (FAM) reporter dye and at the 3'-end with a nonfluorescent quencher and minor groove binder. Thermocycling was carried out as follows: 30 minutes at 45° C. and 2 minutes at 95° C. for reverse transcription (RT) and denaturation, respectively, followed by 40 amplification cycles consisting of 95° C. for 5 seconds (denaturation) and 60° C. for 30 seconds (extension). Amplification efficiency was determined using the $C_T$ slope method (cf. FIG. 4B) according to the equation: $E=[10^{(-1/Slope)}-1]\times 100$. All assays described here exhibited greater than 98.5% amplification efficiency.

For each analysis, 'no template' and 'positive' controls were included. Baseline fluorescence for each analysis was manually adjusted to that of the respective 'no template' control reaction. The 'positive' control (0.1 ng cRNA) gives rise to an increase in fluorescence intensity relative to the no template baseline ($C_T$ value between 18 and 22). A 'positive' unknown is defined as amplification exceeding baseline fluorescence with a corresponding $C_T$ value not exceeding 36 in a 40-cycle run. All original, i.e., uncultured specimens, and cultured samples reported here using both platforms exhibited $C_T$ range values of 26 to 35 (n=144, mean=31.5) and 17 to 27 (n=407, mean=23), respectively.

Generation of cRNA Target Templates:

Reverse and forward primers for in vitro generation of target complementary RNA (cRNA) templates corresponding to Influenza type (A/B) and Influenza A subtype (H1, H3, and H5) RNA sequences are shown in FIG. 5.

Briefly, traditional RT-PCR was carried out as follows: 5 µl viral RNA was added to a 45-µl master mix containing the following components at the indicated final concentrations: 1× reaction buffer with 1.6 mM $MgSO_4$, 1× enzyme mixture containing 400 nM HA or MP primer pairs using the SuperScript III One-Step RT-PCR System (Invitrogen). Reverse transcription was carried out at 50° C. for 30 minutes followed by a 'hot start' step (2 minutes) at 95° C. Thermocycling (40 amplification cycles) was carried out as follows: 30 seconds at 95° C., 15 seconds at 52° C., 1 minute at 68° C. with final extension for 7 minutes at 68° C. PCR reaction product (5 µl) was subjected to analytical electrophoresis on 2% pre-cast gels containing ethidium bromide (Invitrogen) and remaining product (45 µl) purified using the Qiaquick PCR Purification Kit (Qiagen). In vitro transcription was carried out for 4 hours using the T7 MegaScript Kit (Ambion) per manufacturer's recommendations. Reactions were subjected to nuclease digestion using Turbo DNase (Ambion) and subsequently purified using the MegaClear kit (Ambion). RNA was quantitated using a Nanoprop (Nanoprop Technologies, Wilmington, Del., USA) spectrophotometer, aliquoted and served as control cRNA.

Nucleotide Sequencing:

Purified amplicons were cloned using a Topo 2.0 Cloning Kit (Invitrogen) and sequenced using the Big Dye Terminator v3.1 reagent Kit. Unincorporated fluorescent nucleotides were removed using a Dye Ex 96-well plate kit per manufacturer's recommendations (Qiagen). Nucleotide sequencing was performed using an ABI 3100 Genetic Analyzer (ABI Inc., Foster City, Calif., USA).

Results:

As shown in FIG. 6, influenza A and B virus type specific assays detected all known influenza A hemagglutinin subtypes (H1-H16) and both type B (Yamagata and Victoria) viruses, respectively. Importantly, no cross-reactivity was observed between influenza A and B virus specific probes supporting the very specific nature of these assays. (Total RNA for influenza virus A H1-15 subtypes was obtained from Southeast Poultry Research Laboratory, USDA Agricultural Research Service (Athens, Ga., USA). H16 RNA was obtained from Erasmus Medical Center (Rotterdam, The Netherlands). Influenza B virus reference strains were obtained from the Department of Defense Global Emerging Infectious Surveillance (DoD-GEIS) network.)

H1, H3, and H5 influenza A subtype specific assays were initially evaluated using 180 archived clinical isolates. As shown in FIG. 7, 178 samples were correctly typed and subtyped in research blinded fashion; the far greater number of samples identified as Type-A influenza (91%) with the remainder, i.e., 9% being Type-B influenza. Of the Influenza A samples, the H3 subtype was the most prevalent (93.2%) with the remaining 6.8% H1 subtype. Two samples (District of Columbia) tested influenza virus negative (using type and subtype assays reported here) and were later confirmed as being Coxsackie B and Adenovirus (data not shown). Consistent with no cross-reactivity of type specific probes, no subtype specific probe cross-reactivity, i.e., H1, H3, and H5 assay cross-reactivity was observed. Furthermore, 40 commonly encountered bacteria/viruses were tested concurrently and did not amplify using either type- or subtype-specific primer/probes listed in Table 1 (data not shown).

Typing and subtyping influenza viruses at the point of care using uncultured (low viral titer) primary specimens are crucial for expanded surveillance. Shown in FIG. 8 is analysis of 167 uncultured primary clinical samples. Of the 167 specimens, 100 were correctly identified, i.e., typed (Influenza A or Influenza B: 60 and 40, respectively) and type A samples subtyped H1 or H3, 12 (20%) and 48 (80%), respectively. Furthermore, 67 negative influenza samples were subsequently determined to be culture negative for influenza viruses. Of the 60 Influenza A samples, 16 initially tested influenza negative in contrast to original culture data. The inability to detect 16 of the 100 influenza specimens could have arisen from base pair sequence 'drift' in the respective primer/probe binding regions, less than threshold amounts of extracted target RNA arising from prolonged storage/degradation at −80° C. and poor sample collection. Therefore, aliquots of all 16 samples were removed and transferred to monolayer PMK culture tubes and shell vials for further analysis. After 48 hours, 10 of the 16 shell vial-enriched samples tested positive by type specific rRT-PCR and standard immunoreagent fluorescence staining. The remaining 6 samples were checked/screened daily thereafter and 3 of 6 tested positive 5 days post inoculation and the remaining three testing positive 9 days post inoculation. All 16 Influenza A amplicons were further validated by sequence analysis (data not shown). The overall specificity of assays using original specimens as source of RNA was 100% (no cross hybridization) with an overall sensitivity of 90.4% (151 correct positives and negatives out of a total of 167 samples).

Figure 4B:
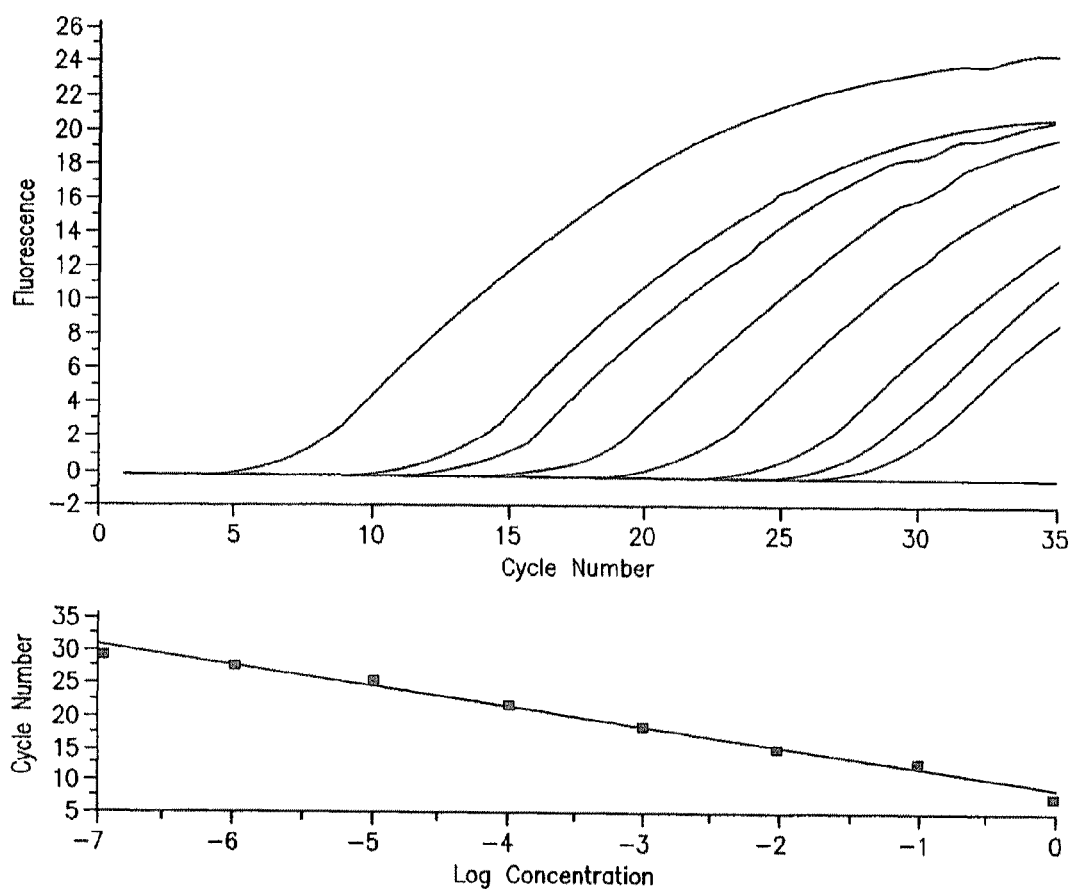
FIG. 4B shows $C_T$ data obtained from an Influenza A H5-specific thermal cycling assay.
Figure 10:
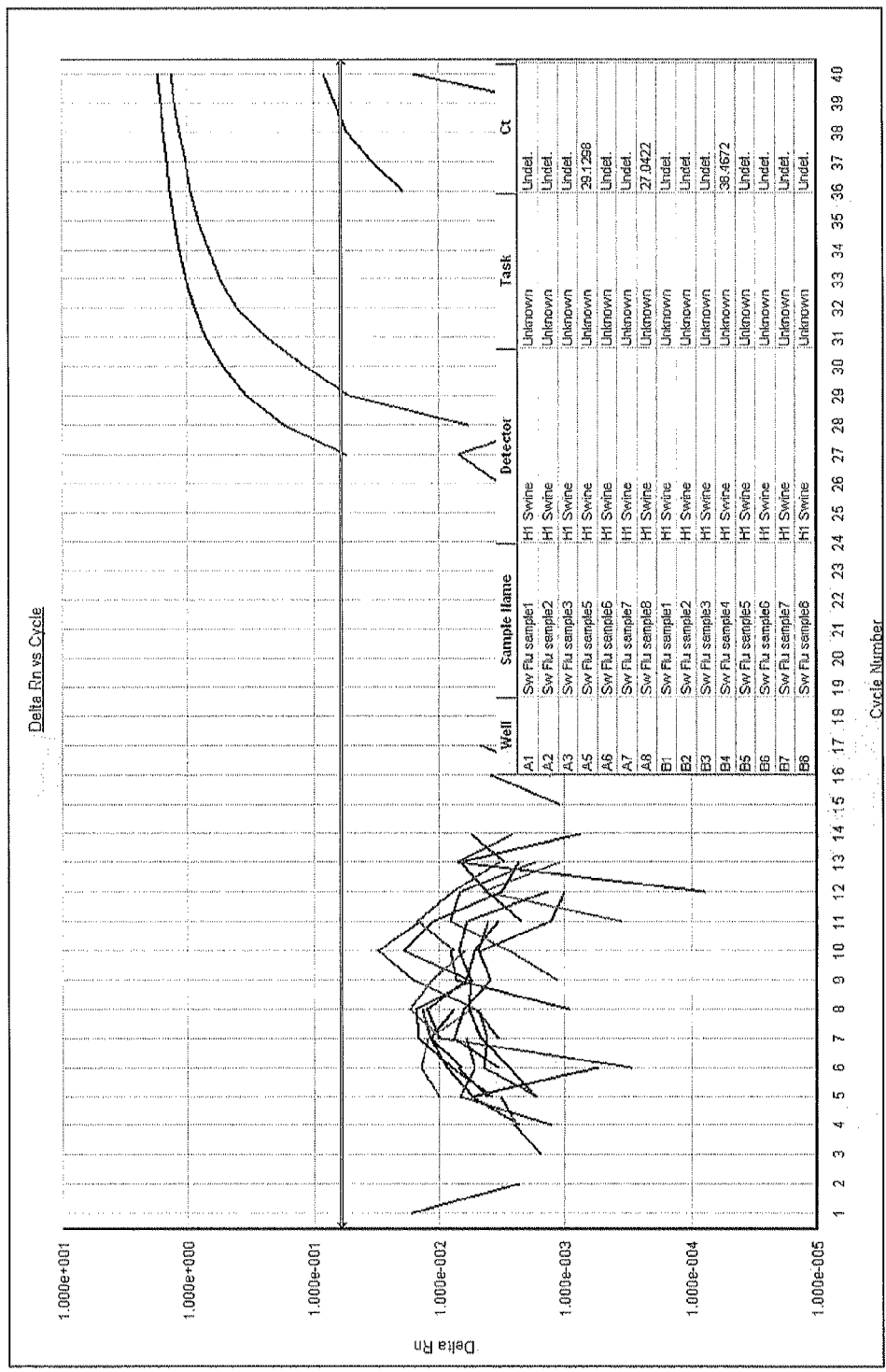
FIG. 10 depicts the real-time RT-PCR analysis of eight human clinical nasal wash samples preserved in PrimeMix™ Solution that includes primers and probe sequences for H1 swine 2009 strains (hereinafter "PrimeMix Swine H1"). Three of the eight samples tested positive for a H1 swine 2009 strain, as indicated by the real-time RT-PCR CT values.

Although no H5 influenza virus was observed in the sample collection (FIG. 7 and FIG. 8), the usefulness of the H5 subtype specific assay is demonstrated by alignment analysis of known H5 Influenza A virus with H5 primer/probe sequences and H5 assay sensitivity by template serial dilution. Shown in FIG. 4A is alignment analysis of 22 H5 Influenza A hemagglutinin sequences including an isolate from the first human H5 outbreak (1997) and subsequent outbreaks through 2006 with the H5 subtype specific, primer/probe sequences. Complete (100%) primer/probe, H5 virus sequence homology (avian and mammalian sources) was observed. Shown in FIG. 4B is a representative profile of serially diluted H5 cRNA template (obtained from a human fatality) over an 8-log dilution range ($10^{-9}$ to $10^{-16}$ g) corresponding to approximately 100 H5 cRNA target molecules ($10^{-16}$ g). Serially diluted cRNA targets (Influenza types A and B, and subtypes H1 and H3) exhibited very similar profiles to that shown in FIG. 4B.

Influenza type specific assays described in this report detected all 16 known type A viruses including the recently discovered H16 strain as well as both Yamagata and Victoria type B viruses (Fouchier R A, Munster V, Wallensten A, et al.: *Characterization of a novel influenza A virus hemagglutinin subtype (H16) obtained from black-headed gulls*, J. Virol., 79:2814-2822, 2005; specifically incorporated herein in its entirety by express reference thereto). Using both the laboratory-based LightCycler 2.0 instrument and its lightweight (50-lb) version, the Ruggedized Advanced Pathogen Identification Device (R.A.P.I.D.), 347 archived primary clinical samples (throat swab/nasal wash, 180 cultured and 167 uncultured), were typed, i.e., Influenza A or Influenza B and if Influenza A, which subtype. Of the 347 total samples evaluated, 278 were correctly identified as being Influenza type A (222) or Influenza type B (56), and all Influenza type A strains were subsequently sub-typed as either H1, H3 or H5. Influenza-negative (69) samples (see e.g., Tables 7 and 8: 2 from the District of Columbia, 66 from Nepal and 1 from Texas, respectively) were subsequently confirmed as Coxsackie B, Adenovirus, Parainfluenzas 1, 2, and 3 or virus negative (data not shown). Sixteen of the 100 uncultured primary clinical specimens (FIG. 4A) required subsequent culturing. Although real-time RT-PCR is capable of detecting the presence of nucleic acid from nonviable virus, this was not the case since all 16 primary samples were successfully cultured and identified suggesting target RNA degradation from prolonged storage at −80° C., poor sample collection or lower sensitivity in clinical samples than that observed for serially diluted cRNA.

Assay specificity is underscored by the absence of any cross-reactivity, i.e., false positives (of particular note H5). False negatives can arise for a variety of reasons, i.e., presence of RT-PCR inhibitors, low initial viral titer, RNA degradation, poor/low RNA recovery during extraction, user error, or reagent degradation. Although no notable differences in RNA recovery have been observed using manually extracted template compared to robotic extracted template (data not shown), inclusion of an internal positive control could be of value in monitoring the process from extraction through amplification (Das et al., 2006). It should be understood that this reference provides guidance on suitable lyophilization techniques that can be used in accordance with the present invention, and therefore this references is incorporated herein by express reference thereto.

Example 3

Detection of Influenza Virus-Specific Polynucleotide Sequences in Clinical Samples 128 samples from 64 cotton rats were taken from lung and nasal tissue. Some of the animals were influenza virus culture negative. cRNA was extracted from the samples and added to the prime mix. Real time rRT PCR analysis using ABI 7500 was performed, and influenza RNA was detected in the samples within 90 minutes. Importantly, influenza was detected at levels of about 1 to >100 influenza viruses in tissues.

Example 4

Diagnosis of H1N1 Influenza Infection

Eight human clinical saline nasal wash samples were collected from individuals suspected of having influenza. RNA from the samples was extracted as described above. The primer and probe design (FIG. 9) was developed from a previously described real-time RT PCR assay for the detection of contemporary circulating human H1 strains (Daum, et al., 2007). The primers and probe target RNA Segment 4, a conserved area within a highly variable region of the hemagglutinin (HA) gene. To generate 2009 H1N1-specific probes and primers, substitutions of nucleotides were made within the sequences of the previous probes and primers based on the particular nucleotide sequences observed in the 2009 H1N1 strains. The primers and probe were incorporated into the prime mix. Importantly, no cross-reactivity was observed between the H1N1-specific primers and probe and other contemporary circulating strains of H1 influenza. Generation of a cDNA template and real-time RT-PCR were performed similarly to that described above. Amplification efficiency was determined using the $C_T$ slope method (FIG. 10) according to the equation $E=[10^{(-1/Slope)}-1] \times 100$. Three of the eight samples were positive for flu using the H1N1 primers and probe. Two of the three positive results had high $C_T$ scores of 29 and 38, indicative of high viral loads and the other positive sample had a $C_T$ score of 27, indicating around 1 to around 10 viral copies.

Figure 11:
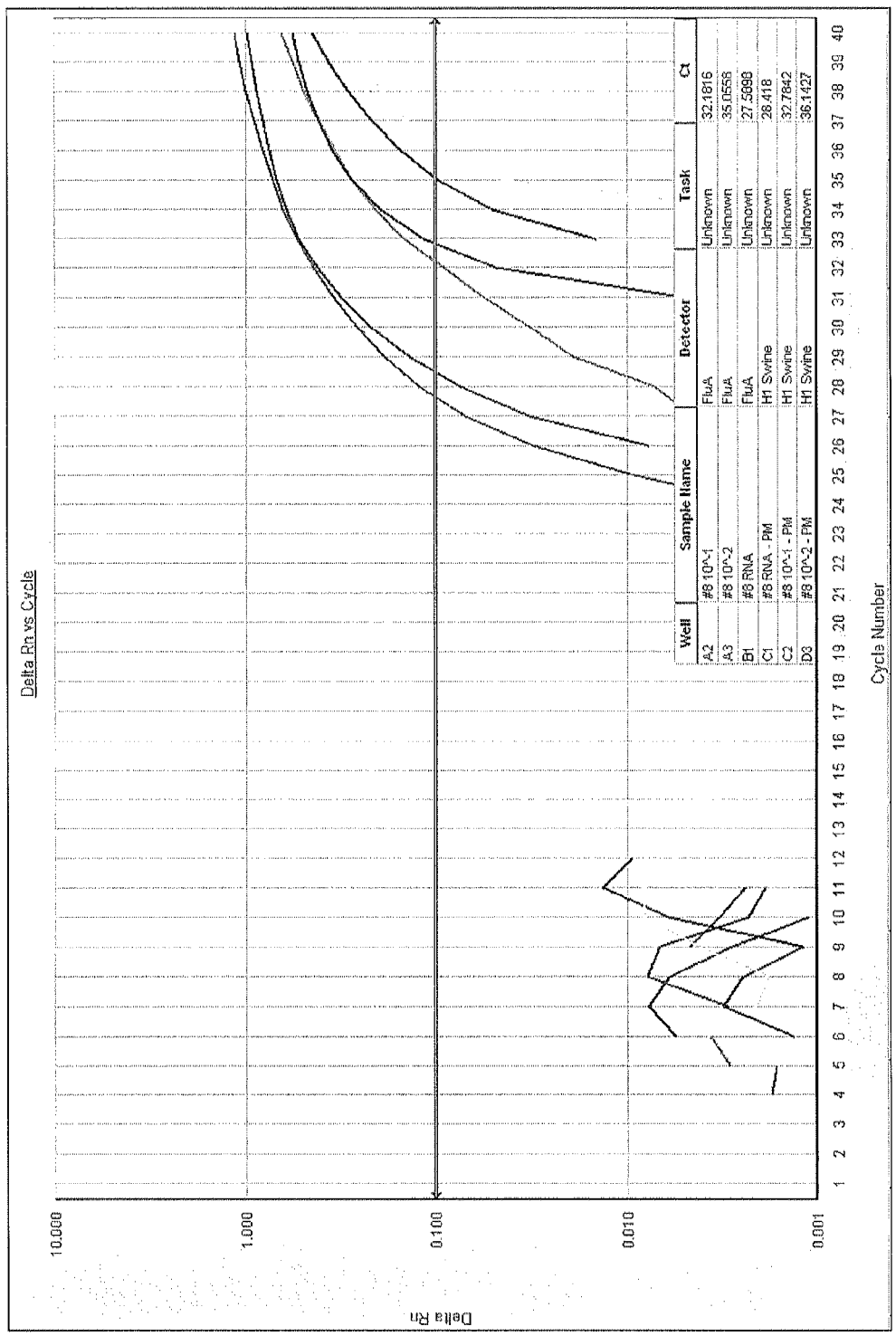
FIG. 11 depicts the 100-fold titration of a H1N1 positive human clinical sample when tested using universal Influenza A-specific primers and probe as well as the Swine flu 2009 H1N1-specific primers and probe in RT-PCR reactions. Both assays detected Influenza A RNA with similar amplification curves and $C_T$ values.

To ensure that the H1N1 specific primers and probe were detecting the correct sequences and to a similar degree as universal A flu primers and probes (See FIG. 5), a sample testing positive for H1N1 was taken, titrated and RT PCR was performed using universal A flu primers and probes and H1N1 specific primers and probes. Influenza RNA was detected in both instances at 100 fold titration and similar amplification and $C_T$ values resulted (See FIG. 11), thus indicating the ability of H1N1 specific primers and probes to detect at the presence of influenza A at similar titers.

All of the compositions and methods disclosed and claimed herein can be made and executed without undue experimentation in light of the present disclosure. While the compositions and methods of this invention have been described in terms of exemplary embodiments, it will be apparent to those of ordinary skill in the art that variations may be applied to the composition, methods and in the steps or in the sequence of steps of the method described herein without departing from the concept, spirit and scope of the invention. More specifically, it will be apparent that certain agents that are both chemically- and physiologically-related may be substituted for the agents described herein while the same or similar results would be achieved. All such similar substitutes and modifications apparent to those of ordinary skill in the art are deemed to be within the spirit, scope and concept of the invention as defined by the appended claims. Accordingly, the exclusive rights sought to be patented are as described in the claims below.

What is claimed is:

1. A method for detecting the presence of a specific nucleic acid in a biological sample that has been maintained for a period of time without refrigeration, comprising:
   adding the biological sample to a composition thereby forming an aqueous mixture, wherein the composition contains: one or more chaotropes; one or more detergents; one or more reducing agents; one or more defoaming agents, one or more chelators; one or more zwitterionic compounds; one or more albuminoids, and one or more buffers, collectively present in an amount sufficient to denature protein, inactivate nuclease, and kill pathogens that may be contained within the biological sample;
   performing a PCR reaction on the mixture, wherein the reaction is initiated by contacting the mixture with a sufficient quantity of PCR reaction components to form an amplification product of a sequence that is derived from the specific nucleic acid; and
   detecting the presence of the amplification product in the PCR amplified mixture, wherein the presence of the amplification product is indicative of the presence of the specific nucleic acid in the biological sample.

2. The method of claim 1, wherein:
   the one or more chaotropes are present at a concentration of about 0.5 M to about 6 M;
   the one or more detergents are present at a concentration of about 0.1% to about 1% (wt./vol.);
   the one or more reducing agents are present at a concentration of about 50 mM to about 0.3 M;
   the one or more defoaming agents are present at a concentration of about 0.0001% to about 0.3% (wt./vol.),
   the one or more chelators are present at a concentration of about 0.01 mM to about 1 mM;
   and the one or more buffers are present at a concentration of about 1 mM to about 1 M with a pH between about 6 and 8.

3. The method of claim 2, wherein:
   the one or more chaotropes comprise guanidine thiocyanate, guanidine isocyanate, guanidine hydrochloride, or any combination thereof;
   the one or more detergents comprise sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof;
   the one or more reducing agents comprise 2-mercaptoethanol, tris(2-carboxyethyl)phosphine, dithiothreitol, dimethylsulfoxide, or any combination thereof;
   the one or more chelators comprise ethylene glycol tetra acetic acid, hydroxyethylethylenediaminetriacetic acid, diethylene triamine penta acetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof;
   the one or more zwitterionic compounds comprise betaine, N,N,N-trimethylglycine, cocamidopropyl betaine or any combination thereof;
   the one or more albuminoids comprise ovalbumin, bovine serum albumin, or serum albumin; and
   the one or more buffers comprise tris(hydroxymethyl)aminomethane, citrate, 2-(N-morpholino)ethanesulfonic acid, N,N-Bis(2-hydroxyethyl)-2-aminoethanesulfonic acid, 1,3-bis(tris(hydroxymethyl)methyl amino)propane, 4-(2-hydroxyethyl)-1-piperazine ethanesulfonic acid, 3-(N-morpholino) propanesulfonic acid, bicarbonate, phosphate, or any combination thereof.

4. The method of claim 2, wherein the composition further comprises one or more osmolytes which are selected from the group consisting of trimethylamine N-oxide (TMAO), dimethylsulfoniopropionate, sarcosine, and any combination thereof.

5. The method of claim 2, wherein the composition further comprises one or more saccharides or sugar alcohols which are selected from the group consisting of trehalose, maltose, rhamnose, sucrose, arabinose, fucose, mannitol, sorbitol, adonitol and any combination thereof.

6. The method of claim 2, wherein the composition further comprises one or more short-chain alkanols present at a concentration of about 1% to 25% (vol./vol.), wherein the one or more short-chain alkanols are selected from the group consisting of methanol, ethanol, propanol, butanol, pentanol, hexanol, and any combination thereof.

7. The method of claim 1, wherein the composition further comprises:
   one or more osmolytes;
   one or more saccharides or sugar alcohols; and
   one or more short-chain alkanols.

8. The method of claim 2, wherein the specific nucleic acid is a sequence derived from a virus, a bacteria, a parasite or a fungus.

9. The method of claim 8, wherein the sequence is derived from influenza virus.

10. The method of claim 8, wherein the sequence is derived from Mycobacteria.

11. The method of claim 2, wherein the PCR reaction components comprise a pair of amplification primers specific for the amplification product, a polymerase, nucleotide triphosphates, and magnesium.

12. The method of claim 2, wherein the buffer has a pH of about 6 to 7.

13. The method of claim 2, wherein the period of time is at least 7 days.

14. The method of claim 13, wherein the period of time is at least 14 days.

15. The method of claim 14, wherein the period of time is at least 21 days.

16. The method of claim 1, further comprising detecting the presence or absence of a positive control sequence.

17. The method of claim 9, wherein the influenza virus is H1N1, H1N2, H2N2, H3N2, or H5N1.

* * * * *

```
                       SEQUENCE LISTING

<160> NUMBER OF SEQ ID NOS: 58

<210> SEQ ID NO 1
<211> LENGTH: 19
<212> TYPE: DNA
<213> ORGANISM: Artificial Sequence
<220> FEATURE:
<223> OTHER INFORMATION: Influenza Type A Forward Amplification Primer

<400> SEQUENCE: 1
taaccgaggt cgaaacgta                                                  19

<210> SEQ ID NO 2
<211> LENGTH: 16
<212> TYPE: DNA
<213> ORGANISM: Artificial Sequence
<220> FEATURE:
<223> OTHER INFORMATION: Influenza Type A Reverse Amplification Primer

<400> SEQUENCE: 2
gcacggtgag cgtgaa                                                     16

<210> SEQ ID NO 3
<211> LENGTH: 17
<212> TYPE: DNA
<213> ORGANISM: Artificial Sequence
<220> FEATURE:
<223> OTHER INFORMATION: Influenza Type A Probe
```

```
<400> SEQUENCE: 3
tcaggccccc tcaaagc                                                      17

<210> SEQ ID NO 4
<211> LENGTH: 24
<212> TYPE: DNA
<213> ORGANISM: Artificial Sequence
<220> FEATURE:
<223> OTHER INFORMATION: Influenza Type B Forward Amplification Primer

<400> SEQUENCE: 4
ggaattgcaa aggatgtaat ggaa                                              24

<210> SEQ ID NO 5
<211> LENGTH: 28
<212> TYPE: DNA
<213> ORGANISM: Artificial Sequence
<220> FEATURE:
<223> OTHER INFORMATION: Influenza Type B Reverse Amplification Primer

<400> SEQUENCE: 5
agaacaaatt gaaagaatct gaaatggt                                          28

<210> SEQ ID NO 6
<211> LENGTH: 17
<212> TYPE: DNA
<213> ORGANISM: Artificial Sequence
<220> FEATURE:
<223> OTHER INFORMATION: Influenza Type B Probe

<400> SEQUENCE: 6
atgggaaatt cagctct                                                      17

<210> SEQ ID NO 7
<211> LENGTH: 23
<212> TYPE: DNA
<213> ORGANISM: Artificial Sequence
<220> FEATURE:
<223> OTHER INFORMATION: Influenza Subtype H1 Forward Amplification
      Primer

<400> SEQUENCE: 7
agycttcctt tccagaatgt aca                                               23

<210> SEQ ID NO 8
<211> LENGTH: 25
<212> TYPE: DNA
<213> ORGANISM: Artificial Sequence
<220> FEATURE:
<223> OTHER INFORMATION: Influenza Subtype H1 Reverse Amplification
      Primer

<400> SEQUENCE: 8
agtcctgtar ccatycttaa ttttg                                             25

<210> SEQ ID NO 9
<211> LENGTH: 18
<212> TYPE: DNA
<213> ORGANISM: Artificial Sequence
<220> FEATURE:
<223> OTHER INFORMATION: Influenza Subtype H1 Probe

<400> SEQUENCE: 9
tctccaaagt atgtcagg                                                     18
```

<210> SEQ ID NO 10
<211> LENGTH: 22
<212> TYPE: DNA
<213> ORGANISM: Artificial Sequence
<220> FEATURE:
<223> OTHER INFORMATION: Influenza Subtype H3 Forward Amplification
      Primer

<400> SEQUENCE: 10
aatacgaagt gggaaaagct ca                                          22

<210> SEQ ID NO 11
<211> LENGTH: 23
<212> TYPE: DNA
<213> ORGANISM: Artificial Sequence
<220> FEATURE:
<223> OTHER INFORMATION: Influenza Subtype H3 Reverse Amplification
      Primer

<400> SEQUENCE: 11
gccccrtatg tgatyctgtt tac                                         23

<210> SEQ ID NO 12
<211> LENGTH: 19
<212> TYPE: DNA
<213> ORGANISM: Artificial Sequence
<220> FEATURE:
<223> OTHER INFORMATION: Influenza Subtype H3 Probe

<400> SEQUENCE: 12
tgagatcaga tgcacccat                                              19

<210> SEQ ID NO 13
<211> LENGTH: 25
<212> TYPE: DNA
<213> ORGANISM: Artificial Sequence
<220> FEATURE:
<223> OTHER INFORMATION: Influenza Subtype H5 Forward Amplification
      Primer

<400> SEQUENCE: 13
actayccgca gtattcagaa gaagc                                       25

<210> SEQ ID NO 14
<211> LENGTH: 21
<212> TYPE: DNA
<213> ORGANISM: Artificial Sequence
<220> FEATURE:
<223> OTHER INFORMATION: Influenza Subtype H5 Reverse Amplification
      Primer

<400> SEQUENCE: 14
gaccagcyay catgattgcc a                                           21

<210> SEQ ID NO 15
<211> LENGTH: 17
<212> TYPE: DNA
<213> ORGANISM: Artificial Sequence
<220> FEATURE:
<223> OTHER INFORMATION: Influenza Subtype H5 Probe

<400> SEQUENCE: 15
agagrggaaa taagtgg                                                17

<210> SEQ ID NO 16
<211> LENGTH: 45

```
<212> TYPE: DNA
<213> ORGANISM: Artificial Sequence
<220> FEATURE:
<223> OTHER INFORMATION: Influenza Type A Forward Amplification Primer

<400> SEQUENCE: 16
gctaatacga ctcactatag ggagaagcaa aagcaggtag atatt                 45

<210> SEQ ID NO 17
<211> LENGTH: 24
<212> TYPE: DNA
<213> ORGANISM: Artificial Sequence
<220> FEATURE:
<223> OTHER INFORMATION: Influenza Type A Reverse Amplification Primer

<400> SEQUENCE: 17
agtagaaaca aggtagtttt ttac                                        24

<210> SEQ ID NO 18
<211> LENGTH: 45
<212> TYPE: DNA
<213> ORGANISM: Artificial Sequence
<220> FEATURE:
<223> OTHER INFORMATION: Influenza Type B Forward Amplification Primer

<400> SEQUENCE: 18
gctaatacga ctcactatag ggagatcgct gtttggagac acaat                 45

<210> SEQ ID NO 19
<211> LENGTH: 20
<212> TYPE: DNA
<213> ORGANISM: Artificial Sequence
<220> FEATURE:
<223> OTHER INFORMATION: Influenza Type B Reverse Amplification Primer

<400> SEQUENCE: 19
ctccaaaact gtttcaccca                                             20

<210> SEQ ID NO 20
<211> LENGTH: 43
<212> TYPE: DNA
<213> ORGANISM: Artificial Sequence
<220> FEATURE:
<223> OTHER INFORMATION: Influenza Type H1 Forward Amplification Primer

<400> SEQUENCE: 20
gctaatacga ctcactatag ggagaaagca ggggaaaata aaa                   43

<210> SEQ ID NO 21
<211> LENGTH: 18
<212> TYPE: DNA
<213> ORGANISM: Artificial Sequence
<220> FEATURE:
<223> OTHER INFORMATION: Influenza Type H1 Reverse Amplification Primer

<400> SEQUENCE: 21
gtaatcccgt taatcgca                                               18

<210> SEQ ID NO 22
<211> LENGTH: 43
<212> TYPE: DNA
<213> ORGANISM: Artificial Sequence
<220> FEATURE:
<223> OTHER INFORMATION: Influenza Subtype H3 Forward Amplification
      Primer

<400> SEQUENCE: 22
 gctaatacga ctcactatag ggagaactat cattgctttg agc           43

<210> SEQ ID NO 23
<211> LENGTH: 18
<212> TYPE: DNA
<213> ORGANISM: Artificial Sequence
<220> FEATURE:
<223> OTHER INFORMATION: Influenza Subtype H3 Reverse Amplification
      Primer

<400> SEQUENCE: 23
atggctgctt gagtgctt                                      18

<210> SEQ ID NO 24
<211> LENGTH: 47
<212> TYPE: DNA
<213> ORGANISM: Artificial Sequence
<220> FEATURE:
<223> OTHER INFORMATION: Influenza Subtype H5 Forward Amplification
      Primer

<400> SEQUENCE: 24
gctaatacga ctcactatag ggagatcatc tgtcaaatgg agaaaat      47

<210> SEQ ID NO 25
<211> LENGTH: 22
<212> TYPE: DNA
<213> ORGANISM: Artificial Sequence
<220> FEATURE:
<223> OTHER INFORMATION: Influenza Subtype H5 Reverse Amplification
      Primer

<400> SEQUENCE: 25
aaggatagac cagctaccat ga                                 22

<210> SEQ ID NO 26
<211> LENGTH: 146
<212> TYPE: DNA
<213> ORGANISM: Influenza A virus

<400> SEQUENCE: 26
gactacccgc agtattcaga agaagcaaga ttaaaaagag aggaaataag tggagtaaaa 60
ttggaatcaa taggaactta ccaaatactg tcaatttatt caacagttgc gagttctcta 120
gcactggcaa tcatggtggc tggtct 146

<210> SEQ ID NO 27
<211> LENGTH: 146
<212> TYPE: DNA
<213> ORGANISM: Influenza A virus

<400> SEQUENCE: 27
gactacccgc agtattcaga agaagcaaga ttaaaaagag aggaaataag tggagtaaaa 60
ttggaatcaa taggaactta ccaaatactg tcaatttatt caacagttgc gagttctcta 120
gcactggcaa tcatggtggc tggtct 146

<210> SEQ ID NO 28
<211> LENGTH: 146
<212> TYPE: DNA
<213> ORGANISM: Influenza A virus

<400> SEQUENCE: 28
gactacccgc agtattcaga agaagcaaga ttaaaaagag aggaaataag tggagtaaaa 60

```
ttggaatcaa taggaactta ccaaatactg tcaatttatt caacagtggc gagctcccta    120
gcactggcaa tcatggtggc tggtct                                         146

<210> SEQ ID NO 29
<211> LENGTH: 146
<212> TYPE: DNA
<213> ORGANISM: Influenza A virus

<400> SEQUENCE: 29
gactacccgc agtattcaga agaagcaaga ttaaaaagag aggaaataag tggagtaaaa    60
ttggaatcaa taggaattta ccaaatactg tcaatttatt ctacagtggc gagttcccta   120
gcactggcaa tcatggtagc tggtct                                        146

<210> SEQ ID NO 30
<211> LENGTH: 146
<212> TYPE: DNA
<213> ORGANISM: Influenza A virus

<400> SEQUENCE: 30
gactacccgc agtattcaga agaagcaaga ttaaaaagag aggaaataag tggagtaaaa    60
ttggaatcaa taggaactta ccaaatactg tcaatttatt caacagtggc gagttcccta   120
gcactggcaa tcatggtggc tggtct                                        146

<210> SEQ ID NO 31
<211> LENGTH: 146
<212> TYPE: DNA
<213> ORGANISM: Influenza A virus

<400> SEQUENCE: 31
gactacccgc agtattcaga agaagcaaga ctaaacagag aggaaataag tggagtaaaa    60
ttggaatcaa tgggaattta ccaaatactg tcaatttatt caacagtggc gagttcccta   120
gcactggcaa tcatggtagc tggtct                                        146

<210> SEQ ID NO 32
<211> LENGTH: 146
<212> TYPE: DNA
<213> ORGANISM: Influenza A virus

<400> SEQUENCE: 32
gactacccgc agtattcaga agaagcaaga ctaaacagag aggaaataag tggagtaaaa    60
ttggaatcaa tgggaactta ccaaatactg tcaatttatt caacagtggc gagttcccta   120
gcactggcaa tcatggtagc tggtct                                        146

<210> SEQ ID NO 33
<211> LENGTH: 146
<212> TYPE: DNA
<213> ORGANISM: Influenza A virus

<400> SEQUENCE: 33
gactacccgc agtattcaga agaagcaaga ttaaaaagag aggaaataag tggagtaaaa    60
ttggaatcaa taggaactta ccaaatcctg tcaatttatt caacagtggc gagctcccta   120
gcactggcaa tcatggtggc tggtct                                        146

<210> SEQ ID NO 34
<211> LENGTH: 146
<212> TYPE: DNA
```

<213> ORGANISM: Influenza A virus

<400> SEQUENCE: 34

```
gactacccgc agtattcaga agaagcaaga

<210> SEQ ID NO 40
<211> LENGTH: 146
<212> TYPE: DNA
<213> ORGANISM: Influenza A virus

<400> SEQUENCE: 40
gactacccgc agtattcaga agaagcaaga ttaaaagag aggaaataag tggagtaaaa      60
ttggaatcaa taggaattta ccaaatactg tcaatttatt caacagtggc gagctcccta    120
gcactggcaa tcatggtggc tggtct                                         146

<210> SEQ ID NO 41
<211> LENGTH: 146
<212> TYPE: DNA
<213> ORGANISM: Influenza A virus

<400> SEQUENCE: 41
gactacccgc agtattcaga agaagcgaga ctaaaaagag aggaaataag tggagtaaaa 60
ttggaatcaa taggaattta ccaaatactg tcaatttatt ctacagtggc gagttcccta 120
gcactggcaa tcatggtagc tggtct 146

<210> SEQ ID NO 42
<211> LENGTH: 146
<212> TYPE: DNA
<213> ORGANISM: Influenza A virus

<400> SEQUENCE: 42
gactacccgc agtattcaga agaagcaaga ttaaaaagag aggaaataag tggagtaaaa 60
ttggaatcaa taggaattta ccaaatactg tcaatttatt ctacagtggc gagttcccta 120
gcactggcaa tcatggtagc tggtct 146

<210> SEQ ID NO 43
<211> LENGTH: 145
<212> TYPE: DNA
<213> ORGANISM: Influenza A virus

<400> SEQUENCE: 43
gactacccgc agtattcaga agaagcaaga ctaaaaagag aggaaataag tggagtaaaa 60
ttggagtcaa taggaactta ccaaatactg tcaatttatt ctacagtggc gagttcccta 120
gcactggcaa tcatggtagc tggtc 145

<210> SEQ ID NO 44
<211> LENGTH: 145
<212> TYPE: DNA
<213> ORGANISM: Influenza A virus

<400> SEQUENCE: 44
gactacccgc agtattcaga agaagcaaga ctaaaaagag aggaaataag tggagtaaaa 60
ttggaatcaa taggaattta ccaaatattg tcaatttatt ctacagtggc gagctcccta 120
gcactggcaa tcatggtagc tggtc 145

<210> SEQ ID NO 45
<211> LENGTH: 145
<212> TYPE: DNA
<213> ORGANISM: Influenza A virus

<400> SEQUENCE: 45

```
gactacccgc agtattcaga agaagcaaga ttaaaaagag aggaaataag tggagtaaaa    60
ttggaatcaa taggaactta ccaaatactg tcaattnatt caacagtggc gagctccccta  120 gcactggcaa tcatggtggc tggtc                                         145

<210> SEQ ID NO 46
<211> LENGTH: 145
<212> TYPE: DNA
<213> ORGANISM: Influenza A virus

<400> SEQUENCE: 46
aactatccgc agtattcaga agaagcaaga ttaaaaagag aggaaataag tggggtaaaa    60
ttggaatcaa taggaactta ccaaatactg tcaattnatt caacagtggc gagttcccta  120
gcactggcaa tcatgatggc tggtc                                         145

<210> SEQ ID NO 47
<211> LENGTH: 145
<212> TYPE: DNA
<213> ORGANISM: Influenza A virus

<400> SEQUENCE: 47
aactatccgc agtattcaga agaagcaaga ttaaaaagag aggaaataag tggggtaaaa    60
ttggaatcaa taggaactta ccaaatactg tcaattnatt caacagtggc gagttcccta  120
gcactggcaa tcatgatggc tggtc                                         145

<210> SEQ ID NO 48
<211> LENGTH: 25
<212> TYPE: DNA
<213> ORGANISM: Artificial Sequence
<220> FEATURE:
<223> OTHER INFORMATION: H5 Primer

<400> SEQUENCE: 48
actayccgca gtattcagaa gaagc                                         25

<210> SEQ ID NO 49
<211> LENGTH: 17
<212> TYPE: DNA
<213> ORGANISM: Artificial Sequence
<220> FEATURE:
<223> OTHER INFORMATION: influenza consensus domain

<400> SEQUENCE: 49
agagrggaaa taagtgg                                                  17

<210> SEQ ID NO 50
<211> LENGTH: 21
<212> TYPE: DNA
<213> ORGANISM: Artificial Sequence
<220> FEATURE:
<223> OTHER INFORMATION: Reverse Primer

<400> SEQUENCE: 50
tggcaatcat grtrgctggt c                                             21

<210> SEQ ID NO 51
<211> LENGTH: 23
<212> TYPE: DNA
<213> ORGANISM: Artificial Sequence
<220> FEATURE:
<223> OTHER INFORMATION: Influenza A H1N1 Forward Primer

<400> SEQUENCE: 51
```

```
agcctyccat ttcagaatat aca                                            23

<210> SEQ ID NO 52
<211> LENGTH: 25
<212> TYPE: DNA
<213> ORGANISM: Artificial Sequence
<220> FEATURE:
<223> OTHER INFORMATION: Influenza A H1N1 Reverse Primer

<400> SEQUENCE: 52
aatcctgtrg ccagtctcaa ttttg                                          25

<210> SEQ ID NO 53
<211> LENGTH: 18
<212> TYPE: DNA
<213> ORGANISM: Artificial Sequence
<220> FEATURE:
<223> OTHER INFORMATION: Influenza A H1N1 Probe

<400> SEQUENCE: 53
tccaaaatat gtaaaaag                                                  18

<210> SEQ ID NO 54
<211> LENGTH: 17
<212> TYPE: DNA
<213> ORGANISM: Artificial Sequence
<220> FEATURE:
<223> OTHER INFORMATION: Influenza Oligonucleotide Probe

<400> SEQUENCE: 54
tcaggccccc tcaaagc                                                   17

<210> SEQ ID NO 55
<211> LENGTH: 17
<212> TYPE: DNA
<213> ORGANISM: Artificial Sequence
<220> FEATURE:
<223> OTHER INFORMATION: Influenza Oligonucleotide Probe

<400> SEQUENCE: 55
atgggaaatt cagctct                                                   17

<210> SEQ ID NO 56
<211> LENGTH: 18
<212> TYPE: DNA
<213> ORGANISM: Artificial Sequence
<220> FEATURE:
<223> OTHER INFORMATION: Influenza Oligonucleotide Probe

<400> SEQUENCE: 56
tctccaaagt atgtcagg                                                  18

<210> SEQ ID NO 57
<211> LENGTH: 19
<212> TYPE: DNA
<213> ORGANISM: Artificial Sequence
<220> FEATURE:
<223> OTHER INFORMATION: Influenza Oligonucleotide Probe

<400> SEQUENCE: 57
```

```
tgagatcaga tgcacccat                                                      19

<210> SEQ ID NO 58
<211> LENGTH: 17
<212> TYPE: DNA
<213> ORGANISM: Artificial Sequence
<220> FEATURE:
<223> OTHER INFORMATION: Influenza Oligonucleotide Probe

<400> SEQUENCE: 58
agagrggaaa taagtgg                                                        17
```